(12) United States Patent
Goosens

(10) Patent No.: US 10,039,813 B2
(45) Date of Patent: Aug. 7, 2018

(54) USE OF ANTAGONISTS OF GHRELIN OR GHRELIN RECEPTOR TO PREVENT OR TREAT STRESS-SENSITIVE PSYCHIATRIC ILLNESS

(71) Applicant: Massachusetts Institute of Technology, Cambridge, MA (US)

(72) Inventor: Ki Ann Goosens, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 96 days.

(21) Appl. No.: 14/377,229

(22) PCT Filed: Feb. 7, 2013

(86) PCT No.: PCT/US2013/025130
§ 371 (c)(1),
(2) Date: Aug. 7, 2014

(87) PCT Pub. No.: WO2013/119800
PCT Pub. Date: Aug. 15, 2013

(65) Prior Publication Data
US 2015/0297691 A1    Oct. 22, 2015

Related U.S. Application Data

(60) Provisional application No. 61/595,845, filed on Feb. 7, 2012.

(51) Int. Cl.
| | | |
|---|---|---|
| *A01N 57/00* | (2006.01) | |
| *A61K 31/66* | (2006.01) | |
| *A61K 39/00* | (2006.01) | |
| *A61K 38/27* | (2006.01) | |
| *C12N 15/113* | (2010.01) | |
| *A61K 45/00* | (2006.01) | |
| *G01N 33/74* | (2006.01) | |
| *A61K 38/17* | (2006.01) | |

(52) U.S. Cl.
CPC ...... *A61K 39/0005* (2013.01); *A61K 38/1796* (2013.01); *A61K 45/00* (2013.01); *G01N 33/74* (2013.01); *A61K 39/00* (2013.01); *A61K 2039/545* (2013.01); *G01N 2333/60* (2013.01); *G01N 2800/7004* (2013.01)

(58) Field of Classification Search
None
See application file for complete search history.

(56) References Cited

U.S. PATENT DOCUMENTS

| | | | |
|---|---|---|---|
| 4,857,637 | A | 8/1989 | Hammonds et al. |
| 4,997,815 | A | 3/1991 | Perrine et al. |
| 7,479,271 | B2 | 1/2009 | Marquis et al. |
| 7,632,809 | B2 | 12/2009 | Chen |
| 7,666,833 | B2 | 2/2010 | Ghigo et al. |
| 7,901,679 | B2 | 3/2011 | Marquis et al. |
| 8,013,015 | B2 | 9/2011 | Harran et al. |
| 8,293,709 | B2 | 10/2012 | Ross et al. |
| 9,724,396 | B2 | 8/2017 | Goosens |
| 2002/0187938 | A1 | 12/2002 | Deghenghi |
| 2003/0032636 | A1 | 2/2003 | Cremers et al. |
| 2004/0033948 | A1 | 2/2004 | Chen |
| 2005/0070712 | A1 | 3/2005 | Kosogof et al. |
| 2005/0148515 | A1 | 7/2005 | Dong |
| 2005/0187237 | A1 | 8/2005 | Distefano et al. |
| 2005/0191317 | A1 | 9/2005 | Bachmann et al. |
| 2005/0201938 | A1 | 9/2005 | Bryant et al. |
| 2005/0257279 | A1 | 11/2005 | Qian et al. |
| 2006/0025344 | A1 | 2/2006 | Lange et al. |
| 2006/0025566 | A1 | 2/2006 | Hoveyda et al. |
| 2006/0293370 | A1 | 12/2006 | Saunders et al. |
| 2007/0021331 | A1 | 1/2007 | Fraser et al. |
| 2007/0025991 | A1 | 2/2007 | Pothoulakis et al. |
| 2007/0037857 | A1 | 2/2007 | Perrissoud et al. |
| 2007/0191283 | A1 | 8/2007 | Polvino |
| 2007/0237775 | A1 | 10/2007 | Kikly et al. |
| 2007/0275877 | A1 | 11/2007 | Baron et al. |
| 2008/0058405 | A1 | 3/2008 | Lewy |
| 2008/0119540 | A1 | 5/2008 | Thompson |
| 2008/0242619 | A1 | 10/2008 | Dong |
| 2008/0261873 | A1 | 10/2008 | Geesaman |
| 2008/0262042 | A1 | 10/2008 | Kajino et al. |
| 2008/0300194 | A1 | 12/2008 | Mann et al. |
| 2009/0069245 | A1 | 3/2009 | Bowers et al. |
| 2009/0131478 | A1 | 5/2009 | Dong et al. |
| 2009/0143310 | A1 | 6/2009 | Polvino et al. |
| 2009/0149512 | A1 | 6/2009 | Raun et al. |
| 2009/0156483 | A1 | 6/2009 | Dong et al. |
| 2009/0156642 | A1 | 6/2009 | Nishida et al. |

(Continued)

FOREIGN PATENT DOCUMENTS

| | | |
|---|---|---|
| WO | WO 1993/018761 A1 | 9/1993 |
| WO | WO 1997/11178 A1 | 3/1997 |

(Continued)

OTHER PUBLICATIONS

Miller et al., Psychol. Bull., 2007, 133(1):25-45.*
Tsigos et al., J. Psychosom. Res., 2002, 53:865-71.*
Conrad, Pr. Neuro- Psychopharm. & Behavior. Psychiat, 2010, 34:742-55.*
Diano et al., Ghrelin controls hippocampal spine synapse density and memory performance. Nat Neurosci. Mar. 2006;9(3):381-8. Epub Feb. 19, 2006.
Meyer et al., A ghrelin-growth hormone axis drives stress-induced vulnerability to enhanced fear. Mol Psychiatry. Oct. 15, 2013. doi: 10.1038/mp.2013.135.

(Continued)

*Primary Examiner* — Olga N Chernyshev
(74) *Attorney, Agent, or Firm* — Wolf, Greenfield & Sacks, P.C.

(57) ABSTRACT

The invention relates to methods of protecting against chronic stress in a subject and treating stress sensitive disorders in a subject by antagonizing ghrelin or ghrelin receptor.

10 Claims, 28 Drawing Sheets

(56) References Cited

U.S. PATENT DOCUMENTS

| | | |
|---|---|---|
| 2009/0163416 A1 | 6/2009 | Tulipano et al. |
| 2009/0253673 A1 | 10/2009 | Ge et al. |
| 2009/0275511 A1 | 11/2009 | Dong |
| 2009/0275648 A1 | 11/2009 | Fraser et al. |
| 2010/0021487 A1 | 1/2010 | Zorrilla et al. |
| 2010/0086955 A1 | 4/2010 | Harran et al. |
| 2010/0196330 A1 | 8/2010 | Ghigo et al. |
| 2010/0196396 A1 | 8/2010 | Szentirmai et al. |
| 2010/0227806 A1 | 9/2010 | Giovanni |
| 2010/0254994 A1 | 10/2010 | Raso |
| 2010/0272734 A1 | 10/2010 | Berger et al. |
| 2010/0286152 A1 | 11/2010 | Bernasconi et al. |
| 2011/0021420 A1 | 1/2011 | Bloom et al. |
| 2011/0245160 A1 | 10/2011 | Van Der Lely |
| 2011/0245161 A1 | 10/2011 | Mintz |
| 2011/0257086 A1 | 10/2011 | Cole et al. |
| 2011/0269777 A1 | 11/2011 | Bachurin et al. |
| 2011/0318807 A1 | 12/2011 | Harran et al. |
| 2012/0095070 A1 | 4/2012 | Springer et al. |
| 2012/0129767 A1 | 5/2012 | Tulipano et al. |
| 2012/0232113 A1 | 9/2012 | Mann et al. |
| 2012/0237521 A1 | 9/2012 | Berger et al. |
| 2013/0123170 A1 | 5/2013 | Dong |
| 2013/0289068 A1 | 10/2013 | Polvino |
| 2013/0344091 A1 | 12/2013 | Berger et al. |
| 2014/0031393 A1 | 1/2014 | Nishida et al. |
| 2014/0088139 A1 | 3/2014 | Zollers et al. |
| 2014/0274900 A1 | 9/2014 | Goosens |
| 2014/0287997 A1 | 9/2014 | Goosens |
| 2014/0328848 A1 | 11/2014 | Feige et al. |
| 2015/0031615 A1 | 1/2015 | Dong |
| 2016/0058851 A1 | 3/2016 | Goosens |
| 2016/0106821 A1 | 4/2016 | Goosens |
| 2016/0243197 A1 | 8/2016 | Goosens |
| 2017/0007618 A1 | 1/2017 | Goosens et al. |

FOREIGN PATENT DOCUMENTS

| | | | |
|---|---|---|---|
| WO | WO 1997/041878 A1 | 11/1997 | |
| WO | WO 2001/000676 A1 | 1/2001 | |
| WO | WO 2003/092725 A1 | 11/2003 | |
| WO | WO 2004/021984 A2 | 3/2004 | |
| WO | WO 2005/097830 A2 | 10/2005 | |
| WO | WO 2005/112903 A2 | 12/2005 | |
| WO | WO 2006/019577 A1 | 2/2006 | |
| WO | WO 2008/004972 A2 | 1/2008 | |
| WO | WO 2010/132580 A2 | 11/2010 | |
| WO | WO 2010/051447 A1 | 5/2011 | |
| WO | WO 2011/053821 A1 | 5/2011 | |
| WO | WO 2013/119800 A1 | 8/2013 | |
| WO | WO 2013/155504 A1 | 10/2013 | |
| WO | WO 2014/027899 A1 | 2/2014 | |

OTHER PUBLICATIONS

Meyer et al., Chronic ghrelin receptor activation enhances Pavlovian fear learning without increasing anxiety. Society for Neuroscience Abstract Viewer and Itinerary Planner. 2009;39.

Meyer et al., Poster B7: Ghrelin signaling modulates amygdala-dependent Learning. The Neuroscience of Emotion: From Reaction to Regulation. Jun. 4, 2009.

Xin et al., Discovery and pharmacological evaluation of growth hormone secretagogue receptor antagonists. J Med Chem. Jul. 27, 2006;49(15):4459-69.

Anagnostaras et al., Hippocampus and contextual fear conditioning: recent controversies and advances. Hippocampus. 2001;11(1):8-17.

Bangasser et al., The hippocampus is necessary for enhancements and impairments of learning following stress. Nat Neurosci. Nov. 2007;10(11):1401-3. Epub Sep. 30, 2007.

Chaplin et al., Improvements in behaviour and self-esteem following growth hormone treatment in short prepubertal children. Horm Res Paediatr. 2011;75(4):291-303. doi: 10.1159/000322937. Epub Feb. 5, 2011.

De Quervain et al., Stress and glucocorticoids impair retrieval of long-term spatial memory. Nature. Aug. 20, 1998;394(6695):787-90.

Donahue et al., Growth hormone is produced within the hippocampus where it responds to age, sex, and stress. Proc Natl Acad Sci U S A. Apr. 11, 2006;103(15):6031-6. Epub Mar. 30, 2006.

Donahue et al., Transcriptional profiling reveals regulated genes in the hippocampus during memory formation. Hippocampus. 2002;12(6):821-33.

Fleshner et al., The neurobiology of the stress-resistant brain. Stress. Sep. 2011;14(5):498-502. doi: 10.3109/10253890.2011.596865. Epub Jul. 26, 2011.

Goosens, Hippocampal regulation of aversive memories. Curr Opin Neurobiol. Jun. 2011;21(3):460-6. doi: 10.1016/j.conb.Apr. 3, 2011. Epub May 3, 2011.

Graham et al., Recombinant human growth hormone in abstinent androgenic-anabolic steroid use: psychological, endocrine and trophic factor effects. Curr Neurovasc Res. Feb. 2007;4(1):9-18.

Kaufer et al., Restructuring the neuronal stress response with anti-glucocorticoid gene delivery. Nat Neurosci. Sep. 2004;7(9):947-53. Epub Aug. 8, 2004.

Kojima et al., Ghrelin is a growth-hormone-releasing acylated peptide from stomach. Nature. Dec. 9, 1999;402(6762):656-60.

Krishnan et al. Animal models of depression: molecular perspectives. Curr Top Behav Neurosci. 2011;121-47. doi: 10.1007/7854_2010_108.

Lakshminarasimhan et al., Stress leads to contrasting effects on the levels of brain derived neurotrophic factor in the hippocampus and amygdala. PloS One. 2012;7(1):e30481. doi: 10.1371/journal.pone.0030481. Epub Jan. 17, 2012.

Le Grevès et al., Growth hormone induces age-dependent alteration in the expression of hippocampal growth hormone receptor and N-methyl-D-aspartate receptor subunits gene transcripts in male rats. Proc Natl Acad Sci U S A. May 14, 2002;99(10):7119-23.

Lederbogen et al., City living and urban upbringing affect neural social stress processing in humans. Nature. Jun. 22, 2011;474(7352):498-501. doi: 10.1038/nature10190.

Magariños et al., Stress-induced atrophy of apical dendrites of hippocampal CA3c neurons: involvement of glucocorticoid secretion and excitatory amino acid receptors. Neuroscience. Nov. 1995;69(1):89-98.

Mahajan et al., Atypical depression in growth hormone deficient adults, and the beneficial effects of growth hormone treatment on depression and quality of life. Eur J Endocrinol. Sep. 2004;151(3):325-32.

Mahmoud et al., Growth hormone enhances excitatory synaptic transmission in area CA1 of rat hippocampus. J Neurophysiol. May 2006;95(5):2962-74. Epub Feb. 15, 2006.

Makatsori et al., Modulation of neuroendocrine response and non-verbal behavior during psychosocial stress in healthy volunteers by the glutamate release-inhibiting drug lamotrigine. Neuroendocrinology. Jan. 2004;79(1):34-42.

Maric et al., Psychiatric and neuropsychological changes in growth hormone-deficient patients after traumatic brain injury in response to growth hormone therapy. J Endocrinol Invest. Dec. 2010;33(11):770-5. doi: 10.3275/7045. Epub May 17, 2010.

McEwen, Protective and damaging effects of stress mediators. N Engl J Med. Jan. 15, 1998;338(3):171-9.

Molina et al., Growth hormone modulates hippocampal excitatory synaptic transmission and plasticity in old rats. Neurobiol Aging. Sep. 2012;33(9):1938-49. doi: 10.1016/j.neurobiolaging.Sep. 14, 2011. Epub Oct. 19, 2011.

Nyberg et al., Growth hormone and its receptors in the central nervous system—location and functional significance. Horm Res. 1996;45(1-2):18-22.

Pacold et al., Biologically active pituitary hormones in the rat brain amygdaloid nucleus. Science. Feb. 17, 1978;199(4330):804-6.

Pardridge, The blood-brain barrier: bottleneck in brain drug development. NeuroRx. Jan. 2005;2(1):3-14.

Ransome et al., Growth hormone signaling and hippocampal neurogenesis: insights from genetic models. Hippocampus. 2008;18(10):1034-50. doi: 10.1002/hipo.20463.

(56) References Cited

OTHER PUBLICATIONS

Raybuck et al., Double dissociation of amygdala and hippocampal contributions to trace and delay fear conditioning. PLoS One. Jan. 19, 2001;6(1):e15982. doi: 10.1371/journal.pone.0015982.
Rivera et al., Long-term regulated expression of growth hormone in mice after intramuscular gene transfer. Proc Natl Acad Sci U S A. Jul. 20, 1999;96(15):8657-62.
Sun et al., Local expression of GH and IGF-1 in the hippocampus of GHh-deficient long-lived mice. Neurobiol Aging. Jun. 2005;26(6):929-37.
Telegdy et al., Neurotransmitter-mediated action of an antagonist of growth hormone-releasing hormone on anxiolysis in mice. Behav Brain Res. Jul. 15, 2012;233(1):232-6. doi: 10.1016/j.bbr.Apr. 11, 2012. Epub May 5, 2012.
Treacy et al., Functional glucocorticoid inducible enhancer activity in the 5'-flanking sequences of the rat growth hormone gene. J Steroid Biochem Mol Biol. Jan. 1991;38(1):1-15.
Valvassori et al., Contributions of animal models to the study of mood disorders. Rev Bras Psiquiatr. 2013;35 Suppl 2:S121-31. doi: 10.1590/1516-4446-2013-1168.
Vander Weele et al., Restoration of hippocampal growth hormone reverses stress-induced hippocampal impairment. Front Behav Neurosci. Jun. 14, 2013;7:66. doi: 10.3389/fnbeh.2013.00066. eCollection 2013.
Varga et al., Synthesis and biological evaluation of antagonists of growth hormone-releasing hormone with high and protracted in vivo activities. Proc Natl Acad Sci U S A. Jan. 19, 1999;96(2):692-7.
Vyas et al., Chronic stress induces contrasting patterns of dendritic remodeling in hippocampal and amygdaloid neurons. J Neurosci. Aug. 1, 2002;22(15):6810-8.
Wanisch et al., Tackling obstacles for gene therapy targeting neurons: disrupting perineural nets with hyaluronidase improves transduction. PLoS One. 2013;8(1):e53269. doi: 10.1371/journal.pone.0053269. Epub Jan. 3, 2013.
Albarran-Zeckler et al., Growth hormone secretagogue receptor (GHS-R1 a) knockout mice exhibit improved spatial memory and deficits in contextual memory. Behav Brain Res. Jun. 15, 2012;232(1):13-9. doi:10.1016/j.bbr.Mar. 12, 2012. Epub Mar. 31, 2012.
Alvarez-Crespo et al., The amygdala as a neurobiological target for ghrelin in rats: neuroanatomical, electrophysiological and behavioral evidence. PLoS One. 2012;7(10):e46321. doi: 10.1371/journal.pone.0046321. Epub Oct. 10, 2012.
Andero et al., Amygdala-dependent fear is regulated by Oprl1 in mice and humans with PTSD. Sci Transl Med. Jun. 5, 2013;5(188):188ra73. doi: 10.1126/scitranslmed.3005656.
Bednarek et al., Structure-function studies on the new growth hormone-releasing peptide, ghrelin: minimal sequence of ghrelin necessary for activation of growth hormone secretagogue receptor 1a. J Med Chem. Nov. 16, 2000;43(23):4370-6.
Belanoff et al., Cortisol activity and cognitive changes in psychotic major depression. Am J Psychiatry. Oct. 2001;158(10):1612-6.
Betley et al., Neurons for hunger and thirst transmit a negative-valence teaching signal. Nature. May 14, 2015;521(7551):180-5. doi: 10.1038/nature14416. Epub Apr. 27, 2015.
Birzniece et al., Growth hormone receptor modulators. Rev Endocr Metab Disord. Jun. 2009;10(2):145-56. doi: 10.1007/s11154-008-9089-x.
Bramham et al., BDNF function in adult synaptic plasticity: the synaptic consolidation hypothesis. Prog Neurobiol. Jun. 2005;76(2):99-125.
Briggs et al., Evidence that diet-induced hyperleptinemia, but not hypothalamic gliosis, causes ghrelin resistance in NPY/AgRP neurons of male mice. Endocrinology. Jul. 2014;155(7):2411-22. doi:10.1210/en.2013-1861. Epub Apr. 17, 2014.
Brioni et al., Involvement of the amygdala GABAergic system in the modulation of memory storage. Brain Res. May 15, 1989;487(1):105-12.

Cahill et al., Amygdala activity at encoding correlated with long-term, free recall of emotional information. Proc Natl Acad Sci U S A. Jul. 23, 1996;93(15):8016-21.
Carlini et al., Differential role of the hippocampus, amygdala, and dorsal raphe nucleus in regulating feeding, memory, and anxiety-like behavioral responses to ghrelin. Biochem Biophys Res Commun. Jan. 16, 2004;313(3):635-41.
Carlini et al., Ghrelin increases anxiety-like behavior and memory retention in rats. Biochem Biophys Res Commun. Dec. 20, 2002;299(5):739-43.
Carvajal et al., Central ghrelin increases anxiety in the Open Field test and impairs retention memory in a passive avoidance task in neonatal chicks. Neurobiol Learn Mem. May 2009;91(4):402-7. doi: 10.1016/j.nlm.Dec. 8, 2008. Epub Jan. 31, 2009.
Castellano et al., Interaction of beta-endorphin and GABAergic drugs in the regulation of memory storage. Behav Neural Biol. Sep. 1993;60(2):123-8.
Chen et al., Rapid loss of dendritic spines after stress involves derangement of spine dynamics by corticotropin-releasing hormone. J Neurosci. Mar. 12, 2008;28(11):2903-11. doi: 10.1523/JNEUROSCI.0225-08.2008.
Clark et al., Long-acting growth hormones produced by conjugation with polyethylene glycol. J Biol Chem. Sep. 6, 1996;271(36):21969-77.
Codner et al., Effects of oral administration of ibutamoren mesylate, a nonpeptide growth hormone secretagogue, on the growth hormone-insulin-like growth factor I axis in growth hormone-deficient children. Clin Pharmacol Ther. Jul. 2001;70(1):91-8.
Cook et al., The pharmacokinetic and pharmacodynamic characteristics of a long-acting growth hormone (GH) preparation (nutropin depot) in GhH-deficient adults. J Clin Endocrinol Metab. Oct. 2002;87(10):4508-14.
Cordero et al., A role for brain glucocorticoid receptors in contextual fear conditioning: dependence upon training intensity. Brain Res. Mar. 9, 1998;786(1-2):11-7.
Cowley et al., The distribution and mechanism of action of ghrelin in the CNS demonstrates a novel hypothalamic circuit regulating energy homeostasis. Neuron. Feb. 20, 2003;37(4):649-61.
Cummings et al., A preprandial rise in plasma ghrelin levels suggests a role in meal initiation in humans. Diabetes. Aug. 2001;50(8):1714-9.
Dietrich et al., Hypothalamic Agrp neurons drive stereotypic behaviors beyond feeding. Cell. Mar. 12, 2015;160(6):1222-32. doi:10.1016/j.cell.Feb. 24, 2015. Epub Mar. 5, 2015.
Dudai, The neurobiology of consolidations, or, how stable is the engram? Annu Rev Psychol. 2004;55:51-86.
Finsterwald et al., Stress and glucocorticoid receptor-dependent mechanisms in long-term memory: from adaptive responses to psychopathologies. Neurobiol Learn Mem. Jul. 2014;112:17-29. doi: 10.1016/j.nlm.Sep. 17, 2013. Epub Oct. 7, 2013.
Fumoto et al., Targeted Gene Delivery. Importance of Administration Routes. Intech. 2013;3-13.
Garin et al., Clinical review: The human experience with ghrelin administration. J Clin Endocrinol Metab. May 2013;98(5):1826-37. doi: 10.1210/jc.2012-4247. Epub Mar. 26, 2013.
Ghersi et al., Ghrelin increases memory consolidation through hippocampal mechanisms dependent on glutamate release and NR2B-subunits of the NMDA receptor. Psychopharmacology (Berl). May 2015;232(10):1843-57. doi:10.1007/s00213-014-3817-6. Epub Dec. 4, 2014.
Goldstone et al., Ghrelin mimics fasting to enhance human hedonic, orbitofrontal cortex, and hippocampal responses to food. Am J Clin Nutr. Jun. 2014;99(6):1319-30. doi: 10.3945/ajcn.113.075291. Epub Apr. 23, 2014.
Guan et al., Distribution of mRNA encoding the growth hormone secretagogue receptor in brain and peripheral tissues. Brain Res Mol Brain Res. Aug. 1997;48(1):23-9.
Hansson et al., Influence of ghrelin on the central serotonergic signaling system in mice. Neuropharmacology. Apr. 2014;79:498-505. doi: 10.1016/j.neuropharm.Dec. 12, 2013.

(56) References Cited

OTHER PUBLICATIONS

Harrison et al., Exploring the Structure of Human Defensive Responses from Judgments of Threat Scenarios. PLoS One. Aug. 21, 2015;10(8):e0133682. doi: 10.1371/journal.pone.0133682. eCollection 2015.
Holbrook et al., Morphine use after combat injury in Iraq and post-traumatic stress disorder. N Engl J Med. Jan. 14, 2010;362(2):110-7. doi: 10.1056/NEJMoa0903326.
Hui et al., Memory enhancement of classical fear conditioning by post-training injections of corticosterone in rats. Neurobiol Learn Mem. Jan. 2004;81(1):67-74.
Jacks et al., MK-0677, a potent, novel, orally active growth hormone (GH) secretagogue: GH, insulin-like growth factor I, and other hormonal responses in beagles. Endocrinology. Dec. 1996;137(12):5284-9.
Jasnow et al., Thy1-expressing neurons in the basolateral amygdala may mediate fear inhibition. J Neurosci. Jun. 19, 2013;33(25):10396-404. doi:10.1523/JNEUROSCI.5539-12.2013.
Jeneson et al., Working memory, long-term memory, and medial temporal lobe function. Learn Mem. Dec. 16, 2011;19(1):15-25. doi: 10.1101/1m.024018.111. Print Jan. 2012.
Jostel et al., A new sustained-release preparation of human growth hormone and its pharmacokinetic, pharmacodynamic and safety profile. Clin Endocrinol (Oxf). May 2005;62(5):623-7.
Juster et al., A transdisciplinary perspective of chronic stress in relation to psychopathology throughout life span development. Dev Psychopathol. Aug. 2011;23(3):725-76. doi: 10.1017/S0954579411000289.
Krishnan et al., Linking molecules to mood: new insight into the biology of depression. Am J Psychiatry. Nov. 2010;167(11):1305-20. doi:10.1176/appi.ajp.2009.10030434. Epub Sep. 15, 2010.
Kumar et al., Differential effects of chronic social stress and fluoxetine on meal patterns in mice. Appetite. May 2013;64:81-8. doi:10.1016/j.appet.Dec. 23, 2012. Epub Jan. 11, 2013.
Lee et al., Sampling blood from the lateral tail vein of the rat. J Vis Exp. May 18, 2015;(99):e52766. doi: 10.3791/52766.
Lockie et al., Diet-induced obesity causes ghrelin resistance in reward processing tasks. Psychoneuroendocrinology. Dec. 2015;62:114-20. doi: 10.1016/j.psyneuen.Aug. 4, 2015. Epub Aug. 11, 2015.
Lutter et al., The orexigenic hormone ghrelin defends against depressive symptoms of chronic stress. Nat Neurosci. Jul. 2008;11(7):752-3. doi: 10.1038/nn.2139. Epub Jun. 15, 2008.
Marin et al., Metyrapone administration reduces the strength of an emotional memory trace in a long-lasting manner. J Clin Endocrinol Metab. Aug. 2011;96(8):E1221-7. doi: 10.1210/jc.2011-0226. Epub May 18, 2011.
McIntyre et al., Amygdala norepinephrine levels after training predict inhibitory avoidance retention performance in rats. Eur J Neurosci. Oct. 2002;16(7):1223-6.
Nass et al., Effects of an oral ghrelin mimetic on body composition and clinical outcomes in healthy older adults: a randomized trial. Ann Intern Med. Nov. 4, 2008;149(9):601-11.
Natalucci et al., Spontaneous 24-h ghrelin secretion pattern in fasting subjects: maintenance of a meal-related pattern. Eur J Endocrinol. Jun. 2005;(6):845-50.
Parsons et al., Implications of memory modulation for post-traumatic stress and fear disorders. Nat Neurosci. Feb. 2013;16(2):146-53. doi:10.1038/nn.3296. Epub Jan. 28, 2013.
Reiter et al., A multicenter study of the efficacy and safety of sustained release GH in the treatment of naive pediatric patients with GhH deficiency. J Clin Endocrinol Metab. Oct. 2001;86(10):4700-6.
Ribeiro et al., Ghrelin triggers the synaptic incorporation of AMPA receptors in the hippocampus. Proc Natl Acad Sci U S A. Jan. 7, 2014;111(1):E149-58. doi:10.1073/pnas.1313798111. Epub Dec. 23, 2013.
Schellekens et al., Promiscuous dimerization of the growth hormone secretagogue receptor (GHS-R1 a) attenuates ghrelin-mediated signaling. J Biol Chem. Jan. 4, 2013;288(1):181-91. doi: 10.1074/jbc.M112.382473.
Schellekens et al., Taking two to tango: a role for ghrelin receptor heterodimerization in stress and reward. Front Neurosci. Aug. 30, 2013;7:148. doi: 10.3389/fnins.2013.00148.
Shors et al., Sex differences and opposite effects of stress on dendritic spine density in the male versus female hippocampus. J Neurosci. Aug. 15, 2001;21(16):6292-7.
Sivertsen et al., Functionally biased signaling properties of 7TM receptors—opportunities for drug development for the ghrelin receptor. Br J Pharmacol. Dec. 2013;170(7):1349-62. doi: 10.1111/bph.12361.
Song et al., Ghrelin modulates lateral amygdala neuronal firing and blocks acquisition for conditioned taste aversion. PLoS One. Jun. 7, 2013;8(6):e65422. doi:10.1371/journal.pone.0065422. Print 2013.
Spencer et al., Ghrelin regulates the hypothalamic-pituitary-adrenal axis and restricts anxiety after acute stress. Biol Psychiatry. Sep. 15, 2012;72(6):457-65. doi: 10.1016/j.biopsych.Mar. 10, 2013. Epub Apr. 21, 2013.
Spencer et al., Ghrelin's Role in the Hypothalamic-Pituitary-Adrenal Axis Stress Response: Implications for Mood Disorders. Biol Psychiatry. Jul. 1, 2015;78(1):19-27. doi:10.1016/j.biopsych.Oct. 21, 2014. Epub Oct. 31, 2014.
Tibshirani, Regression shrinkage and selection via the lasso. J R Stat Soc: Ser B (Method) 1996;58(1):267-288.
Tolle et al., Ultradian rhythmicity of ghrelin secretion in relation with GH, feeding behavior, and sleep-wake patterns in rats. Endocrinology. Apr. 2002;143(4):1353-61.
Tronson et al., Molecular mechanisms of memory reconsolidation. Nat Rev Neurosci. Apr. 2007;8(4):262-75.
Tschöp et al., Ghrelin induces adiposity in rodents. Nature. Oct. 19, 2000;407(6806):908-13.
Vaiva et al., Low posttrauma GABA plasma levels as a predictive factor in the development of acute posttraumatic stress disorder. Biol Psychiatry. Feb. 1, 2004;55(3):250-4.
Warner-Schmidt et al., Hippocampal neurogenesis: opposing effects of stress and antidepressant treatment. Hippocampus. 2006;16(3):239-49.
Wilensky et al., Functional inactivation of the amygdala before but not after auditory fear conditioning prevents memory formation. J Neurosci. Dec. 15, 2009;19(24):RC48.
Wren et al., Ghrelin enhances appetite and increases food intake in humans. J Clin Endocrinol Metab. Dec. 2001;86(12):5992.
Zarouna et al., Mood disorders: A potential link between ghrelin and leptin on human body? World J Exp Med. May 20, 2015;5(2):103-9. doi: 10.5493/wjem.v5.i2.103. eCollection May 20, 2015.
Zearfoss et al., A molecular circuit composed of CPEB-1 and c-Jun controls growth hormone-mediated synaptic plasticity in the mouse hippocampus. J Neurosci. Aug. 20, 2008;28(34):8502-9. 10.1523/JNEUROSCI.1756-08.2008.
Arafat et al., Glucagon inhibits ghrelin secretion in humans. Eur J Endocrinol. Sep. 2005;153(3):397-402.
Banasch et al., Glucagon-like peptide 2 inhibits ghrelin secretion in humans. Regul Pept. Dec. 10, 2006;137(3):173-8. Epub Aug. 22, 2006.
Banks et al., Extent and direction of ghrelin transport across the blood-brain barrier is determined by its unique primary structure. J Pharmacol Exp Ther. Aug. 2002;302(2):822-7.
Davies et al., Origins and evolution of antibiotic resistance. Microbiol Mol Biol Rev. Sep. 2010;74(3):417-33. doi: 10.1128/MMBBR.00016-10.
De Vriese et al., Ghrelin degradation by serum and tissue homogenates: identification of the cleavage sites. Endocrinology. Nov. 2004;145(11):4997-5005. Epub Jul. 15, 2004.
Dienes et al., The stress sensitization hypothesis: understanding the course of bipolar disorder. J Affect Disord. Oct. 2006;95(1-3):43-9. Epub Jul. 11, 2006.
Dogrukol-Ak et al., Isolation of peptide transport system-6 from brain endothelial cells: therapeutic effects with antisense inhibition

(56) References Cited

OTHER PUBLICATIONS in Alzheimer and stroke models. J Cereb Blood Flow Metab. Feb. 2009;29(2):411-22. doi: 10.1038/jcbfm.2008.131. Epub Nov. 12, 2008.
Ellicott et al., Life events and the course of bipolar disorder. Am J Psychiatry. Sep. 1990;147(9):1194-8.
Foust et al., Intravascular AAV9 preferentially targets neonatal neurons and adult astrocytes. Nat Biotechnol. Jan. 2009;27(1):59-65. doi: 10.1038/nbt.1515. Epub Dec. 21, 2008.
Gold et al., Organization of the stress system and its dysregulation in melancholic and atypical depression: high vs low CRH/NE states. Mol Psychiatry. 2002;7(3):254-75.
Guardiola-Lemaitre et al., Agomelatine: mechanism of action and pharmacological profile in relation to antidepressant properties. Br J Pharmacol. Aug. 2014;171(15):3604-19. doi:10.1111/bph.12720.
Hagemann et al., Glucagon-like peptide 1 (GLP-1) suppresses ghrelin levels in humans via increased insulin secretion. Regul Pept. Oct. 4, 2007;143(1-3):64-8. Epub Mar. 20, 2007.
Huang et al., Efficient gene delivery targeted to the brain using a transferrin-conjugated polyethyleneglycol-modified polyamidoamine dendrimer. FASEB J. Apr. 2007;21(4):1117-25. Epub Jan. 11, 2007.
Liu et al., Brain-targeting gene delivery and cellular internalization mechanisms for modified rabies virus glycoprotein RVG29 nanoparticles. Biomaterials. Sep. 2009;30(25):4195-202. doi:10.1016/j.biomaterials.2009.02.051. Epub May 20, 2009.
Mancuso et al., Paradoxical reactions to benzodiazepines: literature review and treatment options. Pharmacotherapy. Sep. 2004;24(9):1177-85.
Mayorov et al., Catalytic antibody degradation of ghrelin increases whole-body metabolic rate and reduces refeeding in fasting mice. Proc Natl Acad Sci U S A. Nov. 11, 2008;105(45):17487-92. doi: 10.1073/pnas.0711808105. Epub Nov. 3, 2008.
Ohara et al., Rates and risk of postpartum depression—a meta-analysis. Int Rev Psych. 1996;8(1):37-54.
Pardridge, Drug transport across the blood-brain barrier. J Cereb Blood Flow Metab. Nov. 2012;32(11):1959-72. doi: 10.1038/jcbfm.2012.126. Epub Aug. 29, 2012.
Robertson et al., Antenatal risk factors for postpartum depression: a synthesis of recent literature. Gen Hosp Psychiatry. Jul.-Aug. 2004;26(4):289-95.
Santarelli et al., Requirement of hippocampal neurogenesis for the behavioral effects of antidepressants. Science. Aug. 8, 2003;301(5634):805-9.
Siegrist, Chronic psychosocial stress at work and risk of depression:evidence from prospective studies. Eur Arch Psychiatry Clin Neurosci. Nov. 2008;258 Suppl 5:115-9. doi: 10.1007/s00406008-5024-0.
Yao et al., Unexpected Reaction Pathway for butyrylcholinesterase-catalyzed inactivation of "hunger hormone" ghrelin. Sci Rep. Feb. 29, 2016;6:22322. doi: 10.1038/srep22322.
Zhang et al., Drug delivery strategies to enhance the permeability of the blood-brain barrier for treatment of glioma. Drug Des Devel Ther. Apr. 9, 2015;9:2089-100. doi: 10.2147/DDDT.S79592. eCollection 2015.
Zhao et al., Ghrelin secretion stimulated by {beta }1-adrenergic receptors in cultured ghrelinoma cells and in fasted mice. Proc Natl Acad Sci U S A. Sep. 7, 2010;107(36):15868-73. doi: 10.1073/pnas.1011116107. Epub Aug. 16, 2010.
Bernstein et al., Symptom features of postpartum depression: are they distinct? Depress Anxiety. 2008;25(1):20-6.
Bloch et al., Effects of gonadal steroids in women with a history of postpartum depression. Am J Psychiatry. Jun. 2000;157(6):924-30.
Bloch et al., Endocrine factors in the etiology of postpartum depression. Compr Psychiatry. May-Jun. 2003;44(3):234-46.
Kearns et al., Early interventions for PTSD: a review. Depress Anxiety. Oct. 2012;29(10):833-42. doi: 10.1002/da.21997. Epub Aug. 31, 2012.
Shanks et al., Are animal models predictive for humans? Philos Ethics Humanit Med. Jan. 15, 2009;4:2. doi: 10.1186/1747-5341-4-2.

* cited by examiner

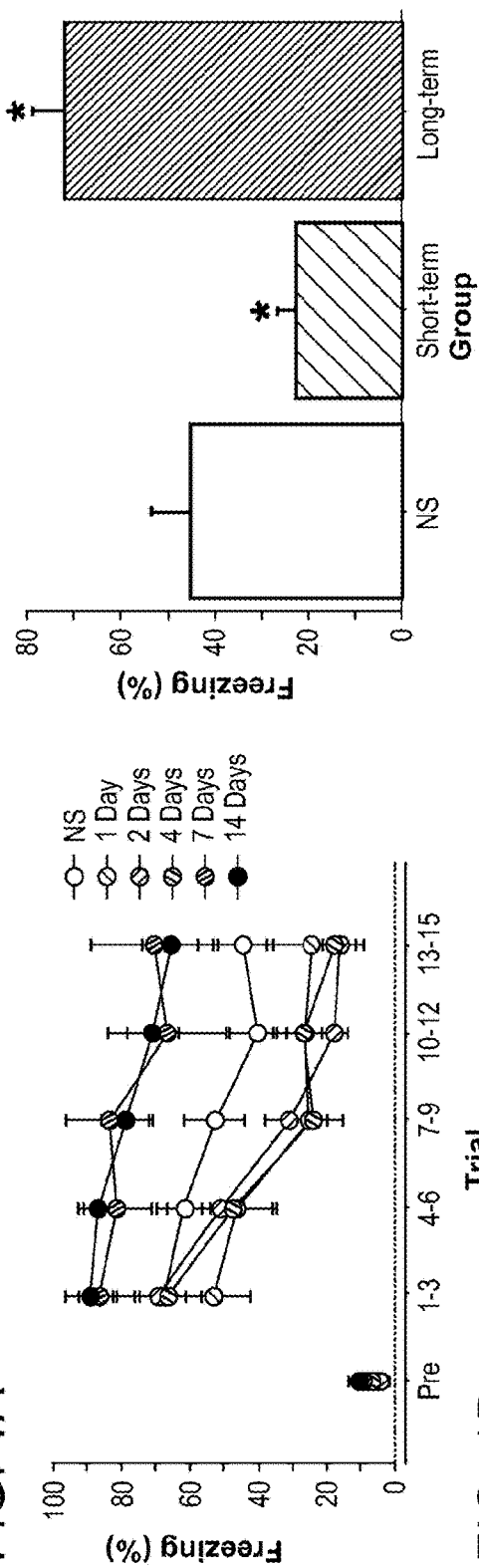
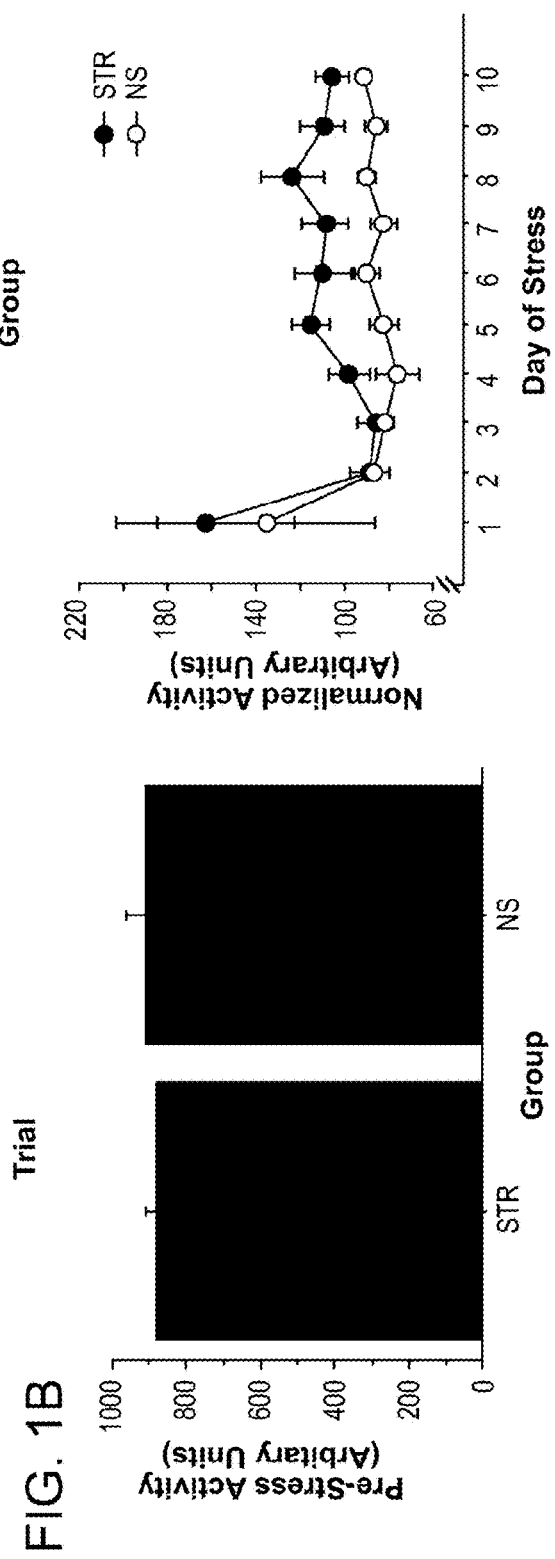
FIG. 1A
FIG. 1B

Chronic and acute stress have different effects

What underlies chronic stress-induced vulnerability to excessive fear?

What underlies chronic stress-induced vulnerability to excessive fear?

Repeated activation of ghrelin receptor is SUFFICIENT for vulnerability to fear

Repeated activation of ghrelin receptors in AMYGDALA is sufficient to produce vulnerability to fear Activation of the ghrelin receptor is NECESSARY for
stress-induced vulnerability to excessive fear

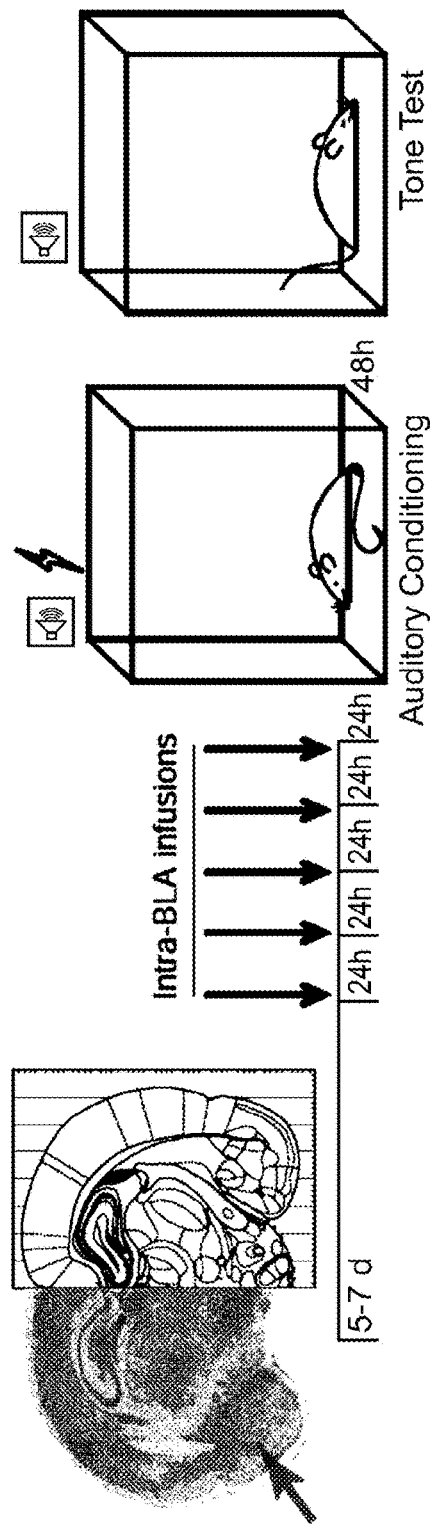
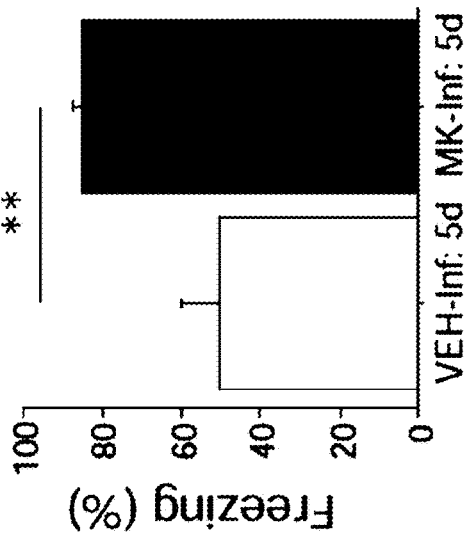
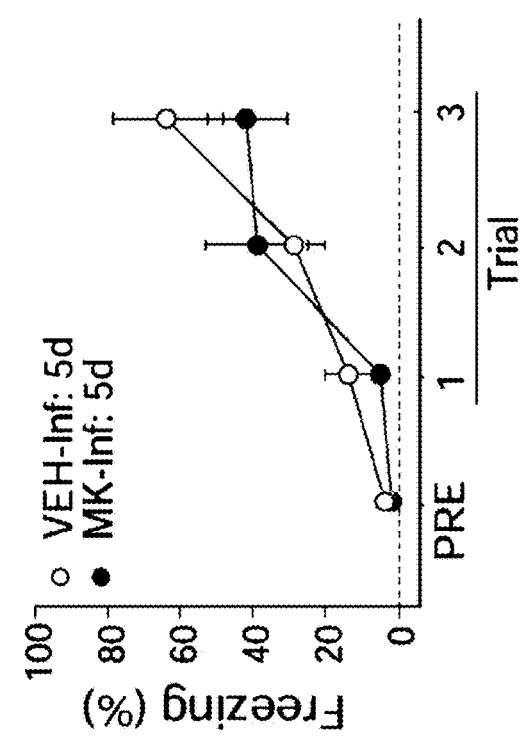
FIG. 10
FIG. 10A
FIG. 10B

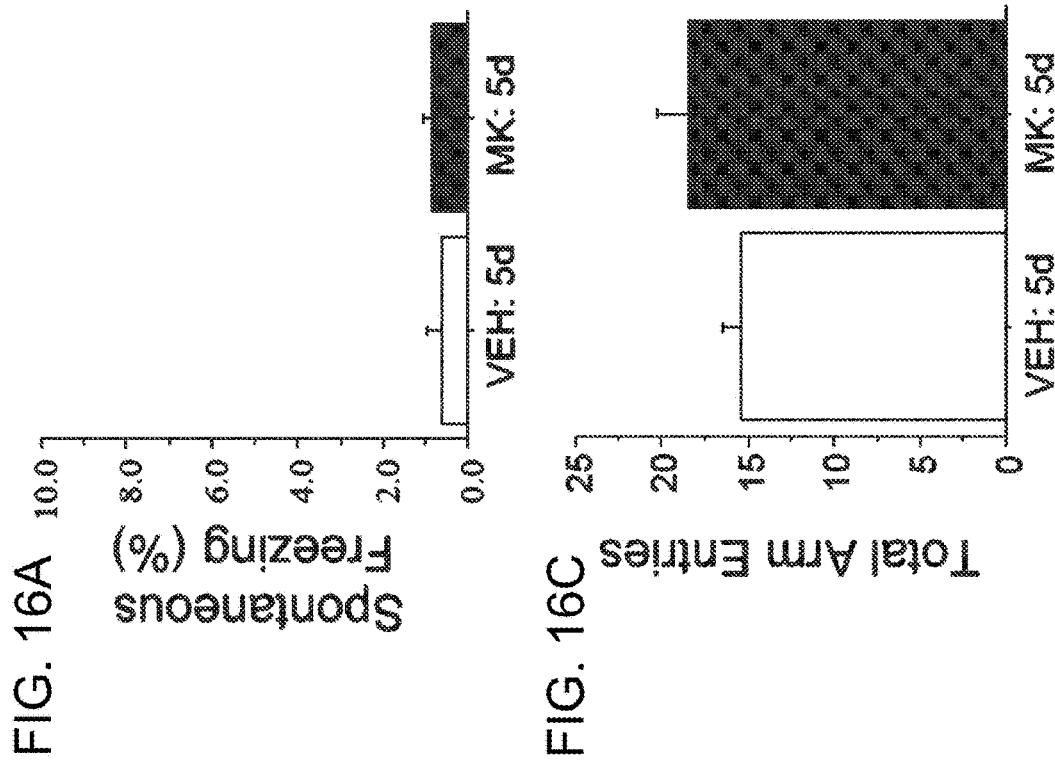

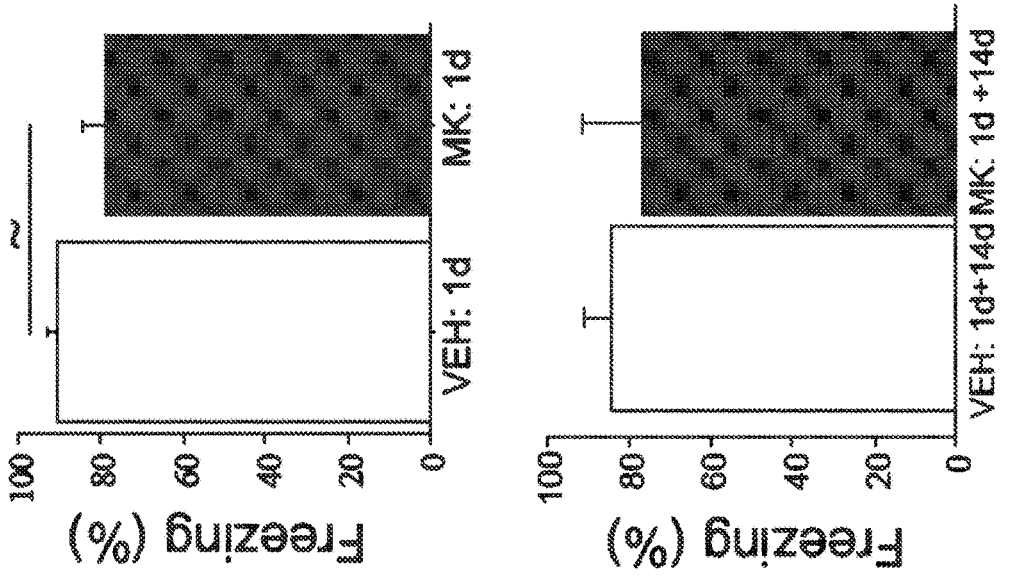
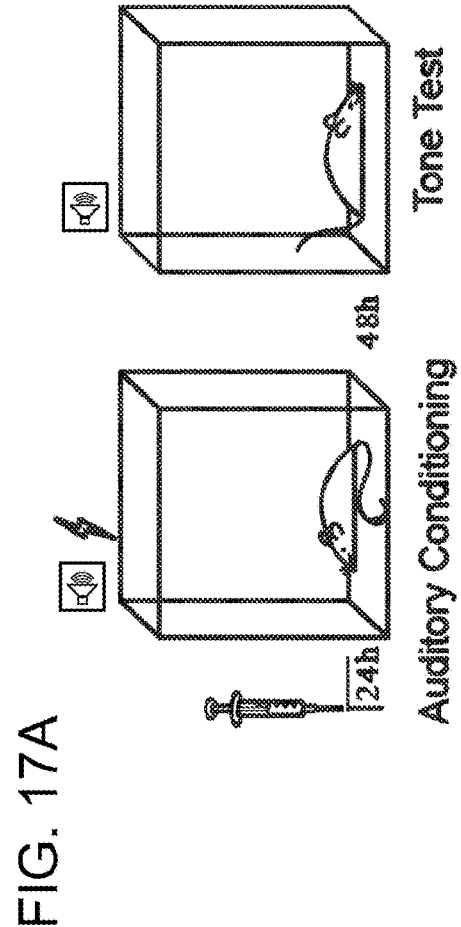
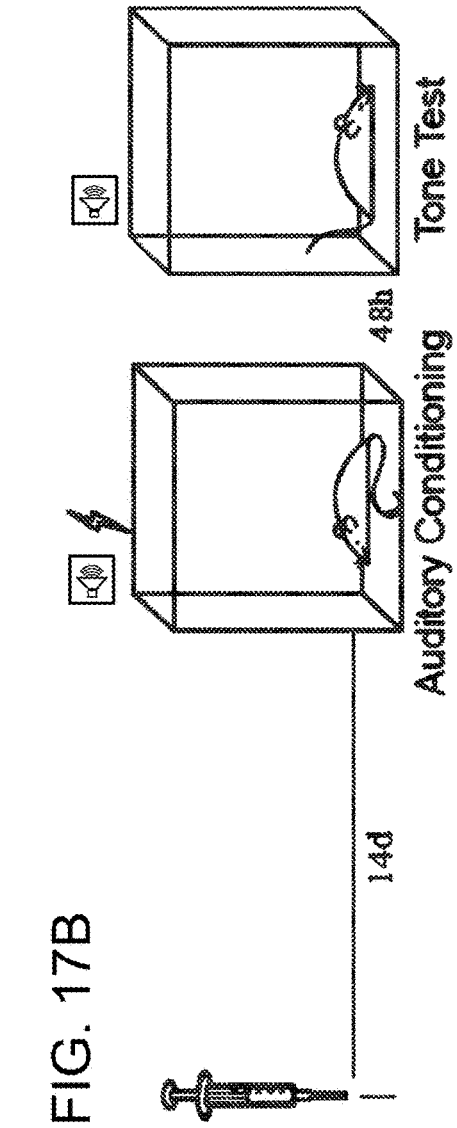
FIG. 17A
FIG. 17B

USE OF ANTAGONISTS OF GHRELIN OR GHRELIN RECEPTOR TO PREVENT OR TREAT STRESS-SENSITIVE PSYCHIATRIC ILLNESS

RELATED APPLICATIONS

This application is a national stage filing under U.S.C. § 371 of PCT International Application PCT/US2013/025130 filed Feb. 7, 2013, which claims priority under 35 U.S.C. § 119 to U.S. provisional patent application U.S. Ser. No. 61/595,845, filed Feb. 7, 2012, entitled "USE OF ANTAGONISTS OF GHRELIN OR GHRELIN RECEPTOR TO PREVENT OR TREAT STRESS-SENSITIVE PSYCHIATRIC ILLNESS" the entire contents of which is incorporated herein by reference.

GOVERNMENT INTEREST

This invention was made with government support under Grant No. R01 MH084966 awarded by the National Institutes of Health and under Grant No. W911NF-10-1-0059 awarded by the Army Research Office. The government has certain rights in this invention.

FIELD OF THE INVENTION

The invention relates to antagonism of ghrelin or ghrelin receptor to protect against, treat or prevent disorders associated with chronic stress.

BACKGROUND INFORMATION

Ghrelin is a peptide hormone produced primarily by gastrointestinal cells. Receptors for ghrelin are highly expressed in regions of the hypothalamus that control feeding. Accordingly, ghrelin has been extensively studied for its ability to induce feeding behavior. However, ghrelin receptors are also expressed in other brain regions not traditionally associated with feeding behavior, such as the hippocampus. Ghrelin signaling is linked to obesity, diabetes and cardiovascular function. It has also been reported that increasing the levels of ghrelin leads to anti-depressant effects and that mice carrying a null mutation in the ghrelin receptor have increased depressive symptoms, suggesting that active ghrelin signaling has anti-depressant activity (13).

SUMMARY OF INVENTION

Here, it is surprisingly shown that ghrelin, in fact, enhances, rather than ameliorates, the deleterious effects of chronic stress. Ghrelin was found to be both necessary and sufficient for stress-induced vulnerability to excessive fear. Accordingly, in contrast to previous reports, antagonizing, rather than activating ghrelin signaling, is desirable for combating stress-related symptoms.

Aspects of the invention relate to methods of protecting against chronic stress in a subject in need thereof, including administering to the subject a therapeutically effective amount of an agent that inhibits the level or activity of ghrelin or ghrelin receptor. In some embodiments, the agent is administered before, during and/or after exposure of the subject to chronic stress.

In some embodiments, the agent targets the ghrelin receptor. In certain embodiments, the agent is a GHSr1a antagonist or a GHSr1a inverse agonist. In some embodiments, the agent targets ghrelin. In certain embodiments, the agent is an anti-ghrelin vaccine. In other embodiments, the agent targets ghrelin O-acyltransferase (GOAT). In certain embodiments, the agent is an anti-GOAT vaccine. In other embodiments, the agent is a compound that reduces or inhibits the synthesis or release of ghrelin by the stomach. In other embodiments, the agent is a compound that reduces or prevents ghrelin from crossing the blood-brain barrier. In other embodiments the treatment involves reducing levels in circulation using agents that inactivate (deacylate) ghrelin or by agents that increase plasma esterases responsible for endogenous ghrelin deacylation, such as APT1 and other putative esterases. Thus, esterases such as APT1 are agents targeting ghrelin or the ghrelin receptor according to the invention.

In some embodiments, the chronic stress is associated with military service or a natural disaster. In some embodiments, the chronic stress is associated with low socioeconomic status. In some embodiments, the chronic stress is associated with acutely traumatic experiences.

Further aspects of the invention relate to methods of treating a stress-sensitive disorder in a subject exposed to chronic stress, including administering to the subject a therapeutically effective amount of an agent that inhibits the level or activity of ghrelin or ghrelin receptor. In some embodiments, the stress-sensitive disorder is post-traumatic stress disorder (PTSD), depressive disorder, major depressive disorders, bipolar disorder, acute stress disorder, generalized anxiety disorder, obsessive-compulsive disorder, schizophrenia, panic disorders or trichotillomania. In some embodiments, the agent is administered before, during and/or after exposure of the subject to chronic stress. In some embodiments, the stress-sensitive disorder is not schizophrenia.

In some embodiments, the agent targets the ghrelin receptor. In certain embodiments, the agent is a GHSr1a antagonist or a GHSr1a inverse agonist. In some embodiments, the agent targets ghrelin. In certain embodiments, the agent is an anti-ghrelin vaccine. In other embodiments, the agent targets ghrelin O-acyltransferase (GOAT). In certain embodiments, the agent is an anti-GOAT vaccine. In other embodiments, the agent is a compound that reduces or inhibits the synthesis or release of ghrelin by the stomach. In other embodiments, the agent is a compound that reduces or prevents ghrelin from crossing the blood-brain barrier. In some embodiments, the chronic stress is associated with military service or a natural disaster. In some embodiments the subject is not overweight or obese.

Further aspects of the invention relate to methods for determining whether a subject exposed to chronic stress has an increased risk of developing a stress-sensitive disorder, including conducting an assay to measure the ghrelin levels in the subject after the subject has been exposed to chronic stress, wherein elevation of ghrelin levels in the subject after the subject has been exposed to chronic stress relative to normal ghrelin levels indicates that the subject has an increased risk of developing a stress-sensitive disorder.

In some embodiments, normal ghrelin levels correspond to ghrelin levels in the subject prior to exposure to chronic stress. In some embodiments, ghrelin levels are measured at multiple time points after the subject has been exposed to chronic stress to detect long-term elevation of ghrelin levels. In some embodiments, the assay is performed on a blood sample from the subject. In some embodiments, if the subject has elevated ghrelin levels after exposure to chronic stress, then the subject is administered a therapeutically effective amount of an agent that inhibits the level or activity of ghrelin or ghrelin receptor.

In some embodiments, the stress-sensitive disorder is post-traumatic stress disorder (PTSD), depressive disorder, major depressive disorders, bipolar disorder, acute stress disorder, generalized anxiety disorder, obsessive-compulsive disorder, panic disorders, schizophrenia or trichotillomania.

In some embodiments, the agent targets the ghrelin receptor. In certain embodiments, the agent is a GHSr1a antagonist or a GHSr1a inverse agonist. In some embodiments, the agent targets ghrelin. In certain embodiments, the agent is an anti-ghrelin vaccine. In other embodiments, the agent targets ghrelin O-acyltransferase (GOAT). In certain embodiments, the agent is an anti-GOAT vaccine. In other embodiments, the agent is a compound that reduces or inhibits the synthesis or release of ghrelin by the stomach. In other embodiments, the agent is a compound that reduces or prevents ghrelin from crossing the blood-brain barrier. In some embodiments, the chronic stress is associated with military service or a natural disaster.

These and other aspects of the invention, as well as various embodiments thereof, will become more apparent in reference to the drawings and detailed description of the invention.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 shows that acute and chronic stressors produce differential effects. A) Rats were administered a psychological stressor (4 h/day) for periods of time ranging from one day (acute stress) to 14 days (STR groups). A control group was given daily handling (No Stress group; NS). After the final stress or handling session, all rats were subjected to auditory fear conditioning, and fear to the auditory cue was subsequently assessed. Fear memory was enhanced by stress only for stressors of 7 or more days in duration. Shorter periods of stress had the opposite effect: an impairment of fear memory. B) Rats were implanted with small devices (e-mitters; Respironics, Bend, Oreg.) that permitted constant monitoring of activity and body temperature. After recovery, rats were administered a psychological stressor (4 h/day; STR group) or received daily handling (NS group) for 10 days. Activity was assessed for the 6 h period following the daily stressor or handling session. Rats in the STR group displayed a gradual enhancement of activity in their home cages following the stressor; no change was observed in the NS group.

FIG. 10 shows that long-term pharmacological stimulation of ghrelin receptor activity in the amygdala enhances fear memory. Rats were implanted with bilateral cannulae aimed at the basolateral amygdala (BLA). The arrow indicates the tip of the injector within a representative coronal brain section. Following recovery, intra-BLA infusions of either MK-0677 (MK-Inf: 5 d) or aCSF (VEH-Inf: 5 d) were administered daily for five consecutive days and, 24 h following the final infusion, (a) auditory fear conditioning was administered. (b) Fear memory was assessed in a novel context 48 h following fear conditioning. Brain illustration adapted from (45). All data are mean±s.e.m. * p<0.05, ** p<0.01, ~p<0.10 in planned comparisons.

FIG. 17 shows that single injections of ghrelin receptor agonist are not sufficient to enhance fear. (a) Rats received a single injection of saline (vehicle, VEH: 1 d) or MK-0677 (MK: 1 d) and received Pavlovian Auditory Fear Conditioning 24 h later. Fear to the tone was assessed 48 h after fear conditioning. (b) Rats received a single injection of saline (vehicle, VEH: 1 d+14 d) or MK-0677 (MK: 1 d+14 d) and were then returned to the vivarium for 14 d before receiving auditory Pavlovian fear conditioning. Fear to the tone was assessed 48 h later. All data are mean±s.e.m. ~p<0.10 in planned comparisons.

DETAILED DESCRIPTION

Figure 2C:
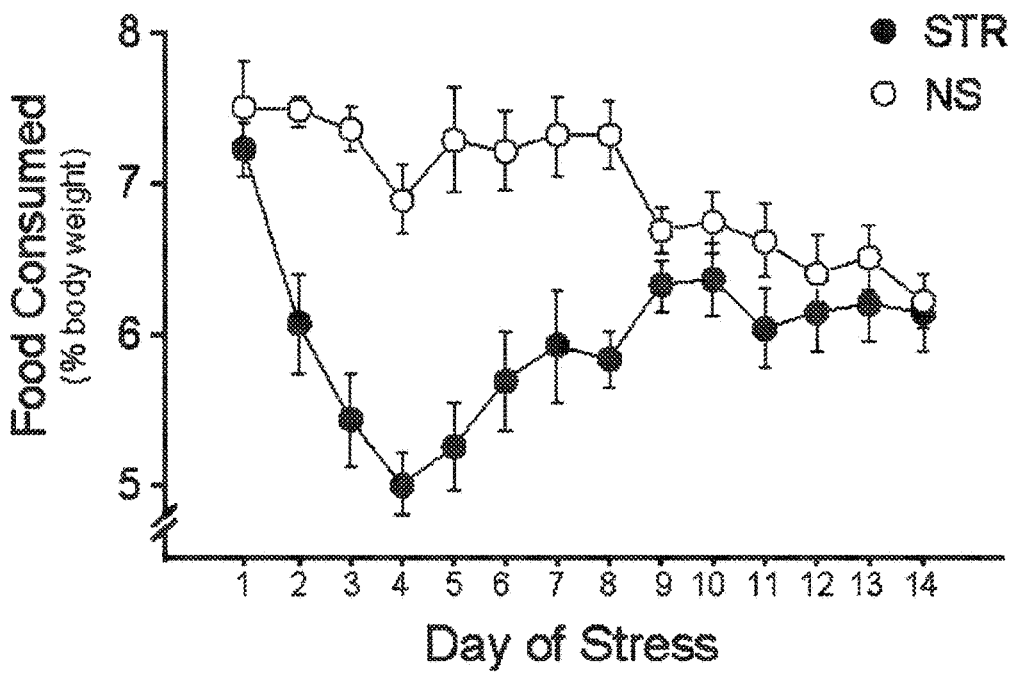
FIG. 2 further shows differential effects of chronic vs. acute stress. C) Rats were administered a psychological stressor (4 h/day) for periods of time ranging from one day (acute stress) to 14 days (STR groups). A control group was given daily handling (No Stress group; NS). Food consumption and body weight were assessed daily. Stress produced an immediate drop in body weight and food consumption, which persisted for four days. However, by day 5 of stress, this effect shifted, and animals increased food consumption, leading to a plateau of weight loss.

The invention is based, at least in part, on the surprising discovery that ghrelin signaling enhances the effects of chronic stress and that functional antagonism of ghrelin signaling can protect against the effects of chronic stress. Accordingly, therapeutic and prophylactic approaches based on antagonism of ghrelin or ghrelin receptor can be used to prevent or reduce the incidence of stress-sensitive disorders, and can also be used to treat stress-sensitive disorders. Further described herein are methods for determining whether a subject exposed to chronic stress has an increased risk of developing a stress-sensitive disorder by measuring ghrelin levels in the subject.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

A surprising aspect of the invention is that, in direct contrast to previous reports, ghrelin signaling is shown herein to enhance the deleterious effects of chronic stress. A link was surprisingly discovered connecting chronic exposure to ghrelin with excessive negative affect. In particular, it is shown herein that repeated agonism of the ghrelin receptor (either systemically or targeting brain circuits relating to negative emotion) potentiates negative emotional states. Endogenous ghrelin levels become gradually elevated with repeated exposure to stress and persist for many weeks beyond the termination of the stress. Significantly, antagonizing the ghrelin receptor during recurring stress completely prevents stress related enhancement of negative emotion. Many of the detrimental effects of recurring stress, including excessive negative emotion, have been believed to be the result of exposure to glucocorticoids, a hormone that is considered a "master" effector in coordinating the body's response to stress. Surprisingly, it is shown herein that ghrelin secretion is stress-induced, yet this secretion is fully independent of glucocorticoids. In addition, the ability of stress to potentiate negative emotion remains even when the endogenous source of all glucocorticoids is removed prior to stress. Additionally, it was surprisingly discovered that an effective dosage of the agents that target the ghrelin receptor described herein for achieving this result is significantly lower than corresponding effective dosages used for administering these compounds for the purpose of treating obesity.

Figure 2C:
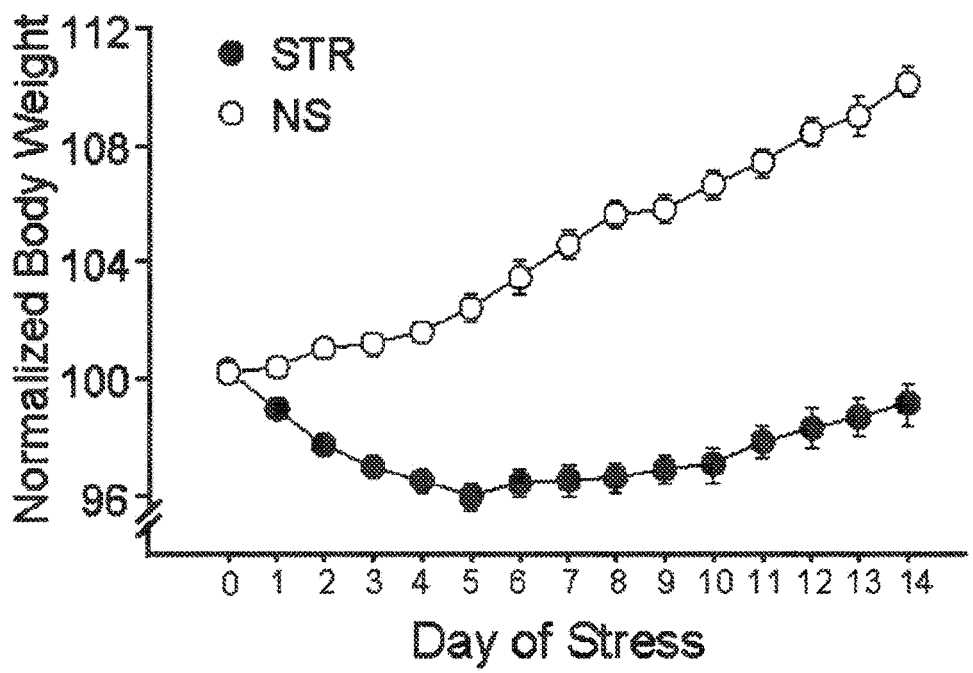

Aspects of the invention relate to the effects of stress and, in particular, chronic stress. As used herein, "stress" refers to a physical, chemical or emotional factor or combination of factors that causes bodily or mental tension and that may be a factor in disease causation. It should be appreciated that any form of stress can be compatible with aspects of the invention. Exposure to stress can be chronic or acute. As used here, "chronic stress" refers to a state of prolonged tension from internal or external stressors, which may cause various physical manifestations. As shown in FIGS. 1 and 2, the effects of chronic and acute stress can be different. Several non-limiting examples of situations where a subject could be exposed to chronic stress include military service such as a combat mission, and natural disasters, such as participation in a search-and-rescue operation or rebuilding following a natural disaster.

Subjects who are exposed to stress can develop stress-sensitive disorders. As used herein, a "stress-sensitive disorder" refers to any condition, disease or disorder that results, at least in part, from exposure to stress or is exacerbated, at least in part, from exposure to stress. Non-limiting examples of stress-sensitive disorders include Post-traumatic Stress Disorder (PTSD), Depressive Disorder, Major Depressive Disorders, Bipolar Disorder, Acute Stress Disorder, anxiety disorders such as Generalized Anxiety Disorder, Obsessive-Compulsive Disorder, social anxiety disorders, Panic Disorders, schizophrenia, phobias, obsessive compulsive disorders, and Trichotillomania. It should be appreciated that any stress-sensitive disorder can be compatible with aspects of the invention.

Post-Traumatic Stress Disorder (PTSD) is an anxiety neurosis caused by exposure to psychological damage by experience beyond a usual corrective ability such as traumas of wars, natural disasters, domestic violence or sexual abuse, etc. It is believed that in addition to psychological manifestations, shrinkage of the hippocampus and dysfunction of prefrontal cortex often occurs. The principal characteristic symptoms involve re-experiencing a traumatic (i.e., psychologically distressing) event, the avoidance of stimuli associated with that event, the numbing of general responsiveness, and increased arousal. The "events" concerned are outside the range of common experiences such as simple bereavement, chronic illness and marital conflict.

Phobias include specific phobias and social phobias. Specific phobia is an anxiety disorder of which the essential feature is a persistent fear of a circumscribed stimulus, which may be an object or situation, other than fear of having a panic attack or of humiliation or embarrassment in social situations (which falls under social phobia). Examples include phobias of flying, heights, animals, injections, and blood. Simple phobias may be referred to as "specific" phobias and, in the population at large. Exposure to the phobic stimulus will almost invariably lead to an immediate anxiety response. Social phobia is characterized by the persistent fear of social or performance situations in which embarrassment may occur.

Aspects of the invention relate to methods by which the effects of recurring stress can be weakened to reduce the potentiating effects of stress on stress-sensitive mental illnesses. Methods associated with the invention comprise administration of a therapeutically effective amount of an agent that antagonizes ghrelin signaling to a subject.

Agents associated with the invention inhibit the level or activity of a component of the ghrelin signaling pathway. These agents are referred to herein as agents that inhibit the level of activity of ghrelin or ghrelin receptor or as antagonists of ghrelin signaling. For example, an agent can target ghrelin itself, or the ghrelin receptor or can target one or more other factors which influence the level or activity of ghrelin, such as ghrelin O-acyltransferase (GOAT). For example, the agent can be a vaccine, such as a vaccine against ghrelin, ghrelin receptor or GOAT.

In certain embodiments, the agent is an antagonist of the ghrelin receptor, which also include: a ghrelin antibody or antigen-binding fragment thereof, a ghrelin derivative, a ghrelin inhibitor, a ghrelin receptor peptide or fragment, a ghrelin receptor inhibitor, a ghrelin receptor antibody or antigen-binding fragment thereof, a ghrelin analog, a ghrelin receptor peptide or fragment and a non-peptide ghrelin receptor antagonist. Examples of antagonist of the ghrelin receptor include a GHSr1a antagonist or a GHSr1a inverse agonist. Other examples of antagonist of the ghrelin receptor include but are not limited to Gly-Ser-Ser(Octanoyl)-Phe-A (SEQ ID NO: 1); where A is —OH, NH$_2$, Leu-Ser-Pro-Glu-X (SEQ ID NO: 2) or -Ala-Lys-Leu-Gln-Pro-Arg-B (SEQ ID NO: 3) where B is —OH or NH$_2$ Gly-Ser-Ser(Octanoyl)-Phe-Leu-Ser-Pro-Glu (SEQ ID NO: 4)

[D-lys-3]-GHRP-6 (His-D-Trp-D-Lys-Trp-D-Phe-Lys-NH$_2$)

L-756867 (i.e. D-ArgPro-Lys-Pro-D-Phe-Gln-D-Trp-Phe-D-Trp-Leu-Leu-NH$_2$ substance P derivative; (D-Lys3)-GHRP-6 (i.e. His-D-Trp-D-Lys-Trp-D-Phe-Lys-NH$_2$ non-peptidyl antagonist denoted L-692400 cyclo(-His-D-Trp-Ala-Trp-D-Phe-)

(2E)-4-(1-aminocyclobutyl)but-2-enoic acid N-((1R)-1-diphenethylcarbamoyl-2-(2-naphthyl)ethyl)-N-methylamide (E)-5-amino-5-methylhex-2-enoic RR)-2-(1-(benzofuran-7-yl)-7-chloro-8-methoxy-1,2,4,5-tetrahydrobenzo[dl-azepin-3-yl)-1-(benzyloxymethyl)-2-oxoethyl]amide 2-amino-N-[(1R)-1-{N-[(1R)-1-(N',N'-dimethylhydrazinocarbonyl)-3-phenylpropyl]-N-methylcarbamoyl}-2-(1H-indol-3-yl)ethyl]-2-methylpropionamide, or 2-[(1R)-1-((2E)-5-amino-5-methylhex-2-enoylamino)-2-(2-naphthyl)ethyl-]-5-phenyloxazole-4-carboxylic acid methyl ester.

The GHSR is encoded by a single gene found at chromosomal location 3q26.2. Alternative mRNA processing generates 2 types of GHSR proteins: GHSR1a and GHSR1b. GHSR1a is a G-protein-linked receptor consisting of 366 amino acids with 7 transmembrane regions. Stimulation of GHSR1a by GHSs or ghrelin triggers the phospholipase C signaling pathway, leading to increased inositol phosphate turnover and protein kinase C activation, resulting in the release of calcium from intracellular stores. GHSR activation also inhibits K channels, allowing the entry of calcium through voltage-gated 1- and T-type channels. In contrast, GHSR1b consists of 289 amino acids with only 5 transmembrane domains. The antagonist of ghrelin receptor may antagonize either GHSR1a or GHSR1b or both.

The agent can also be a compound that inhibits the synthesis or release of ghrelin in the stomach. The agent may also be a compound that reduces or prevents ghrelin from crossing the blood-brain barrier. The agent may also be an esterase such as APT1.

The agent can also be an inhibitory nucleic acid, such as an siRNA or an antisense molecule that inhibits expression of a ghrelin signaling component. The nucleic acid sequence of ghrelin is known in the art. See for instance, Gene ID: 51738 in NCBI database. The inhibitory nucleic acids may be designed using routine methods in the art.

A ghrelin inhibitory nucleic acid typically causes specific gene knockdown, while avoiding off-target effects. Various strategies for gene knockdown known in the art can be used to inhibit gene expression. For example, gene knockdown strategies may be used that make use of RNA interference (RNAi) and/or microRNA (miRNA) pathways including small interfering RNA (siRNA), short hairpin RNA (shRNA), double-stranded RNA (dsRNA), miRNAs, and other small interfering nucleic acid-based molecules known in the art. In one embodiment, vector-based RNAi modalities (e.g., shRNA or shRNA-mir expression constructs) are used to reduce expression of a gene (e.g., a target nucleic acid such as a ghrelin nucleic acid) in a cell. In some embodiments, therapeutic compositions of the invention comprise an isolated plasmid vector (e.g., any isolated plasmid vector known in the art or disclosed herein) that expresses a small interfering nucleic acid such as an shRNA. The isolated plasmid may comprise a specific promoter operably linked to a gene encoding the small interfering nucleic acid. In some cases, the isolated plasmid vector is packaged in a virus capable of infecting the individual. Exemplary viruses include adenovirus, retrovirus, lentivirus, adeno-associated virus, and others that are known in the art and disclosed herein.

A broad range of RNAi-based modalities could be employed to inhibit expression of a gene in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to oligonucleotides to increase resistance to nuclease degradation, binding affinity and/or uptake. In addition, hydrophobization and bioconjugation enhances siRNA delivery and targeting (De Paula et al., RNA. 13(4):431-56, 2007) and siRNAs with ribo-difluorotoluyl nucleotides maintain gene silencing activity (Xia et al., ASC Chem. Biol. 1(3): 176-83, (2006)). siRNAs with amide-linked oligoribonucleosides have been generated that are more resistant to Si nuclease degradation than unmodified siRNAs (Iwase R et al. 2006 Nucleic Acids Symp Ser 50: 175-176). In addition, modification of siRNAs at the 2'-sugar position and phosphodiester linkage confers improved serum stability without loss of efficacy (Choung et al., Biochem. Biophys. Res. Commun. 342(3):919-26, 2006). Other molecules that can be used to inhibit expression of a gene (e.g., a CSC-associated gene) include sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10): 2024-8, 1995; Quattrone et al., Cancer Res. 55(1):90-5, 1995; Lewin et al., Nat Med. 4(8):967-71, 1998). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4): 307-17, 1991; Knudsen and Nielson Nucleic Acids Res. 24(3):494-500, 1996; Taylor et al., Arch. Surg. 132(11): 1177-83, 1997). Minor-groove binding polyamides can bind in a sequence-specific manner to DNA targets and hence may represent useful small molecules for suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). The diverse array of suppression strategies that can be employed includes the use of DNA and/or RNA aptamers that can be selected to target a protein of interest (e.g, ghrelin).

Other inhibitor molecules that can be used include sense and antisense nucleic acids (single or double stranded). Antisense nucleic acids include modified or unmodified RNA, DNA, or mixed polymer nucleic acids, and primarily function by specifically binding to matching sequences resulting in modulation of peptide synthesis (Wu-Pong, November 1994, BioPharm, 20-33). Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, Crit. Rev. in Oncogenesis 7, 151-190).

As used herein, the term "antisense nucleic acid" describes a nucleic acid that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

In some embodiments the inhibitory nucleic acid of the invention is 100% identical to the nucleic acid target. In other embodiments it is at least 99%, 95%, 90%, 85%, 80%, 75%, 70%, or 50% identical to the nucleic acid target. The term "percent identical" refers to sequence identity between two nucleotide sequences. Percent identity can be determined by comparing a position in each sequence which may be aligned for purposes of comparison. Expression as a percentage of identity refers to a function of the number of identical amino acids or nucleic acids at positions shared by the compared sequences. Various alignment algorithms and/or programs may be used, including FASTA, BLAST, or ENTREZ-FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

An inhibitory nucleic acid useful in the invention will generally be designed to have partial or complete complementarity with one or more target genes (i.e., complementarity with one or more transcripts of ghrelin gene). The target gene may be a gene derived from the cell, an endogenous gene, a transgene, or a gene of a pathogen which is present in the cell after infection thereof. Depending on the particular target gene, the nature of the inhibitory nucleic acid and the level of expression of inhibitory nucleic acid (e.g. depending on copy number, promoter strength) the procedure may provide partial or complete loss of function for the target gene. Quantitation of gene expression in a cell may show similar amounts of inhibition at the level of accumulation of target mRNA or translation of target protein.

"Inhibition of gene expression" refers to the absence or observable decrease in the level of protein and/or mRNA product from a target gene. "Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. As an example, the efficiency of inhibition may be determined by assessing the amount of gene product in the cell: mRNA may be detected with a hybridization probe having a nucleotide sequence outside the region used for the inhibitory nucleic acid, or translated polypeptide may be detected with an antibody raised against the polypeptide sequence of that region.

The agent that antagonizes ghrelin signaling can be an agent that has been developed to antagonize ghrelin in other contexts, such as to combat obesity or diabetes. Several non-limiting examples of commercially available agents that antagonize ghrelin signaling include: small molecule ghrelin receptor antagonists from Elixir Pharmaceuticals, ghrelin antagonist AEZS-123 from AEterna Zentaris Inc., anti-ghrelin vaccine from Cytos Biotechnology, ghrelin receptor antagonists from Merck, ghrelin antagonists from Tranzyme Pharma, small molecule ghrelin receptor antagonists from Bayer, ghrelin receptor antagonist DLys3 GHRP-6 from Phoenix Pharmaceuticals, humanized anti-ghrelin antibodies from Eli Lilly and Company and ghrelin binding nucleic acids that antagonize ghrelin activity from Noxxon Pharma AG, each of which is an agent that inhibits the level of activity of ghrelin or ghrelin receptor, as used herein.

Non-limiting examples of agents for inhibiting ghrelin signaling are found in, and expressly incorporated by reference for their teachings related to agents for inhibiting ghrelin signaling from, US Patent publication numbers: US20110318807, US20110257086, US20110245161, US20110245160, US20110021420, US20100286152, US20100254994, US20100196396, US20100196330, US20100086955, US20100021487, US20090275648, US20090253673, US20090149512, US20070275877, US20070237775, US20070025991, US20050201938, US20050191317, US20050070712 and US20020187938, and from U.S. Pat. Nos. 8,013,015, 7,901,679, 7,666,833 and 7,479,271.

The agent can be administered to a subject before, during and/or after exposure to chronic stress. For example, the agent can be administered to a subject in anticipation of exposure to chronic stress, such as prior to participation in a military operation. As such, the agent can protect against the consequences of exposure to chronic stress. The agent can also be administered to a subject during exposure to chronic stress to protect against the consequences of exposure to chronic stress and treat symptoms associated with the effects of chronic stress. The agent can also be administered after exposure to chronic stress to protect against the consequences of exposure to chronic stress and treat symptoms associated with the effects of chronic stress.

Further aspects of the invention relate to determining whether a subject exposed to chronic stress has an increased risk of developing a stress-sensitive disorder. For example, if elevated levels of ghrelin are detected in a subject during or after exposure to chronic stress, the subject may be considered to be at increased risk of developing a stress sensitive disorder following exposure to the chronic stress. Levels of ghrelin can be measured according to any assay familiar to one of ordinary skill in the art. For example, levels of ghrelin could be measured by a Western blot or an ELISA. In some embodiments, an assay to measure ghrelin levels is conducted on a blood sample.

The level of ghrelin in a subject is compared to a control level. It should be appreciated that the appropriate control will vary depending on the circumstances. In some embodiments, the control level can be the level of ghrelin in the same subject prior to exposure to chronic stress. In other embodiments, the control level can be the level of ghrelin in a subject who has not been exposed to chronic stress. Levels of ghrelin may be measured at multiple time points and may be measured before, during and after exposure to chronic stress. For example, in some embodiments, the level of ghrelin is measured in a subject prior to exposure to stress and then one or more times during and/or after exposure to chronic stress. In some embodiments, a subject who has prolonged elevated levels of ghrelin following exposure to chronic stress may be considered a subject who has an increased risk of developing a stress-sensitive disorder. A subject who is found to have elevated ghrelin levels following exposure to chronic stress can be administered an agent that antagonizes ghrelin signaling.

Administering an antagonist of ghrelin signaling to a subject who will be exposed to chronic stress may reduce the incidence of trauma-induced disorders such as post-traumatic stress disorder (PTSD). Moreover, in the past, most stress-sensitive illnesses have been treated with the same compounds that are used to treat other mental illnesses, such as selective serotonin reuptake inhibitors (SSRIs). However, these drugs do not offer any clinical benefit to a significant number of patients diagnosed with these disorders. Having drugs with a novel mechanism of action, targeting the ghrelin signaling pathway, may be beneficial for patients who are resistant to traditional avenues of treatment.

The methods of the invention are useful for treating a subject in need thereof. A subject in need thereof can be a subject who will be exposed to chronic stress, is currently exposed to chronic stress or has been exposed to chronic stress. For example, a subject in need thereof may be a subject involved, or who will be involved, in a military operation or combat mission. A subject in need thereof can be a subject having or at risk of a stress sensitive disorder. For example, a subject can be a patient who is diagnosed with a stress-sensitive disorder, or a subject with a strong familial history of such disorders.

In its broadest sense, the terms "treatment" or "to treat" refer to both therapeutic and prophylactic treatments. If the subject in need of treatment is experiencing a condition (i.e., has or is having a particular condition), then "treating the condition" refers to ameliorating, reducing or eliminating one or more symptoms associated with the disorder or the severity of the disease or preventing any further progression of the disease. If the subject in need of treatment is one who is at risk of having a condition, then treating the subject refers to reducing the risk of the subject having the condition or preventing the subject from developing the condition.

A subject shall mean a human or vertebrate animal or mammal including but not limited to a dog, cat, horse, cow, pig, sheep, goat, turkey, chicken, and primate, e.g., monkey.

Therapeutic compounds associated with the invention may be directly administered to the subject or may be administered in conjunction with a delivery device or vehicle. Delivery vehicles or delivery devices for delivering therapeutic compounds to surfaces have been described. The therapeutic compounds of the invention may be administered alone (e.g., in saline or buffer) or using any delivery vehicles known in the art. For instance, the following delivery vehicles have been described: Cochleates; Emulsomes, ISCOMs; Liposomes; Live bacterial vectors (e.g., *Salmonella, Escherichia coli, Bacillus calmatte-guerin, Shigella, Lactobacillus*); Live viral vectors (e.g., Vaccinia, adenovirus, Herpes Simplex); Microspheres; Nucleic acid vaccines; Polymers; Polymer rings; Proteosomes; Sodium Fluoride; Transgenic plants; Virosomes; Virus-like particles. Other delivery vehicles are known in the art and some additional examples are provided below.

The term effective amount of a therapeutic compound of the invention refers to the amount necessary or sufficient to realize a desired biologic effect. For example, an effective amount of a therapeutic compound associated with the invention may be that amount sufficient to ameliorate one or more symptoms of a stress sensitive disorder in a subject who has been exposed to chronic stress. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic compounds being administered the size of the subject, or the severity of the disease or condition. One of ordinary skill in the art can empirically determine the effective amount of a particular therapeutic compound associated with the invention without necessitating undue experimentation.

Subject doses of the compounds described herein for delivery typically range from about 0.1 μg to 10 mg per administration, which depending on the application could be given daily, weekly, or monthly and any other amount of time there between. The doses for these purposes may range from about 10 μg to 5 mg per administration, and most typically from about 100 μg to 1 mg, with 2-4 administrations being spaced days or weeks apart. In some embodiments, however, parenteral doses for these purposes may be used in a range of 5 to 10,000 times higher than the typical doses described above.

Surprisingly, it was discovered that the doses necessary to block stress-enhanced fear are significantly lower than the dose needed to alter food consumption. In some instances, a therapeutically effective amount of an agent of the invention is 100-1,000 times lower than a typical dose used for altering food consumption. In other embodiments, a therapeutically effective amount of an agent of the invention is 10,000 times lower than a typical dose used for altering food consumption. In some embodiments a compound of the invention is administered at a dosage of between about 1 and 10 mg/kg of body weight of the mammal. In other embodiments a compound of the invention is administered at a dosage of between about 0.001 and 1 mg/kg of body weight of the mammal. In yet other embodiments a compound of the invention is administered at a dosage of between about 10-100 ng/kg, 100-500 ng/kg, 500 ng/kg-1 mg/kg, or 1-5 mg/kg of body weight of the mammal, or any individual dosage therein.

The formulations of the invention are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of the therapeutic compound associated with the invention can be administered to a subject by any mode that delivers the therapeutic agent or compound to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, rectal and intracerebroventricular.

For oral administration, the therapeutic compounds of the invention can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189). Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the therapeutic agent or by release of the biologically active material beyond the stomach environment, such as in the intestine.

To ensure full gastric resistance a coating impermeable to at least pH 5.0 is preferred. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e., powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the therapeutic agent may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the therapeutic agent either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the therapeutic compounds of the invention. The therapeutic agent is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144

(leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of therapeutic agent. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified therapeutic agent may also be prepared in different formulations depending on the type of chemical modification or the type of device employed.

Formulations suitable for use with a nebulizer, either jet or ultrasonic, will typically comprise therapeutic agent dissolved in water at a concentration of about 0.1 to 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the therapeutic agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing therapeutic agent and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Intra-nasal delivery of a pharmaceutical composition of the present invention is also contemplated. Intra-nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Agents associated with the invention can be formulated as vaccines, such as an anti-ghrelin vaccine or an anti-GOAT vaccine. Preferably, prophylactic vaccination is used in subjects that are not diagnosed with a condition such as a stress-sensitive condition, and more preferably the subjects are considered at risk of developing a condition such as a stress-sensitive condition. For example, the subject may be administered a vaccine, such as an anti-ghrelin vaccine or an anti-GOAT vaccine before, during and/or after exposure to chronic stress. Vaccines can be administered through any means familiar to one or ordinary skill in the art. For example, vaccines can be administered by immersion or orally.

Vaccines in some instances activate the humoral immune system (i.e., the antibody dependent immune response). Other vaccines activate the cell-mediated immune system including cytotoxic T lymphocytes.

The agents, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The therapeutic compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a therapeutic compound of the invention optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agents may be delivered to the brain using a formulation capable of delivering a therapeutic agent across the blood brain barrier. One obstacle to delivering therapeutics to the brain is the physiology and structure of the brain. The blood-brain barrier is made up of specialized capillaries lined with a single layer of endothelial cells. The region between cells are sealed with a tight junction, so the only access to the brain from the blood is through the endothelial cells. The barrier allows only certain substances, such as lipophilic molecules through and keeps other harmful compounds and pathogens out. Thus, lipophilic carriers are useful for delivering non-lipohilic compounds to the brain. For instance, DHA, a fatty acid naturally occurring in the human brain has been found to be useful for delivering drugs covalently attached thereto to the brain (Such as those described in U.S. Pat. No. 6,407,137). U.S. Pat. No. 5,525,727 describes a dihydropyridine pyridinium salt carrier redox system for the specific and sustained delivery of drug species to the brain. U.S. Pat. No. 5,618,803 describes targeted drug delivery with phosphonate derivatives. U.S. Pat. No. 7,119,074 describes amphiphilic prodrugs of a therapeutic compound conjugated to an PEG-oligomer/polymer for delivering the compound across the blood brain barrier. Others are known to those of skill in the art.

The therapeutic agents of the invention may be delivered with other therapeutics for treating stress sensitive disorders.

The present invention is further illustrated by the following Examples, which in no way should be construed as further limiting. The entire contents of all of the references (including literature references, issued patents, published patent applications, and co-pending patent applications) cited throughout this application are hereby expressly incorporated herein by reference.

EXAMPLES

Figure 3A:
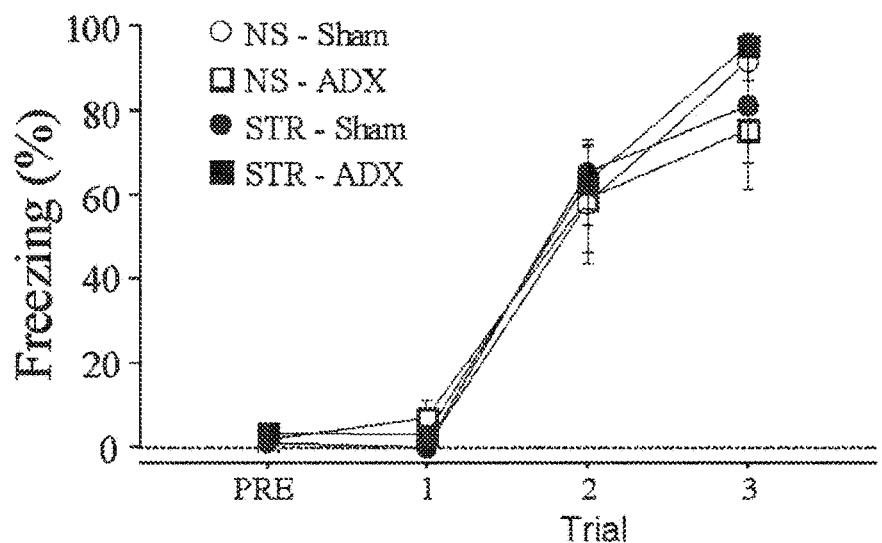
FIG. 3 shows that stress-related vulnerability to fear is independent of glucocorticoid or adrenaline secretion. Rats received either adrenalectomy (ADX groups) or sham (Sham groups) surgery. After recovery, animals were administered a psychological stressor (4 h/day) for 14 days (STR groups) or daily handling (No Stress group; NS). Twenty-four hours after the last stress or handling session, half of the rats were administered auditory fear conditioning (A), and fear to the auditory cue was subsequently assessed (B). Stress enhanced fear memory, regardless of whether the adrenal glands were intact or absent, indicating that stress-related enhancement of fear is independent of glucocorticoid or adrenaline secretion.
Figure 3B:
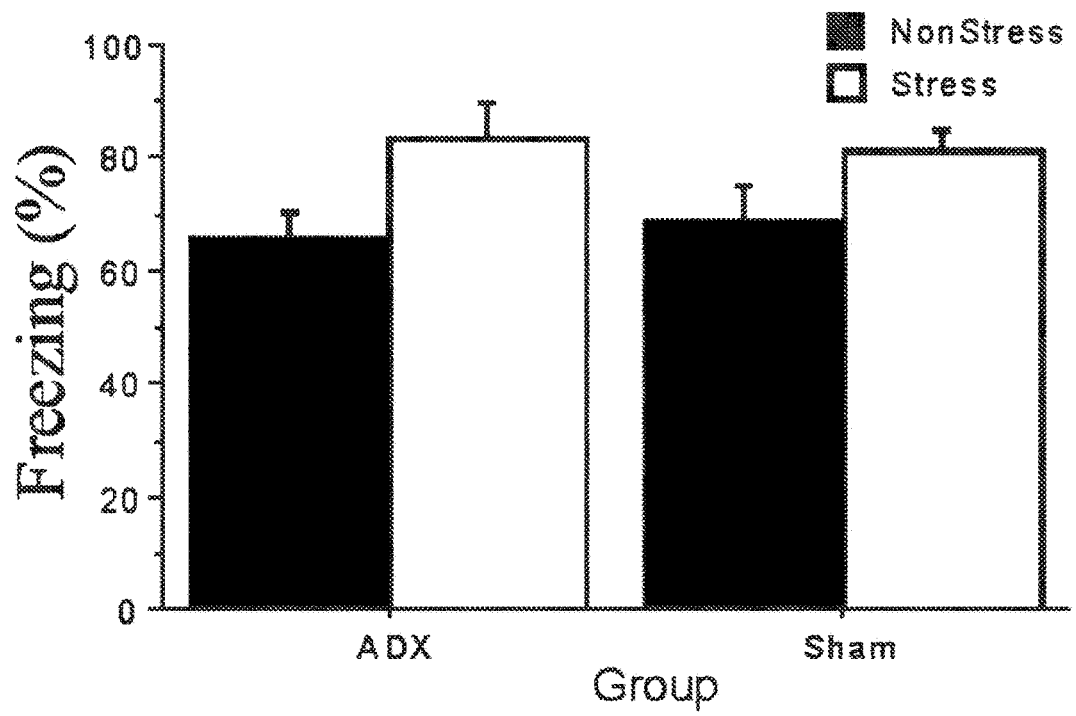
Figure 4C:
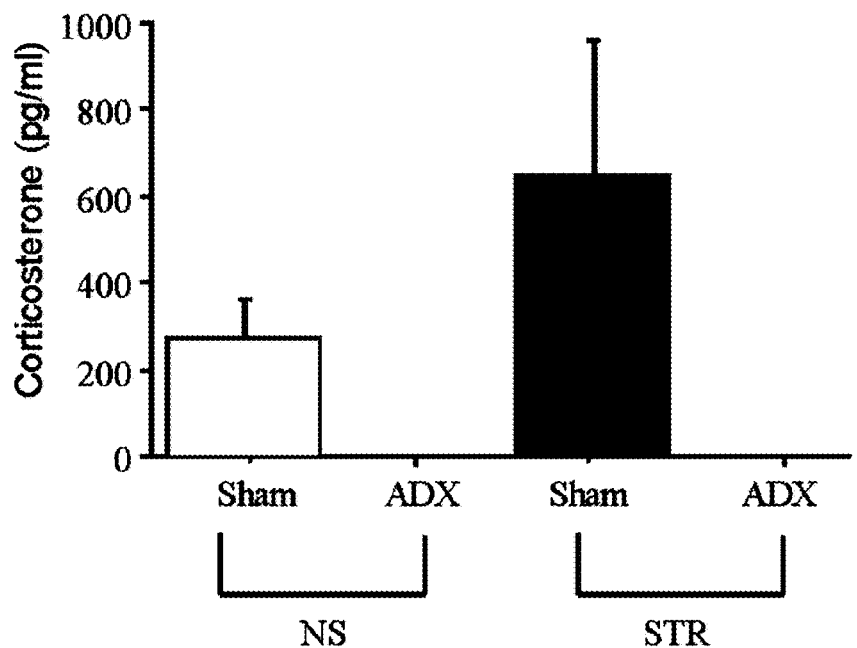
FIG. 4 shows that stress-related increases in ghrelin are independent of adrenal hormones. Half of the rats were sacrificed 24 h following the final stress or handling session for sampling of trunk blood and measurement of hormones using ELISA. C) Successful removal of the adrenal gland was confirmed by the absence of detectable corticosterone in the blood samples of rats in the ADX groups. Also, corticosterone was elevated by stress when animals had intact adrenal glands (Sham-STR vs. Sham-NS comparison). D) In contrast, plasma ghrelin was elevated by stress, regardless of whether the adrenal glands were intact or absent.
Figure 4D:
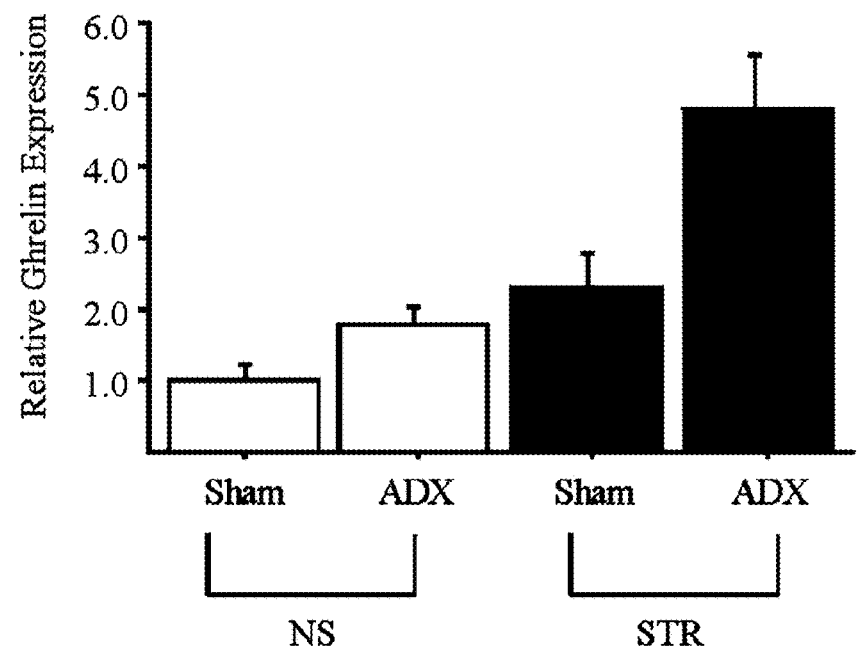
Figure 5A:
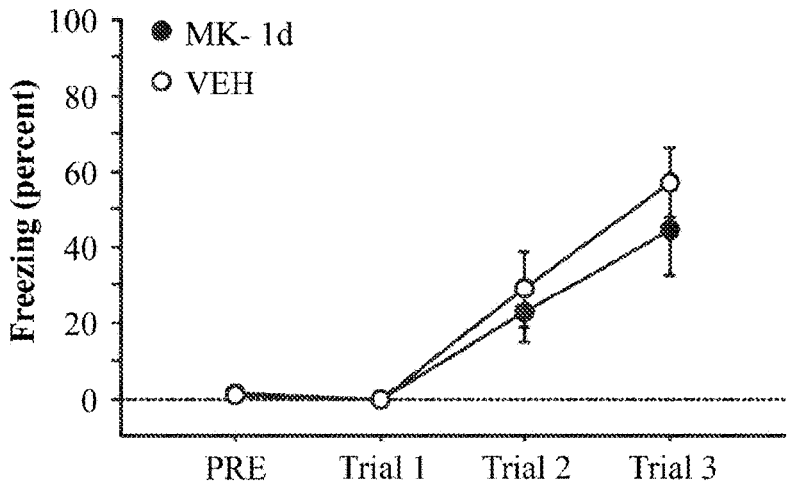
FIG. 5 shows that repeated activation of ghrelin receptor is sufficient for vulnerability to fear. Rats received daily injections of either MK677, a ghrelin receptor agonist, or saline (VEH) for 1, 3, or 5 days. Twenty-four hours after the final injections, all rats were subjected to auditory fear conditioning, and fear to the auditory cue was subsequently assessed. Injections of the ghrelin receptor agonist had no effect on fear memory when given for 1 or 3 days (top and middle panels, respectively), but increased fear memory when given for 5 days (lower panel).
Figure 5A:
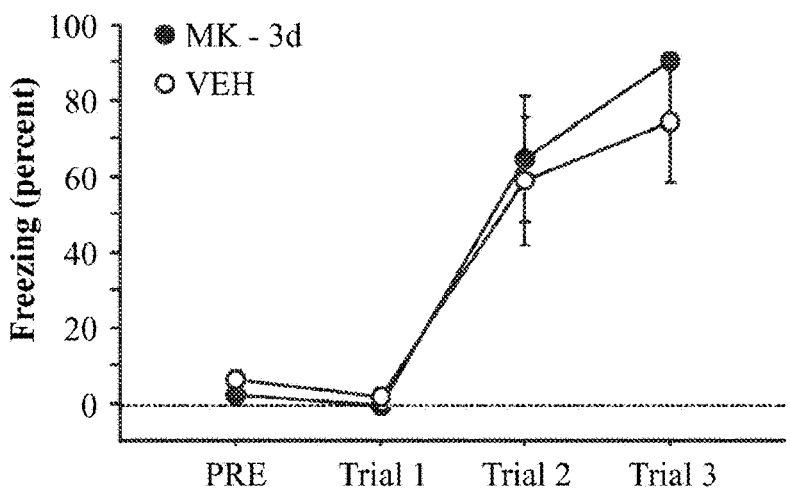
Figure 5A:
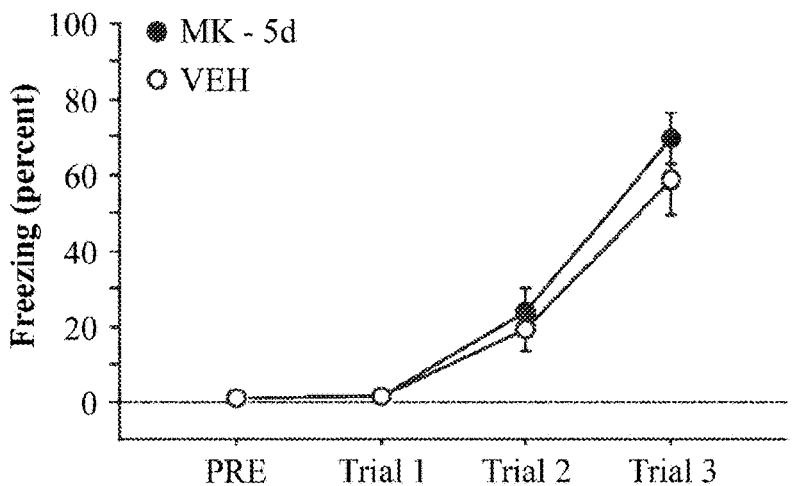
Figure 5B:
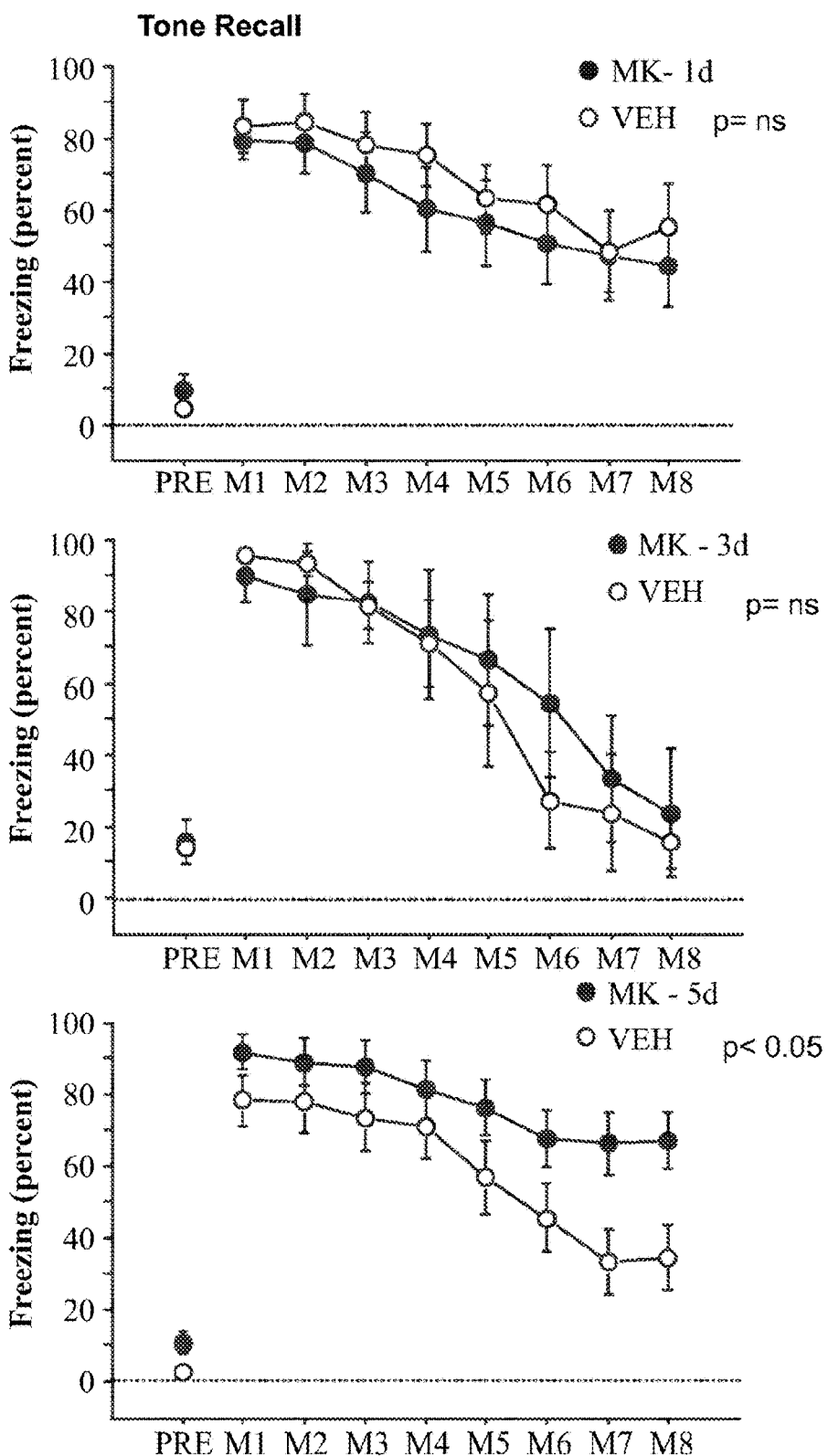
Figure 6A:
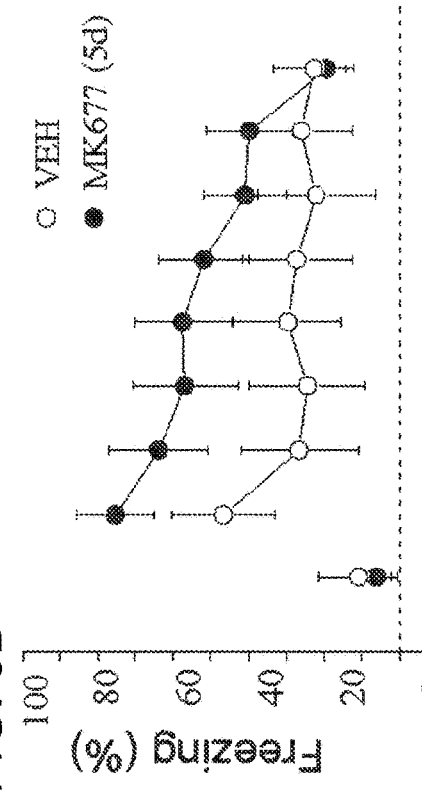
FIG. 6 shows that repeated activation of ghrelin receptors in amygdala is sufficient to produce vulnerability to fear. Rats were implanted with cannulae aimed at the basolateral amygdala. Following recovery, rats received daily intra-BLA infusions of either MK677, a ghrelin receptor agonist, or saline (VEH) for 5 days. Body weight and food consumption was monitored daily throughout the experiment. Twenty-four hours after the final infusions, all rats were subjected to auditory fear conditioning (A), and fear to the auditory cue was subsequently assessed (B). Repeated activation of the ghrelin receptor in the BLA was sufficient to enhance fear memory, without affecting body weight (C) or food consumed (D). The effect was replicated when bioactive ghrelin was infused in lieu of MK677 (E,F).
Figure 6B:
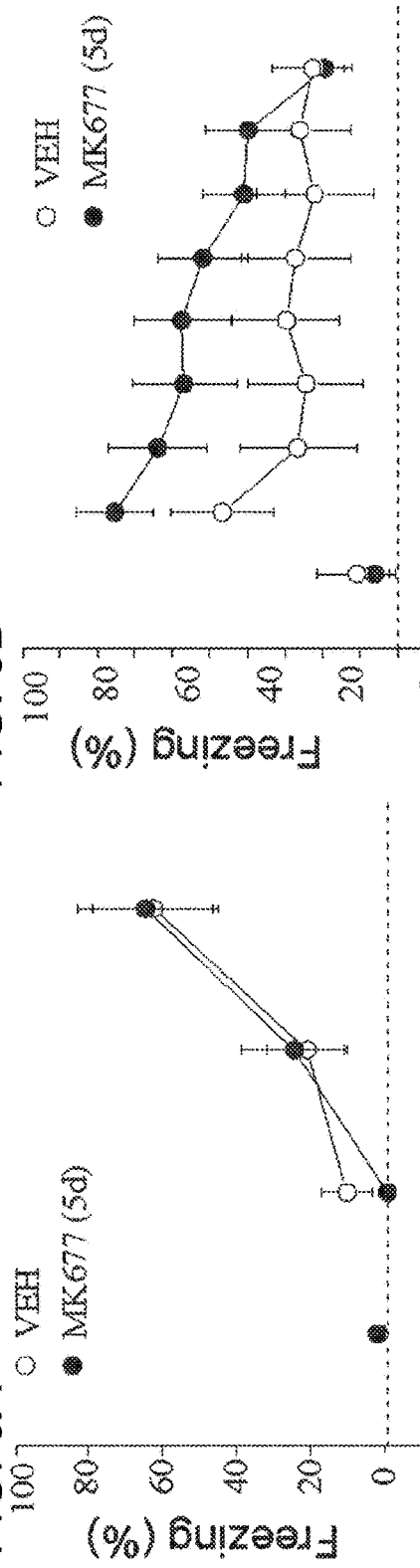
Figure 6C:
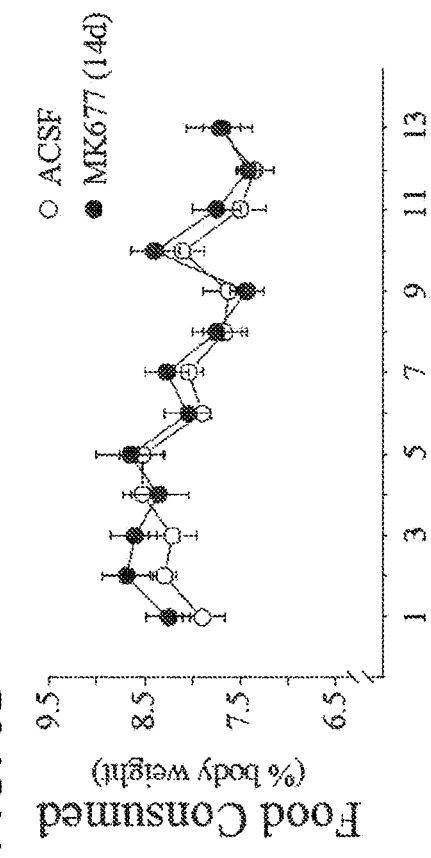
Figure 6D:
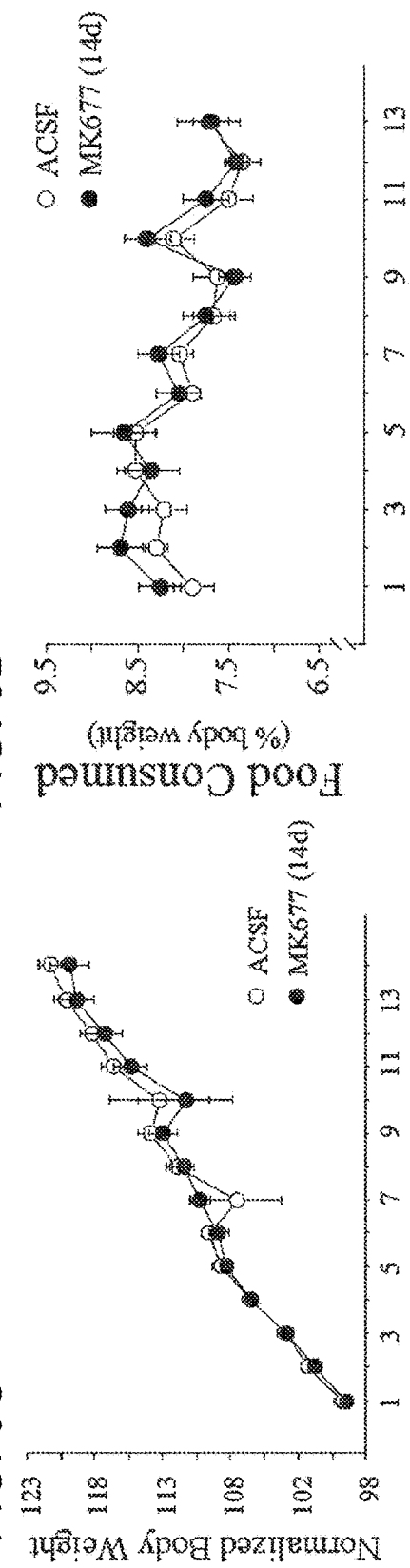
Figure 6E:
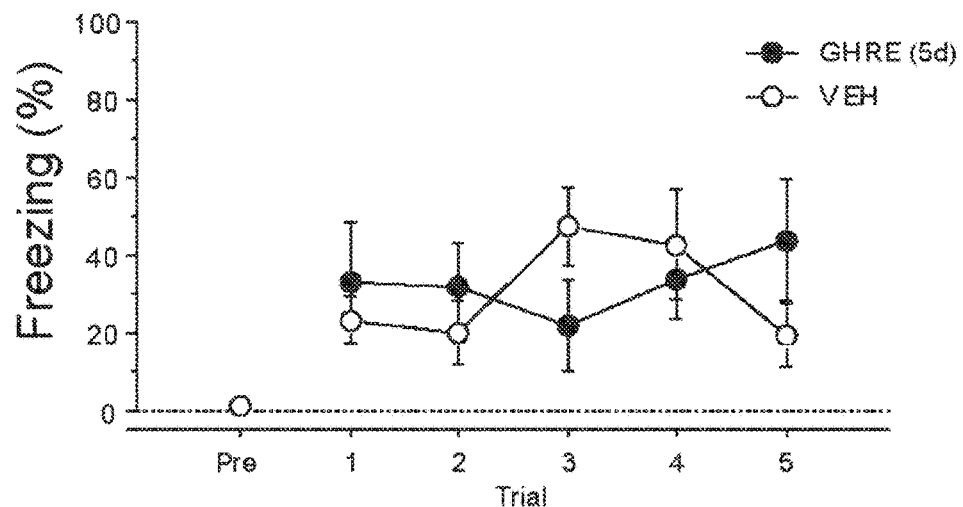
Figure 6F:
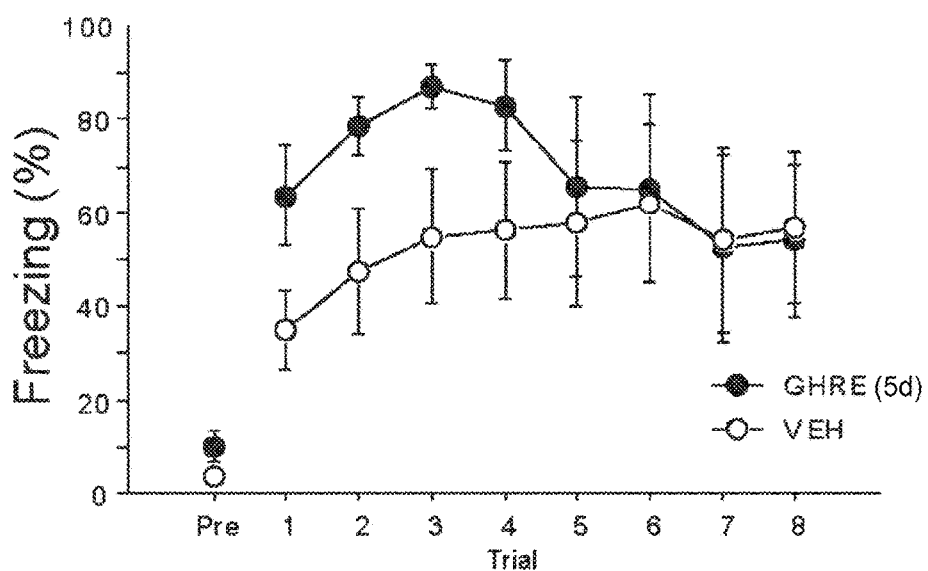
Figure 7A:
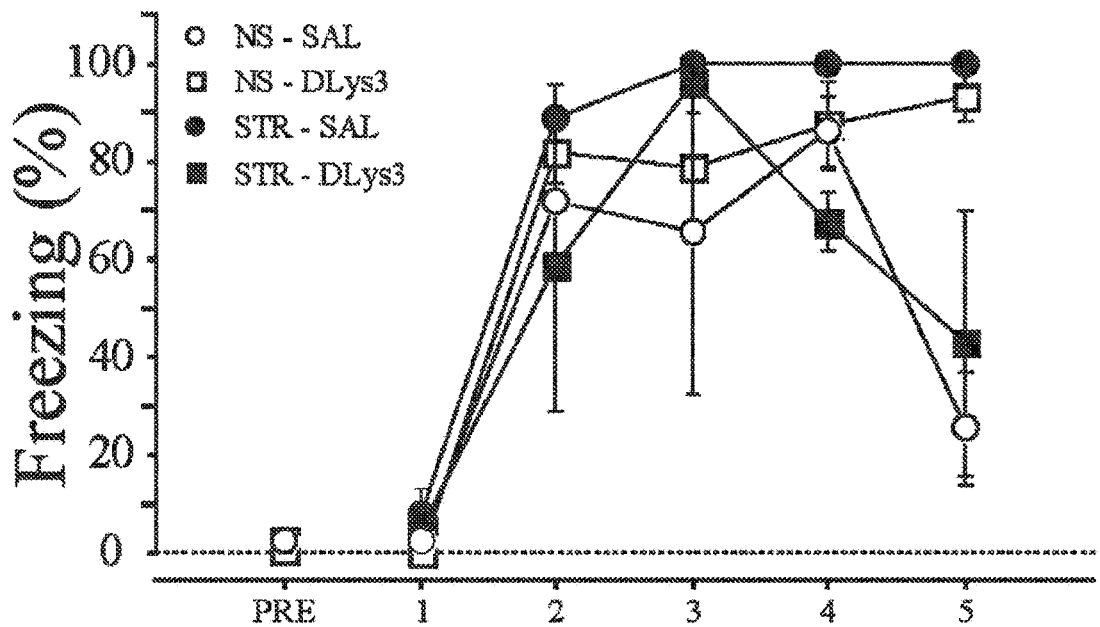
FIG. 7 shows that activation of the ghrelin receptor is necessary for stress-induced vulnerability to excessive fear. Rats received daily injections of either Dlys-3, a ghrelin receptor inverse agonist, or saline (VEH) daily prior to psychological stress (4 h/day) for 14 days (STR groups) or daily handling (No Stress group; NS). Twenty-four hours after the final injections, all rats were subjected to auditory fear conditioning (A), and fear memory was subsequently assessed (B). Ghrelin receptor antagonism during chronic stress was sufficient to prevent stress-related enhancement of fear memory; no effect of the treatment was observed in unstressed rats. Despite blockade of the stress effects on fear, the Dlys-3 had no effect on stress-related changes in food consumption (C) or body weight (D).
Figure 7B:
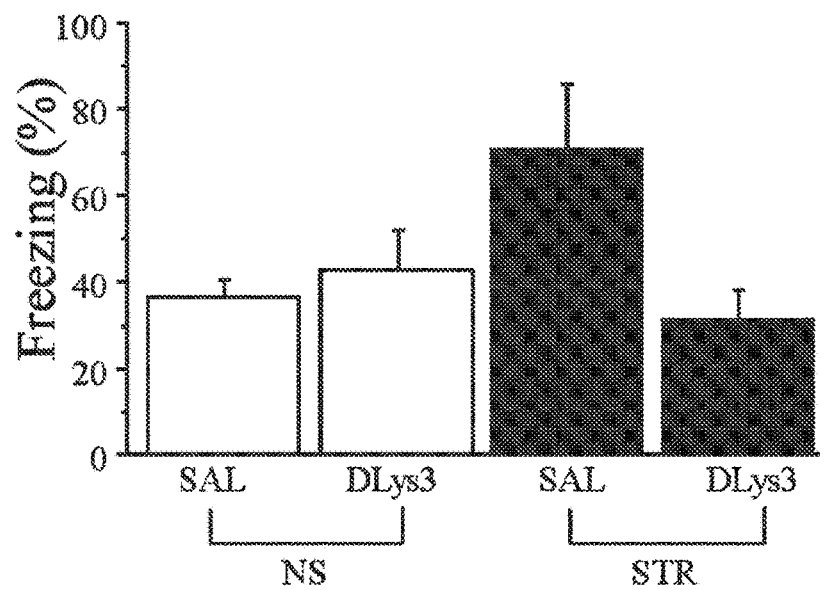
Figure 7C:
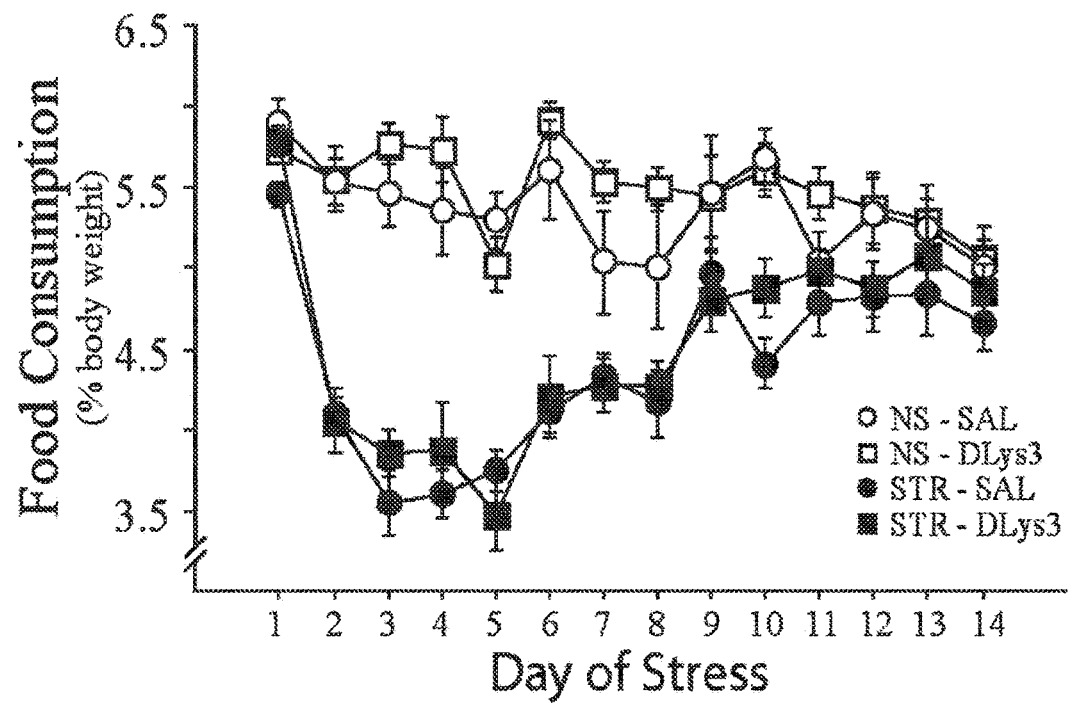
Figure 7D:
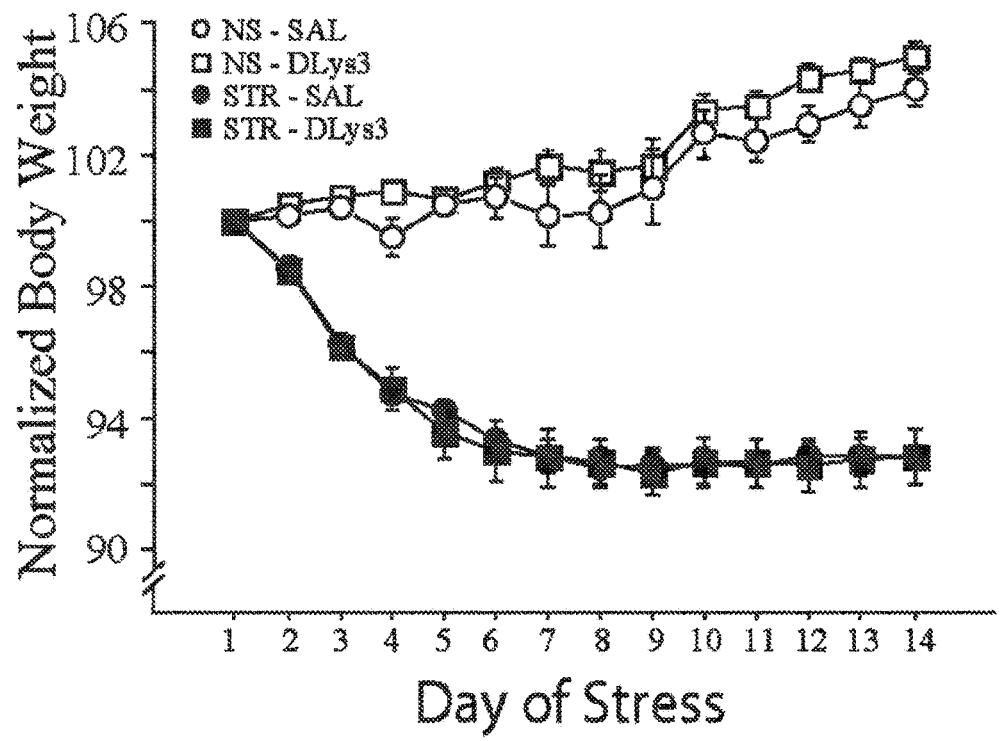

Although the body's stress response is adaptive in the short-term, its repeated activation enhances vulnerability to psychiatric disorders of fear and anxiety. Little is known about the biological mechanisms that underlie this maladaptive response to a recurring stressor. Here we report that the peripheral hormone ghrelin is responsible for the enhancement of fear learning following repeated stress (FIGS. 5-7). Stress-induced increases in bioactive ghrelin and fear learning were observed following long-term, but not short-term stress exposure. These changes were independent of adrenal stress hormone release (FIGS. 3-4). Additionally, repeated activation of ghrelin receptors was sufficient to enhance fear learning, an effect mediated by repeated activation of ghrelin receptors in the amygdala (FIGS. 5-6). Finally, blockade of the ghrelin receptor during recurrent stress was sufficient to abolish stress-related enhancement of fear learning without affecting learning in unstressed animals. These results suggest a novel biomarker for a maladaptive consequence of recurrent stress, and strongly suggest that anti-ghrelin strategies may have therapeutic value in the prevention of stress-sensitive psychiatric illnesses such as post-traumatic stress disorder.

Example 1: Materials and Methods

Subjects.

All experiments used adult male Long Evans rats (250-350 g, Taconic, Germantown, N.Y.), housed individually (68-72° F.; 12-h light-dark cycle, 7 AM lights on). Food and water (or 0.9% saline for adrenalectomy experiments) was provided ad libitum. Stressed and unstressed animals were housed in separate cubicles. All procedures were in accordance with the US National Institutes of Health (NIH) Guide for the Care and Use of Laboratory Animals and were approved by the MIT Institutional Animal Care and Use Committee and the Animal Care and Use Review Office of the USAMRMC.

Adrenalectomy.

Rats that were adrenalectomized were allowed to recover 1 week before being subjected to experimentation. Briefly, bilateral adrenalectomy was carried out through lateral incisions under 3.5% isoflurane anesthesia. Sham adrenalectomy was performed by making the incision through the skin and muscle and locating the adrenal glands. Muscle incisions were closed with chromic gut sutures and skin incisions were closed with wound clips. Some adrenalectomized rats were purchased from Taconic (Germantown, N.Y.). Gland amputation was verified by dissection after removal and further verified by plasma corticosterone analysis.

Cannulae Implants.

Rats were anesthetized with a cocktail of 10 mg/kg acepromazine, 100 mg/kg xylazine, and 100 mg/kg ketamine (1 ml/kg; i.p.). Rats were mounted into a dual arm stereotaxic frame (Kopf Instruments; Tujunga, Calif.). The rats were then bilaterally implanted with 23-gauge stainless steel guide cannulae aimed 1 mm above the lateral amygdala: A/P −2.0, M/L+/−5.3, D/V −5.4, relative to brain surface and bregma (45). The cannulae were secured by the placement of three jeweler screws in the skull and dental acrylic. Dummy cannulae extending 1 mm past the tip of the guide cannulae were placed into the guide cannula after surgery and changed every other day. Rats received 0.03 mg/kg of Buprenex (1 ml/kg; s.c.) as post-operative pain management every 12 h for at least 24 h and up to 3 days. All rats recovered for a minimum of 5 days before experimentation commenced.

Virus Preparation.

The amplicons were previously characterized and described (29). Virus was packaged with the 5 dl 1.2 helper virus and 2-2 cells using standard methods (46). Virus was purified on a sucrose gradient, pelleted, and resuspended in 10% sucrose in D-PBS. Titers were ~1×108 IU/ml.

Virus Infusions.

Pulled glass pipettes were backfilled with silicone oil and the appropriate virus solution. The pipettes were mounted in stereotaxic barrel holder and the pipette plunger was placed against a custom-made apparatus designed to control the plunger via a syringe pump (Harvard Apparatus, Hollison, Mass.). Rats were anesthetized and mounted in a stereotaxic frame as described for cannulae implants. Small holes were drilled for intra-cranial placement of a pulled glass pipette aimed within the lateral amygdala: A/P −2.0, M/L+/−5.3, D/V −6.4, relative to brain surface and bregma (45). Virus was infused at 0.1 ul/m for 20 m (2 ul total volume per side). The glass pipette remained in the brain for 10 m before being withdrawn. Incisions were closed with wound clips and Buprenex was administered as for cannulae implants.

Drug Preparation.

For systemic drug delivery, rats were injected with 1 ml/kg (i.p.) of the appropriate solution. All drugs were solubilized in 0.9% saline (vehicle) such that injection volumes remained constant for each experiment. MK-0677 (Merck; Whitehouse, N.J.) is a highly specific GHSR1a agonist that readily crosses the blood-brain barrier and has a half-life of over six hours (47, 48). A dose of 0.5 mg/ml, diluted in vehicle, was selected because it is well-tolerated and results in significant and prolonged increases in growth hormone release (48). D-Lys3-GHRP-6 (Tocris Biosciences; Minneapolis, Minn.) was diluted to 2.74 ug/ml in vehicle. D-Lys3-GHRP-6 is a selective and potent inhibitor of GHSR 1a (49, 50) with an IC50 of 0.9 µM (51) (Tocris Bioscience literature). It also crosses the blood brain barrier (52). The only other known receptor class with affinity for D-Lys3-GHRP-6 is the melanocortin receptors but the Ki=26-120 µM so the dilute dose used here would not be expected to affect these receptors. D-Lys3-GHRP-6 was injected within 30 m of the start of immobilization stress or following handling. For experiments using intra-BLA drug delivery, drugs were solubilized in physiological artificial cerebrospinal fluid (vehicle; pH=7.35). MK-0677 was solubilized to 0.5 ug/ul. For bioactive ghrelin, a dose of 5 nmol/ul, diluted in vehicle was selected as it was previously shown to have behavioral effects following a single infusion into the amygdala(16).

Drug Infusion.

For intra-cranial infusions, rats were placed in 5-gallon buckets containing bedding. The dummy cannulae were removed and injectors (30G stainless steel cannulae; extending 1 mm beyond the cannulae end) were inserted. The injectors were attached to Hamilton syringes (10 ul; Hamilton Co., Reno, Nev.) via polyethylene tubing, and the syringes were mounted in a Harvard syringe pump (Harvard Apparatus; Holliston, Mass.). Infusions were given at a rate of 0.1 ul/m for 5 m for a total volume of 0.5 ul/side, with 1 m for diffusion, before the injectors were removed and new dummy cannulae were inserted.

Immobilization Stress.

Immobilization stress was administered 4 h per day for 1-14 consecutive days, depending on the experiment. Animals were placed in Decapicone plastic bags (Braintree Scientific; Braintree, Mass.), which were secured at the tail. Stress occurred in a lab room used for no other procedures. All stress sessions were performed between LOAM and 4 PM. Unstressed control rats were handled daily for 30 s. For further parallel control parameters, food was removed from the unstressed rats daily for the same 4 h period in which stressed animals were immobilized and, therefore, without food.

Water Stress.

Water stress was administered 1 h per day for 14 consecutive days. Animals were placed in cages with room temperature water 1.5 to 2 inches deep. All sessions were performed between 12 pm and 2 pm. Unstressed control rats were handled daily for 30 s. For further parallel control parameters, food was removed from the unstressed rats daily for the same 1 h period as above.

Pavlovian Fear Conditioning.

Fear conditioning experiments were conducted in a modified chamber (MED Associates; St. Albans, Vt.) housed in a sound-attenuated cubicle. The animals were placed in individual chambers and infrared video of each session was recorded. Each experiment used auditory fear conditioning wherein rats received 3-5 tone (2 kHz, 85 dB, 10-16 s)—footshock (1-2 s, 0.4-0.7 mA) pairings in a unique context (metal shock grid floors, chamber fan on, 0.3% PineSol odor, house and room lights on). Animals were allowed 2-3 m to habituate to the chamber before tone-footshock pairings were given at intervals of 1-4 m. Fear memory was tested 24-72 h later by placing the animals in a novel context (white Plexiglas plastic floors, curved Plexiglas wall inserts, fans off, 1% acetic acid odor, house and room lights off). One to 5 m after placement in the novel context, fear to the tone was assessed either by presenting a continuous tone (2 kHz, 85 dB, 8 minutes) or several discrete tones (15 10-16 s tones with 1-4 m ISI). Freezing was measured using commercial software (VideoFreeze, MedAssociates, St. Albans, Vt.).

Elevated Plus Maze.

Rats were tested for anxiety using an elevated plus maze (Hamilton Kinder; Poway, Calif.). The maze had two open arms (51 cm×12 cm each) and was located in a moderately lit room. Open arms consisted of black Plexiglas floors and no walls. The closed arms had black Plexiglas walls 40 cm high. Animals were placed on an open arm 88 cm above the ground facing away from the center of the maze. Automated software (Motor Monitor 4.14) recorded the second by second movements of the animals while the experimenter made observations in an obscured corner. Each session lasted 8 m and both the observer and the software recorded the latency to exit the first arm and the number of entries into the open and closed arms. Additionally, the software recorded time spent in the each region of the maze. The maze was cleaned with 70% ethanol after each animal's session.

Trunk Blood Collection.

Perimortem blood was collected from the trunk after decapitation in a tube which contained 1:100 v/v 0.5 M EDTA and 1:100 v/v HALT (Pierce; Rockford, Ill.). Immediately after collection, plasma was extracted by centrifugation (2,100 g at 4° C. for 10-15 m). The plasma layer was then collected and half the volume treated with 10% v/v 1M HCl in order to stabilize the acylated form of ghrelin. Samples were stored at −20° C. or −80° C.

Histology.

Following completion of the experiment, animals were anesthetized with an overdose of isoflurane and intracardially perfused with physiological saline followed by 4% formalin fixative in saline. Brains were harvested and placed in 4% formalin for 24-72 h. The brains were then transferred to a 30% sucrose/4% formalin solution for a minimum of 3 days. For brains infused with virus, solutions containing paraformaldehyde were used in lieu of formalin. Coronal sections (40 μm) were made and mounted on gelatinized slides. Tissue that did not contain virus was stained with 0.1% cresyl violet. Slides were then assessed for cannulae position or GFP florescence. Animals with incorrect placements were excluded from all analyses.

Hormone Assays.

Corticosterone, acylated ghrelin, growth hormone and CRF levels were determined using commercial ELISA kits. For corticosterone, non-acidified plasma was diluted 1:25 in assay buffer 15 (Enzo Life Sciences; Farmingdale, N.Y.). For acylated ghrelin, the acidified sample was used for the active ghrelin ELISA (Millipore; Billerica, Mass.) and processed according to the manufacturer's protocol. Samples were excluded from analysis if they displayed signs of hemolysis or lipemia. For growth hormone, brain tissue was homogenized 1:6 in lysis buffer and was assayed as per manufacturer's protocol (Millipore; Billerica, Mass.). For CRF, brain tissue collected by micro-dissection was homogenized 1:30 w/v in lysis buffer and assayed per manufacturer's protocol (Kamiya Biomedical Company, Seattle, Wash.).

Statistics.

For each fear memory session, conditional freezing was assessed as a percentage of time spent freezing, a probability estimate that is amenable to analysis with parametric statistics. These probability estimates of freezing, along with other measures, were analyzed using ANOVA. Post hoc comparisons in the form of Fisher's PLSD tests were performed after a significant omnibus F-ratio ($p<0.05$). Statistical trends are noted in the text when omnibus Fratio did not reach $p<0.05$ but were $p<0.10$. All data where $p>0.10$ are identified as not significant (ns).

Figure 8A:
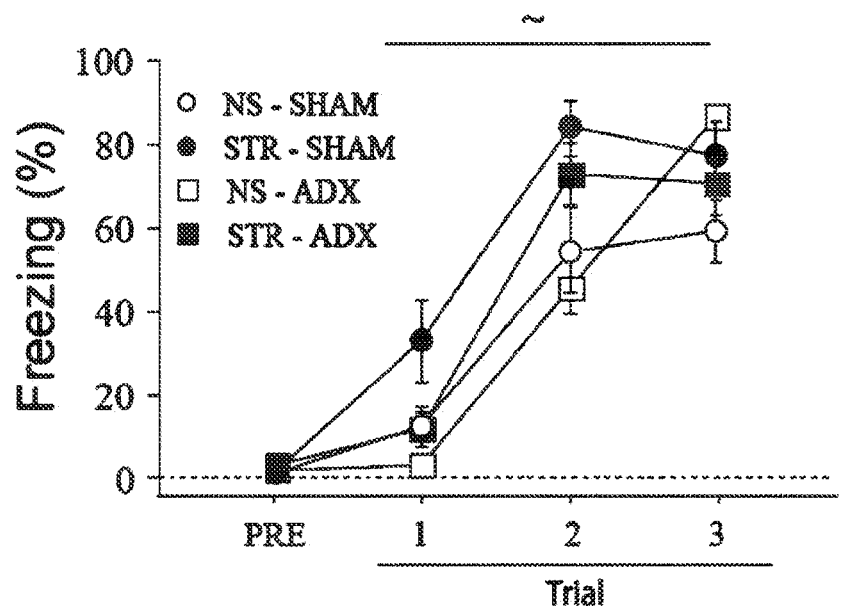
FIG. 8 shows that stress-related changes in fear and ghrelin are independent of adrenal stress hormones. Animals received adrenalectomy (ADX) or sham surgery (SHAM). After at least a week of recovery, animals received either 14 days (4 h/d) immobilization stress (STR) or gentle handling (NS). (a) Some animals received auditory Pavlovian fear conditioning 24 h after the last stress or handling session. (b) Fear to the tone was assessed 48 h later in a novel context. In a separate group of animals, trunk blood was collected 24 h after the last stress session. Plasma level corticosterone (c) and acylated ghrelin (d) were determined with ELISA. All data are mean±s.e.m. * p<0.05, *** p<0.001, ~p<0.10 in planned comparisons.
Figure 8B:
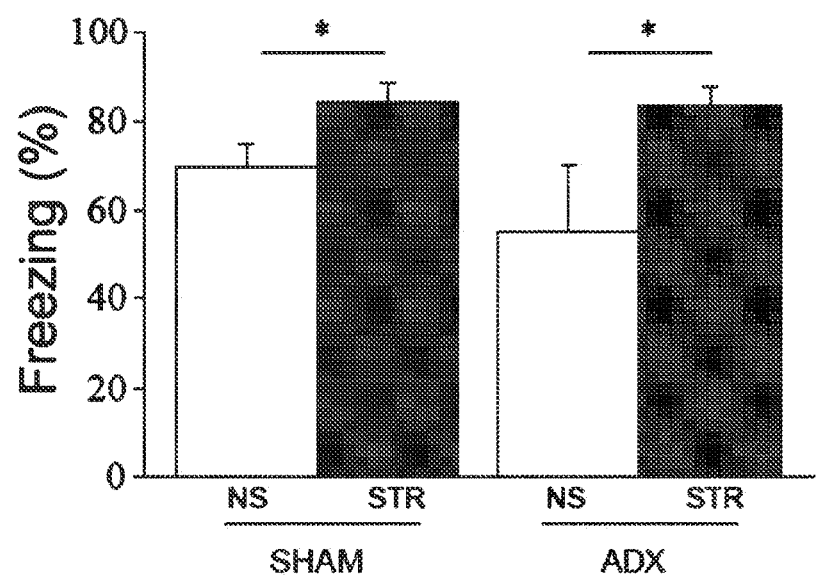
Figure 8C:
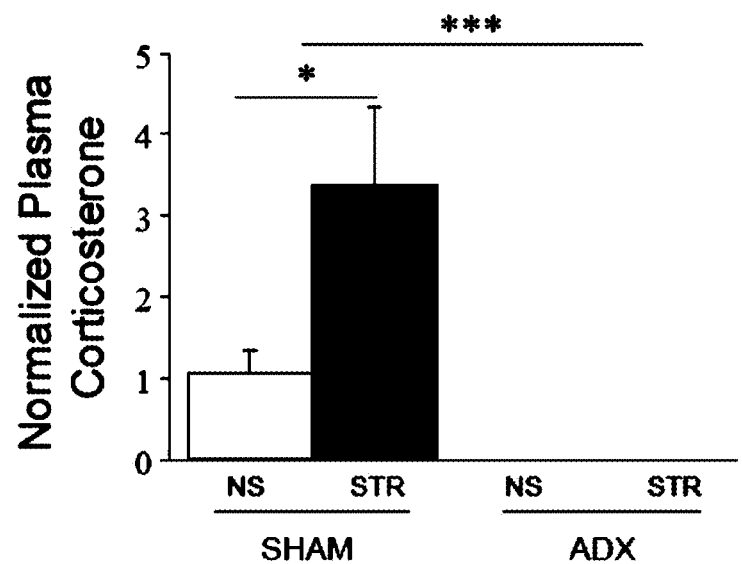

Example 2: Stress-Related Changes in Fear and Ghrelin are Independent of Adrenal Stress Hormones An animal model of PTSD was used in which rats were repeatedly exposed to immobilization stress (4 h/d for 14 d) and subsequently administered auditory fear conditioning. The impact of adrenalectomy on stress-related enhancement of fear conditioning was examined to determine whether stress-induced increases in fear learning require adrenal stress hormones, such as corticosterone or adrenaline. Following adrenalectomy (ADX) or sham surgery (SHAM), animals were exposed to immobilization stress (STR) or daily handling (no stress, or NS). One subset of animals underwent auditory fear conditioning 24 h after the final stress or handling session. Fear to the tone was assessed 48 h post-conditioning. Though a slight enhancement of fear acquisition was seen in stressed rats, this did not reach statistical significance (FIG. 8A, stress: $F(1, 22)=3.98$, $p<0.10$, ns). However, stress produced a robust enhancement of long-term fear memory (FIG. 8B, stress: $F(1,22)=12.17$, $p<0.01$). Surprisingly, this was observed in the complete absence of adrenal stress hormones (FIG. 8B, Surgery X Stress interaction, $F(1,22)=1.3$, p=ns; corticosterone verified as undetectable in all ADX animals, FIG. 8C). The enhancement of fear was specific to fear acquisition and/or consolidation rather than fear expression, locomotion, extinction, or spontaneous immobility (FIG. 12-14). These results show that stress-enhanced fear learning is not mediated by glucocorticoids or adrenaline, consistent with the limited clinical benefit of pharmacological manipulations targeting adrenal hormone signaling in PTSD patients (12, 27). Importantly, these data also show that other stress hormones drive this behavioral change.

Figure 8D:
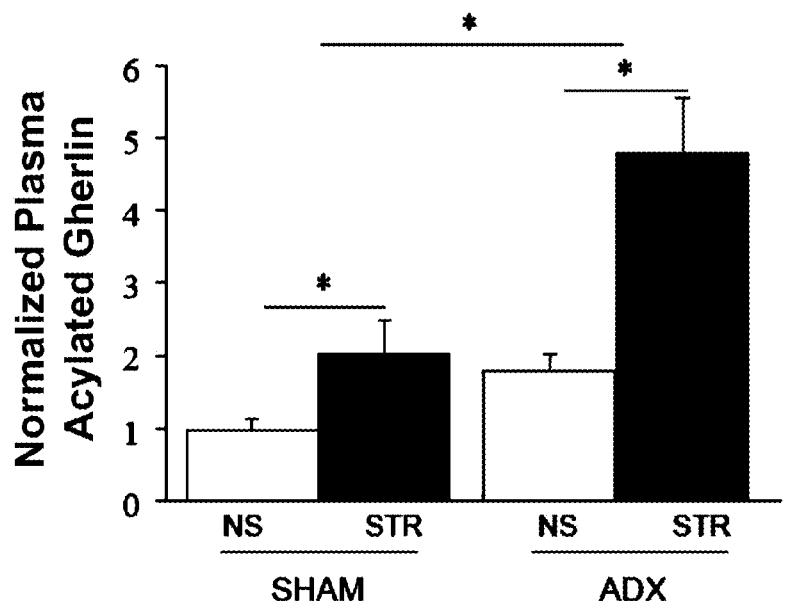
Figure 15:
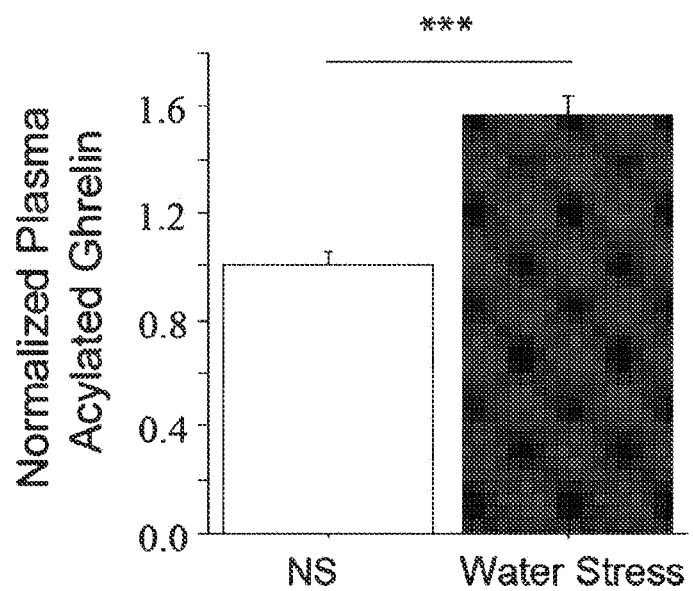
FIG. 15 shows that repeated water stress increases circulating acylated ghrelin levels. Rats received either daily handling (30 s/d, 14 d, NS) or water stress (1 h/d, 14 d, Water Stress). Trunk blood was collected 24 h after the last stress or handling session. Plasma acylated ghrelin was measured by ELISA. All data are mean±s.e.m. *** p<0.001, in planned comparisons.

To discover the relationship between acylated ghrelin and HPA hormones, the impact of adrenalectomy on stress-induced increases in acylated ghrelin was examined. Animals were administered surgical and stress treatments as per the previous experiment but sacrificed 24 h after the final stress or handling session for the collection of blood samples. This was performed during a narrow window surrounding the circadian trough of ghrelin release to minimize hunger-induced variability in ghrelin levels. As expected, corticosterone was significantly elevated by immobilization stress in the SHAM group but undetectable in the ADX group (FIG. 8C, Stress X Surgery interaction: $F(1, 17)=8.37$, $p<0.05$). In contrast, acylated ghrelin was elevated by stress regardless of the presence or absence of the adrenal glands (FIG. 8D, stress: $F(1, 17)=13.19$, $p<0.01$, and Stress X Surgery interaction: $F(1, 17)=2.99$, p=ns). Interestingly, stress-related increases in acylated ghrelin were amplified by adrenalectomy (FIG. 8D, surgery: $F(1, 17)=9.97$, $p<0.01$), showing that adrenal hormones inhibit rather than facilitate ghrelin release (28). Ghrelin is not only elevated by psychological stressors such as immobilization stress, but also by other stressors involving environmental factors (water stress, FIG. 15, stress: $F(1, 14)=33.46$, $p<0.0001$) and social status [social defeat, (13)]. Together, these data reveal that ghrelin is not simply a downstream effector of adrenal hormone recruitment during chronic stress, and may instead represent an independent hormonal pathway of the stress response, broadly recruited by different stressors. Additionally, the elevation of ghrelin by stress in the absence of adrenal hormones suggests that the ghrelin pathway mediates stress-related enhancement of fear.

Figure 9:
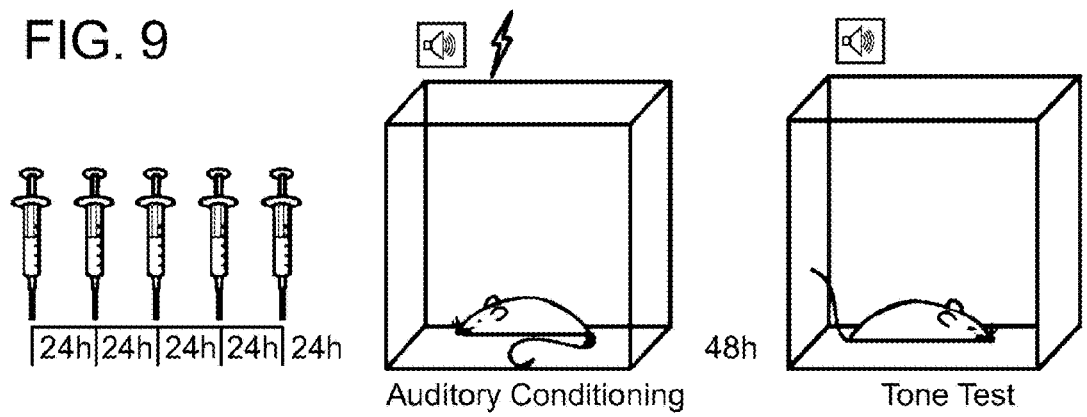
FIG. 9 shows that long-term pharmacological stimulation of ghrelin receptor activity enhances fear memory without altering other stress hormones. Rats received daily systemic injections of MK-0677 (MK: 5 d), a GHSR-1a agonist, or saline (VEH: 5 d) for five days at the endogenous ghrelin signaling nadir. (a) One group underwent auditory fear conditioning 24 h following the final injection. Fear acquisition was assessed by monitoring freezing levels. (b) Conditional freezing to the tone was assessed in a novel context 48 h following fear conditioning. A separate group was sacrificed 24 h following the final injection and microdissections of hypothalamus and amygdala performed. Brain CRF levels were measured using ELISA (c, hypothalamus, d, basolateral complex of the amygdala). * p<0.05, ** p<0.01, ~p<0.10 in planned comparisons.
Figure 9A:
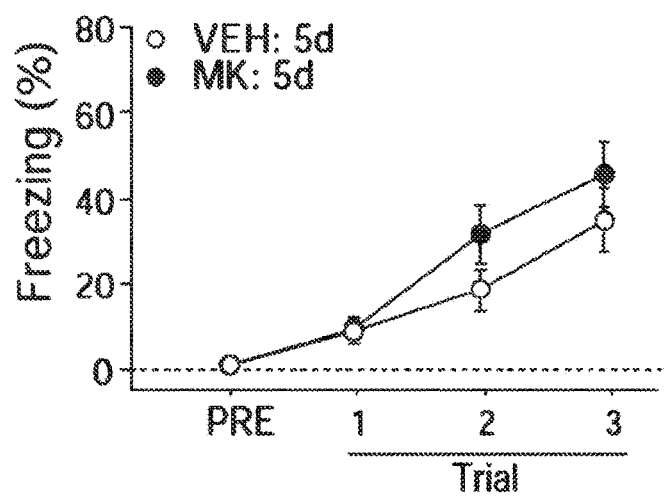
Figure 9B:
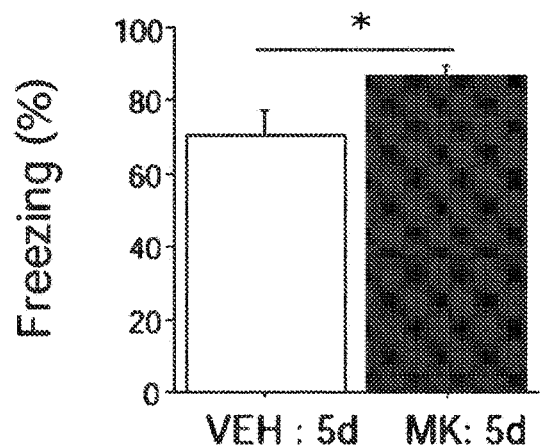
Figure 16E:
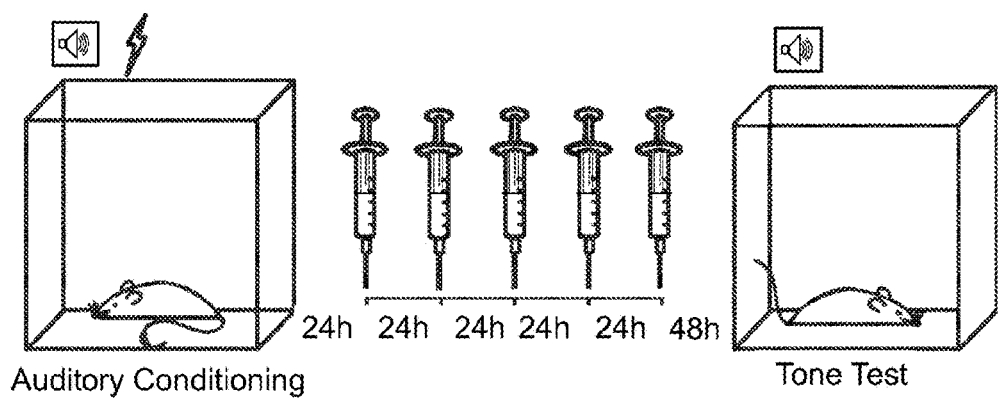
FIG. 16 shows that chronic ghrelin receptor agonism does not alter locomotion, innate anxiety, or expression of previously acquired fear memories. Rats received a daily systemic injection of MK-0677 (MK: 5 d), an agonist of GHSR-1a, or vehicle (VEH: 5 d) for five days at the endogenous ghrelin signaling nadir. Spontaneous freezing (a) and locomotion (b) were assessed in a novel context 24 h after the last injection. A separate group was assessed on the elevated plus maze in a single 8 minute session 24 h after the last injection. Total arm entries (c) and open arm time (d) were measured to assess exploratory behavior and innate anxiety, respectively. (e) Animals received Pavlovian fear conditioning 24 h before beginning daily handling injections of MK-0677 (Post FC MK: 5 d) or vehicle (Post FC VEH: 5 d) for 5 d. Fear memory was assessed by placing the animals in a novel context and measuring conditional freezing following tone presentation 24 h after the last injection. All data are mean±s.e.m.
Figure 16E:
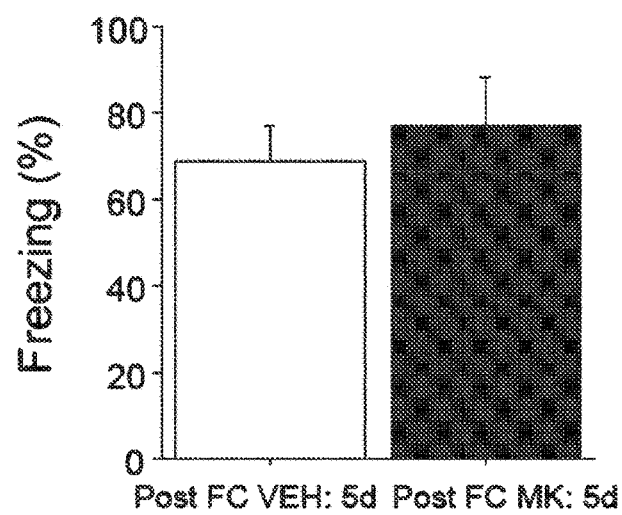

Example 3: Repeated Activation of the Ghrelin Receptor is Sufficient for Enhanced Fear in the Absence of Stress and Independent of the HPA To determine whether increased activation of the ghrelin receptor is sufficient for enhancement of fear memory, experiments were conducted using pharmacological agonism of GHSR-1a in non-stressed animals. Stress-induced changes in acylated ghrelin were observed at the nadir of the diurnal ghrelin cycle, suggesting that stress-related increases in ghrelin persist throughout the day. Because the half-life of acylated ghrelin is short [~30 m (29)], MK-0677, a highly selective GHSR-1a agonist with a half-life of at least 5-6 h (30), was used instead of exogenous acylated ghrelin in order to more closely model the prolonged stress-induced increases in GHSR activation by endogenous ghrelin. MK-0677 (MK: 5 d) or saline (VEH: 5 d) was systemically administered once a day for five consecutive days in non-stressed rats to determine whether repeated ghrelin receptor agonism in the absence of stress is sufficient to increase fear learning and whether HPA hormones may play a role in this effect. Five days of treatment were used because this reflects the minimum number of sessions the immobilization stress must be repeated to see stress-related enhancement of fear (see FIG. 14). One subset of animals was administered auditory fear conditioning 24 h after the last injection. This drug regimen significantly enhanced long-term fear memory (FIG. 9B, injection: $F(1,31)=4.21$, $p<0.05$), but did not alter acquisition during conditioning (FIG. 9A, injection: $F(1, 31)=1.54$, p=ns). This enhancement was similar to the effect of chronic immobilization stress and was not attributable to spontaneous freezing (FIG. 16A, injection: $F(1, 31)=0.25$, p=ns) or a drug-induced decrease in locomotor activity (FIG. 16B and c, injection: $F(1,31)=0.95$, $F(1, 15)=2.44$, p=ns all). Additionally, it was specific to associative aversive processing, as innate anxiety was not altered (FIG. 16D, treatment; $F(1,15)=0.15$, p=ns). Furthermore, just as observed following chronic immobilization stress (see Supplementary Text), fear expression was not altered following chronic ghrelin receptor agonism: previously acquired auditory fear memory was not affected by chronic ghrelin receptor agonism (FIG. 16E, injection: $F(1, 10)=0.30$, p=ns). Additionally, the enhancement of fear memory by repeated ghrelin receptor agonism cannot be attributed to effects of the most recent drug treatment (FIG. 17A, injection; $F(1, 19)=3.70$, $p<0.10$) or delayed effects arising from the first drug treatment (FIG. 17B; injection: $F(1, 6)=0.22$, p=ns). Interestingly, there is a trend towards impairment of fear learning after a single dose of the ghrelin receptor agonist (FIG. 17A, injection; $F(1, 19)=3.7$, $p<0.10$). This effect is similar to the effect of a single immobilization session (See FIG. 14A. These data show that long-term activation of the ghrelin receptor is sufficient to enhance fear memory, with strong parallels to the temporal dynamics of stress exposure.

While stress-related increases in ghrelin are not triggered by the HPA axis, ghrelin could interact with the HPA axis in other ways to enhance fear. For example, the hypothalamic stress hormone corticotrophin-releasing factor (CRF) is secreted by neurons of the paraventricular nucleus, an area dense with GHSR-1a (31), and ghrelin increases CRF mRNA in this area (32). Moreover, hypothalamic CRF neurons project to the amygdala and amygdalar CRF can modulate fear memory (33, 34). Thus, systemic ghrelin receptor agonism could mediate effects on fear learning by increasing CRF release in the amygdala. Additionally, ghrelin receptors have been identified in the adrenal cortex (35). Therefore systemic ghrelin receptor agonism could mediate effects on fear learning by increasing release of adrenal hormones.

Figure 9C:
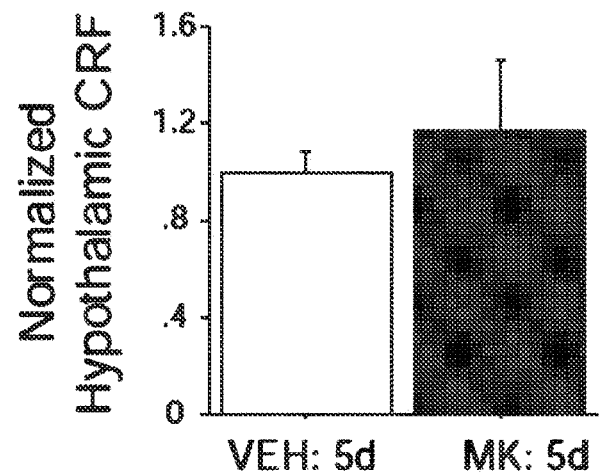
Figure 9D:
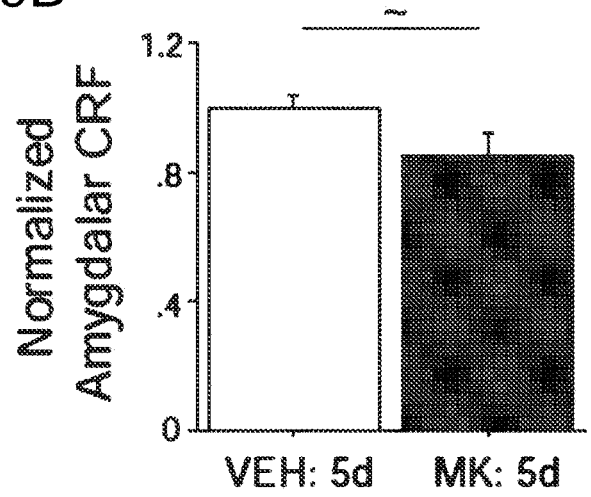
Figure 18:
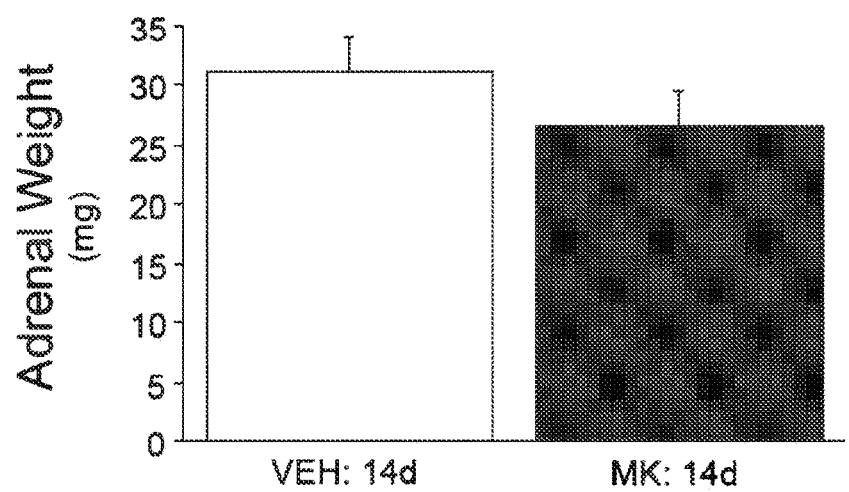
FIG. 18 shows that prolonged ghrelin receptor agonism does not alter adrenal weights. Rats received a daily injections of saline (vehicle, VEH: 14 d) or MK-0677 (MK: 14 d) for 14 days. Adrenal glands were dissected perimortem 24 h after the last injection. All data are mean±s.e.m.

To determine whether the effects of ghrelin on fear learning are mediated through the HPA axis, we examined CRF peptide levels in both the hypothalamus and the amygdala of animals treated as above. There was no change in hypothalamic CRF (FIG. 9C, injection: $F(1, 10)=0.32$, p=ns) and a trend for repeated ghrelin receptor activation to decrease amygdalar CRF levels (FIG. 9D, injection: $F(1, 10)=3.55$, $p<0.10$). In a third group of animals, we examined adrenal weights following a more prolonged period of ghrelin receptor agonism. Increased adrenal weight is seen following prolonged recruitment of adrenocorticotrophin (ACTH) from the pituitary and repeated glucocorticoid and adrenaline production and release from the adrenal glands. Animals received systemic administration of MK-0677 (MK: 14 d) or saline (VEH: 14 d) once a day for 14 days. Repeated systemic ghrelin receptor agonism did not alter this measure (FIG. 18, injection: $F(1,14)=1.24$, p=ns). This suggests that repeated ghrelin receptor agonism at the doses used here does not stimulate the HPA axis.

Figure 19:
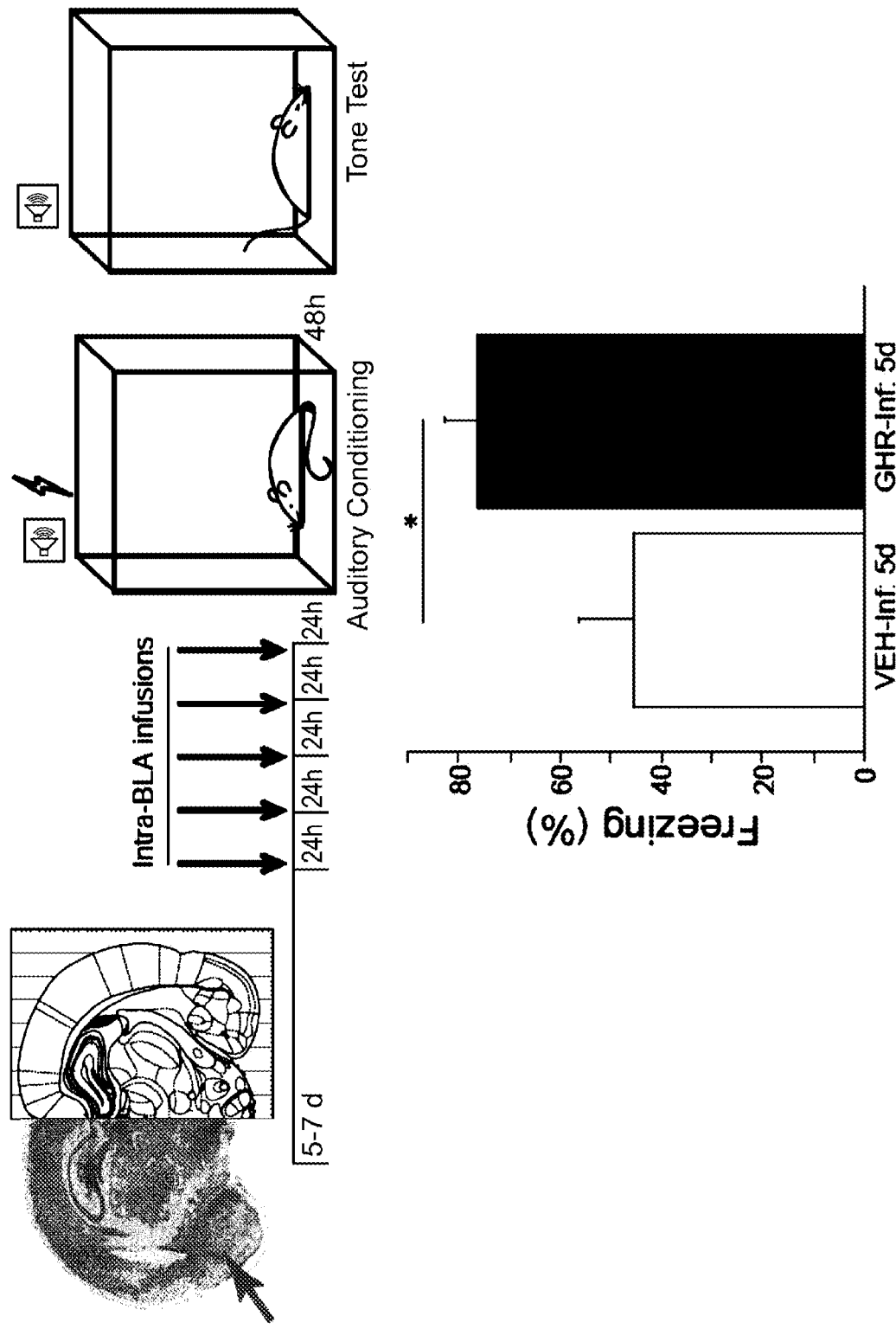
FIG. 19 shows repeated intra-amygdala ghrelin infusions enhance fear memory. Rats were implanted with bilateral cannulae aimed at the basolateral amygdala (BLA). The arrow indicates the tip of the injector within the coronal brain section. Following recovery, intra-BLA infusions of either acylated ghrelin (GHR-Inf: 5 d) or artificial cerebrospinal fluid (vehicle, VEH-Inf: 5 d) were administered daily for five consecutive days and, 24 h following the final infusion, auditory fear conditioning was administered. Fear memory was assessed during tone presentation in a novel context. Brain illustration adapted from (45). All data are mean±s.e.m. * $p<0.05$ in planned comparisons.

Fear memory requires plasticity in numerous brain regions but the basolateral complex of the amygdala (BLA) is particularly important for both formation and storage of learned fear. To determine whether repeated ghrelin receptor activation in the BLA is sufficient to enhance fear memory, either MK-0677 (MK-Inf: 5 d) or artificial cerebrospinal fluid (vehicle, VEH-Inf: 5 d) was infused directly into the BLA daily for five days prior to auditory fear conditioning. Freezing during fear conditioning was not altered by the treatment (FIG. 10A, infusion: $F(1,8)=0.36$, p=ns) but long-term fear memory was significantly enhanced (FIG. 10B, infusion: $F(1,8)=13.75$, $p<0.01$). A similar potentiation of fear memory was observed when acylated ghrelin (GHR) was infused into the BLA daily for five days (FIG. 19; infusion: $F(1,8)=6.07$, $p<0.05$). Collectively, these data show that repeated activation of the ghrelin receptor directly in BLA is sufficient for heightened fear memory. This finding shows that stress-induced increases in circulating ghrelin may enhance fear through actions in the BLA. Additionally, because direct intra-BLA manipulations are unlikely to increase either CRF or ACTH (32), this further shows that ghrelin alters fear by direct actions in the amygdala, rather than through interactions with the HPA axis.

Figure 11A:
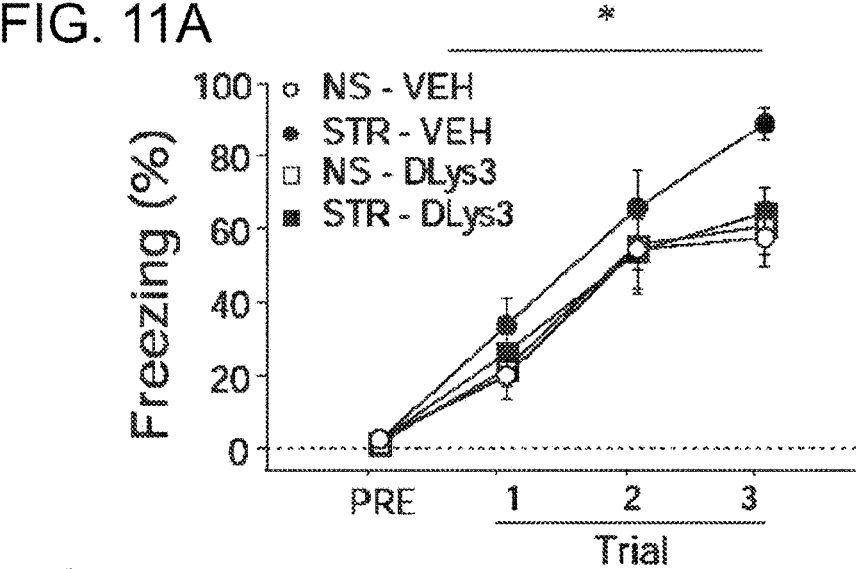
FIG. 11 shows that ghrelin receptor antagonism during chronic stress abolishes stress-related enhancement of fear memory without affecting corticosterone release. Rats received either daily handling (NS) or immobilization stress (STR). Each day, a systemic injection of either Dlys3-GHRP-6 (Dlys3), an antagonist of GHSR-1a, or saline (VEH) was administered within 30 m of handling or stress initiation. (a) Animals received auditory fear conditioning 24 h after the last stress or handling session. (b) Fear memory was assessed 48 h after the conditioning session by placing the animals in a novel context and measuring conditional freezing during tone presentation. (c) In a subset of animals in the STR group, tail bleeds were performed during the final 30 m of the final stress session and plasma corticosterone levels were measured using ELISA. All data are mean±s.e.m. * p<0.05, ~p<0.10 in planned comparisons.
Figure 11B:
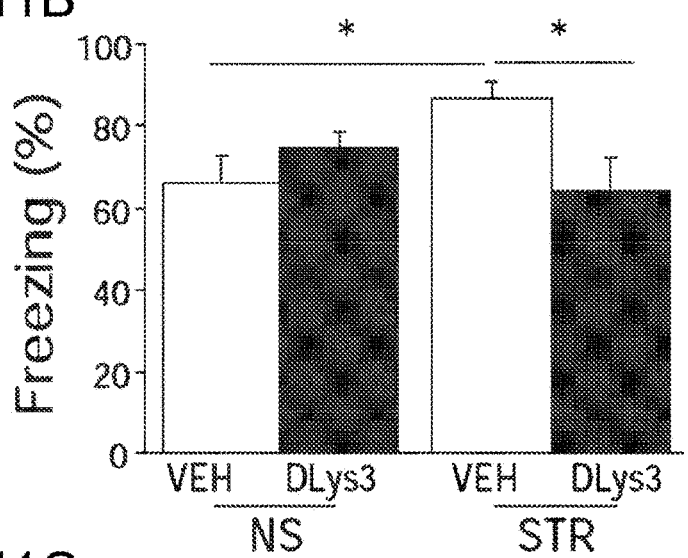
Figure 11C:
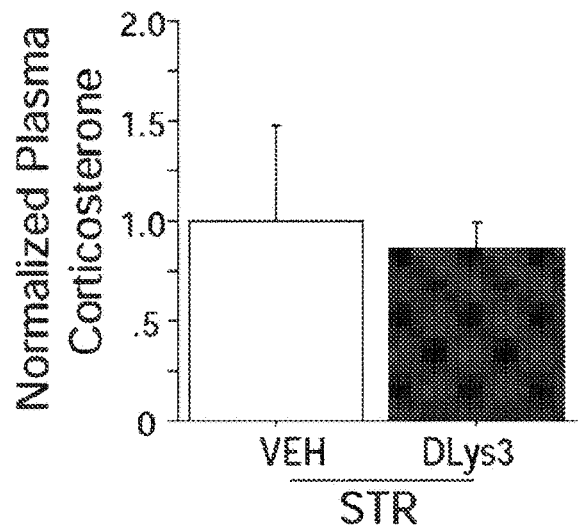

Example 4: The Ghrelin Pathway is Necessary for Stress-Induced Vulnerability to Fear During Chronic Stress To determine whether ghrelin signaling is necessary for stress-related enhancement of fear memory, ghrelin receptor signaling was blocked during repeated stress sessions. Rats were administered immobilization stress (STR) or daily handling (NS) and given either a systemic injection of D-[Lys3]-GHRP-6 (DLys3), a highly specific inverse agonist of GHSR-1a that crosses the blood-brain barrier, or saline (VEH) at the start of each session (30). Twenty-four hours following the final stress or handling session, auditory fear conditioning was administered and fear to the tone was assessed in a subsequent session. Long-term fear memory was enhanced by stress in saline-treated control animals, but DLys3 completely reversed stress-enhanced fear (FIG. 11B; Injection X Stress interaction: $F(1,27)=6.36$, $p<0.05$ and post-hoc comparisons). In contrast, ghrelin receptor antagonism had no effect on fear memory in nonstressed controls (FIG. 11B; post-hoc comparison, NS-SAL vs. NS-Dlys3). Stress enhanced fear acquisition in the saline treated group (FIG. 4a, planned comparisons, treatment, STR-VEH vs NS-VEH; $F(1, 13)=5.03$, $p<0.05$) but this effect was not seen when the ghrelin receptor was antagonized during immobilization stress (FIG. 11A, Trial 3, Stress X Injection interaction: $F(1,27)=3.94$, $p<0.10$). Moreover, DLys3 treatment did not blunt stress-induced HPA activation as measured by corticosterone secretion in stressed animals (FIG. 11C; injection: $F(1, 5)=0.10$, $p=ns$). These data show that ghrelin-mediated signaling is necessary for stress-related enhancement of fear and suggest that other peripheral or central stress hormones are not sufficient to mediate this effect in the absence of heightened ghrelin signaling.

Example 5: Growth Hormone, a Major Effector of the Ghrelin Receptor, Enhances Fear Memory in the Amygdala One of the best-characterized consequences of ghrelin receptor activation is release of GH (36). While the pituitary expresses the highest levels of GH, it is also expressed in other brain regions, including the BLA (18). In one region, GH levels have been shown to increase following acute stress (17). However, it is not known how prolonged stress alters GH in the BLA. The impact of repeated immobilization stress (STR) or daily handling (NS) on GH levels in the BLA was examined to test this. It was found that GH was readily detected in BLA homogenate and significantly upregulated 24 h after chronic stress (FIG. 12A, group: $F(1,16)=6.44$, $p<0.05$), the time point at which increases in circulating ghrelin and fear conditioning were observed. This suggests that ghrelin receptor-mediated signaling in the BLA may be amplified following stress. GH can induce synaptic plasticity (37) and is increased in response to learning (38), but it is unclear how it affects amygdala function. Herpes simplex virus (HSV)-based viral vectors were used to express recombinant rat GH (rGH) and a green fluorescent protein (GFP) reporter or GFP only (39). Naive rats received intra-BLA infusions of either the rGH virus (rGH) or the GFP-only control virus (CON). After three days, when HSV-mediated transgene expression is at its maximum (40), auditory fear conditioning was administered. Fear to the tone was assessed in a subsequent session. Overexpression of rGH did not alter fear acquisition (FIG. 12D; Infusion X Trial interaction: $F(4, 52)=0.57$, $p=ns$) but did enhance fear memory (FIG. 12E, infusion: $F(1, 13)=9.97$, $p<0.01$). These data show that high levels of GH in the BLA are sufficient to enhance fear learning and suggest that ghrelin receptor-mediated alterations in fear memory could be due to increased GH action in BLA.

Figure 20:
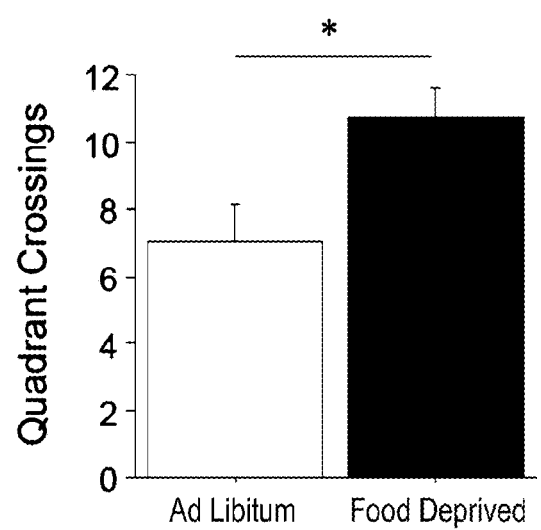
FIG. 20 shows food restriction to 90% body weight increases exploratory locomotion in a novel context. Rats were food deprived for 15 days at 4 g chow per 100 g rat. When rats reached 90% of their initial body weight, they were placed in a novel context with a 3×3 grid floor. The number of border crossings was recorded. All data are mean±s.e.m. * $p<0.05$ in planned comparisons.

In conclusion, it was demonstrated that ghrelin acts in parallel to the HPA axis: adrenalectomy does not affect the ability of stress to enhance fear learning or increase circulating acylated ghrelin. This finding indicates that the observed effects of stress are not simply downstream from HPA hormones. It was also shown that increased ghrelin receptor activity is sufficient and necessary for stress-enhanced fear and is dissociable from HPA activity. Repeated activation of ghrelin receptors in non-stressed animals significantly enhances fear learning without elevating HPA stress hormones, while systemic blockade of the ghrelin receptor during chronic stress prevents stress-related enhancement of fear, even in the presence of elevated adrenal stress hormones. Finally, it was shown that GH, the downstream effector of ghrelin receptor activation, is increased in the BLA by stress and can enhance fear learning. This study was the first to explicitly examine the effects of protracted exposure to elevated ghrelin, as observed following chronic stress. This study shows that there are profound differences in the behavioral consequences of ghrelin exposure following different exposure durations, similar to the cumulative nature of stress. It also provides the first evidence to link prolonged exposure to elevated ghrelin with a specific, detrimental consequence of stress: enhanced fear memory. In contrast, prior studies have argued that ghrelin promotes adaptive changes during stress, including antidepressant effects (13) and reduction in anxiety (41). However, these studies either focused exclusively on acute ghrelin manipulations or used short- and long-term ghrelin manipulations interchangeably. Additionally, the alterations in ghrelin levels were achieved through artificial states: heightened ghrelin levels were attained by extreme food deprivation or a single bolus injection of the short-lived peptide. These treatments potentiate locomotor activity (see FIG. 20) which may contribute to the behavioral effects previously reported. Here, changes in endogenous ghrelin following stress were demonstrated, and then an appropriately low dose, long acting agonist was used to replicate the naturally occurring ghrelin state. Moreover, it is important to note that the changes in fear reported here occurred following small, but persistent, changes in ghrelin signaling, and all were in the absence of any locomotor effects.

The present data show that stress-related changes in amygdala-based aversive processing are not dependent on HPA activity and that ghrelin plays an important role in stress-related affective dysfunction by actions independent of the HPA axis. This does not discount the role of the HPA axis in coordinating other aspects of the stress response. It is clear that the HPA hormonal cascade can account for numerous stress effects [for review see (42)]. However, this work may need to be re-examined through the lens of putative parallel stress pathways such as ghrelin. Future work will be needed to explore the possible synergistic effects of co-activation of the HPA axis and the ghrelin system during chronic stress.

No current treatments exist for preventing stress-related affective disorders, suggesting that the most intriguing and important finding is that blockade of ghrelin signaling during stress is sufficient to prevent stress-related vulnerability to excessive fear. This raises the possibility that such a strategy might reduce or prevent the development of stress-sensitive affective disorders like PTSD during prolonged or extreme stress load. While there are some non-HPA molecules which might be targeted in the treatment of PTSD [such as brain-derived neurotrophic factor, tissue plasminogen activator, or FKBP5; for review, see (43)], the dysregulation of these molecules in PTSD models is brain region-specific. To effectively treat PTSD, pharmaceuticals for these molecules would need to cross the blood-brain barrier and act in a brain region-specific manner to minimize off-target side effects. Furthermore, there are no pharmaceuticals that can readily affect these molecules in humans. In contrast, because ghrelin is a peripheral hormone, it can be targeted using therapeutics that act in the periphery. Also, many anti-ghrelin treatments already have been tested for human use due to its putative role in the development of obesity (44). Thus, the discovery that ghrelin plays a role in stress-related affective dysregulation reveals an especially attractive target for treating stress-sensitive affective disorders.

Figure 12A:
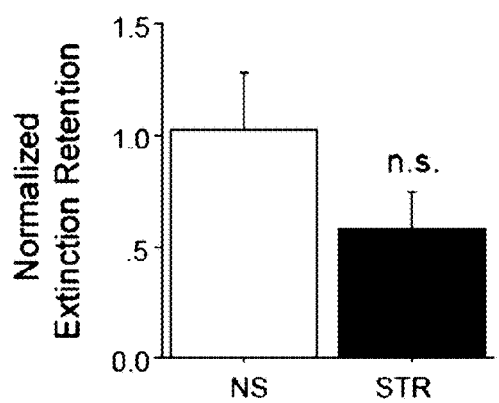
FIG. 12 shows that chronic stress does not alter extinction or expression of previously acquired fear memories. Rats in the SHAM group from FIG. 12 received either daily handling (NS) or immobilization stress (STR). Animals received Pavlovian fear conditioning 24 h after the last stress or handling session. Fear memory was assessed by placing the animals in a novel context 48 h after the conditioning session and measuring conditional freezing following tone presentation. (a) An extinction test was performed 48 h after the fear memory test during which animals were returned to the extinction context and presented with additional tones. Extinction retention measures the memory strength for the extinction learning acquired during the first extinction session. It is calculated as the difference in initial freezing levels between the first and the second extinction sessions. This value is normalized to the NSSHAM group. (b) In a second group, intact animals received Pavlovian fear conditioning 24 h before beginning daily handling (Post FC: NS) or immobilization stress (Post FC: STR) for 14 d. Fear memory was assessed by placing the animals in a novel context and measuring conditional freezing following tone presentation 24 h after the last stress or handling session. All data are mean±s.e.m.
Figure 12B:
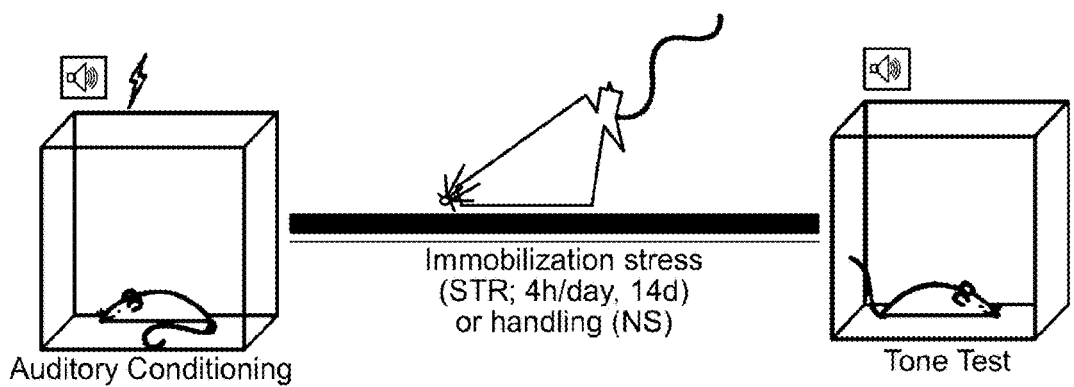
Figure 12B:
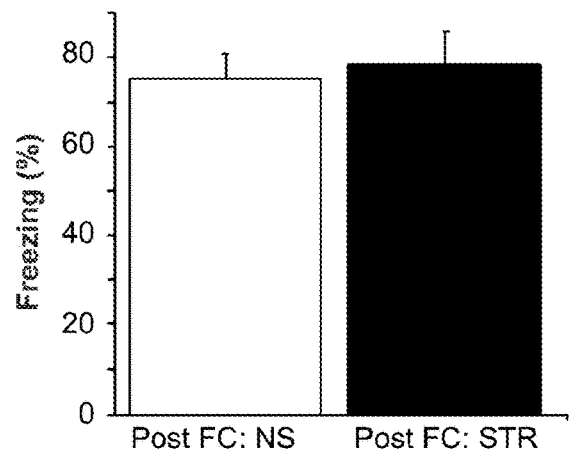
Figure 13B:
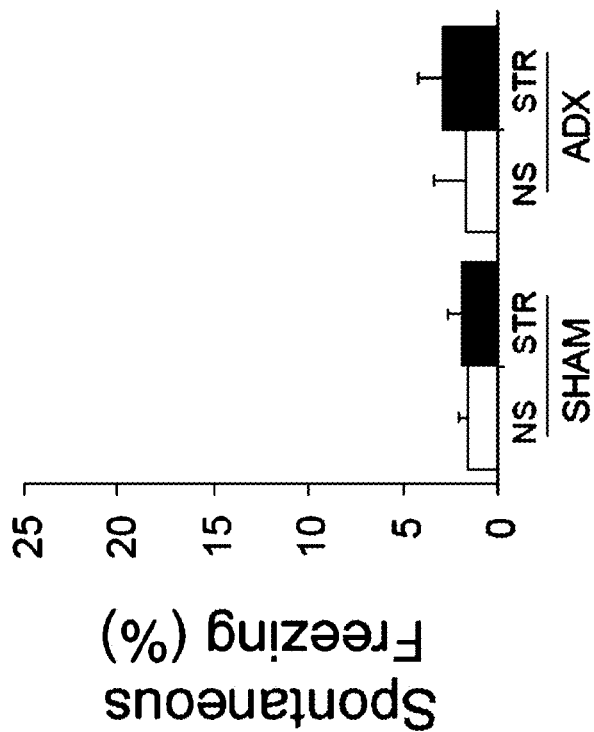
FIG. 13 shows that adrenalectomy and immobilization stress do not alter locomotion or spontaneous freezing levels. Rats from FIG. 12 received either daily handling (NS) or immobilization stress (STR). Locomotion (a) and spontaneous freezing (b) in a novel environment were assessed prior to fear conditioning. All data are mean±s.e.m.
Figure 13A:
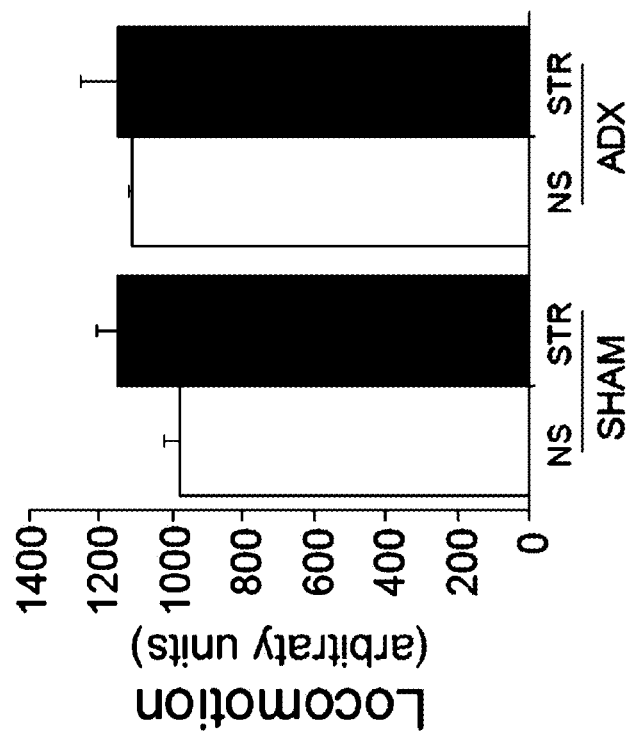
Figure 14A:
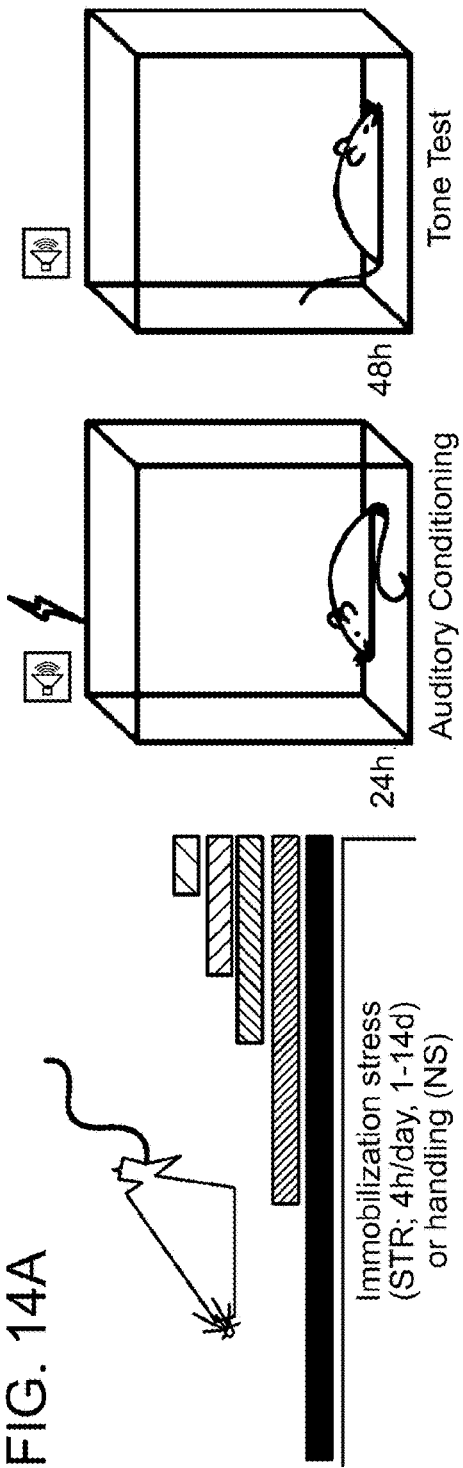
FIG. 14 shows that stress-induced enhancement of fear arises after 5 consecutive days of stressor exposure. (a) Rats received either daily handling (30 s/d, 14 d, NS) or immobilization stress (4 h/d, STR) for 1, 2, 4, 7 or 14 days. Animals received auditory Pavlovian fear conditioning 24 h after the last stress or handling session. Fear to the tone was assessed 48 h later. (b) In a separate group of animals, rats received either daily handling (30 s/d, 5 d, NS) or immobilization stress (4 h/d, STR) for 5 days. Animals received auditory Pavlovian fear conditioning 24 h after the last stress or handling session. Fear to the tone was assessed 48 h later. (c) In a third group of animals, rats received a single handling (NS) or immobilization stress (STR) session. They were then returned to the vivarium for 14 d before receiving auditory Pavlovian fear conditioning. Fear to the tone was assessed 48 h later. All data are mean±s.e.m. * p<0.05, ~p<0.10 in planned comparisons.
Figure 14A:
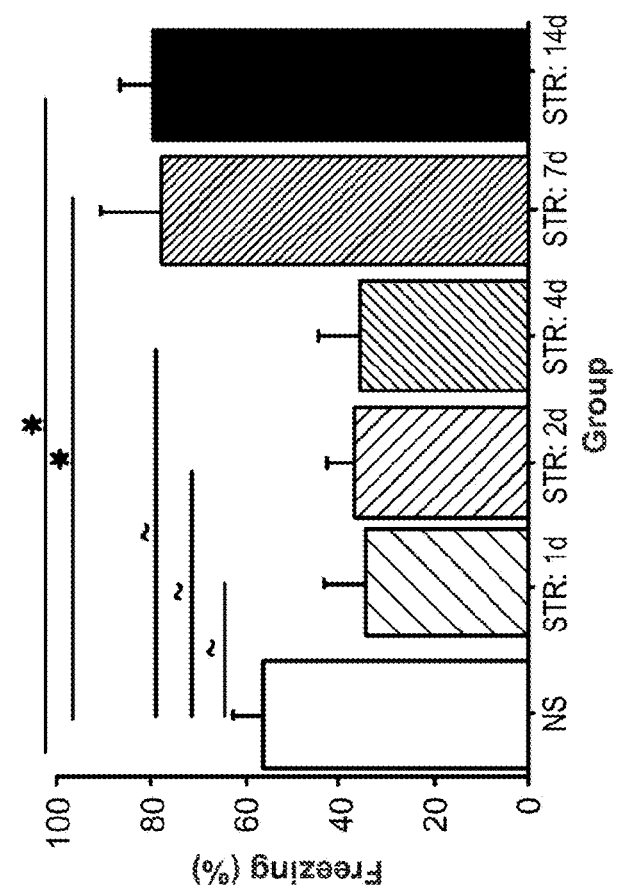
Figure 14B:
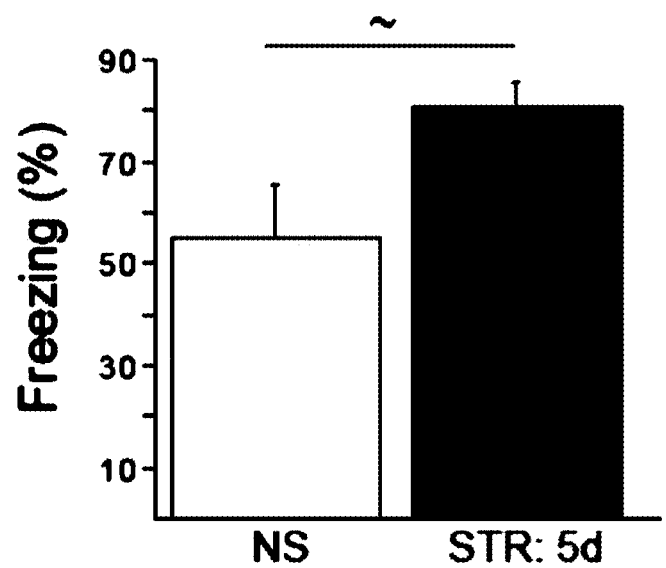
Figure 14C:
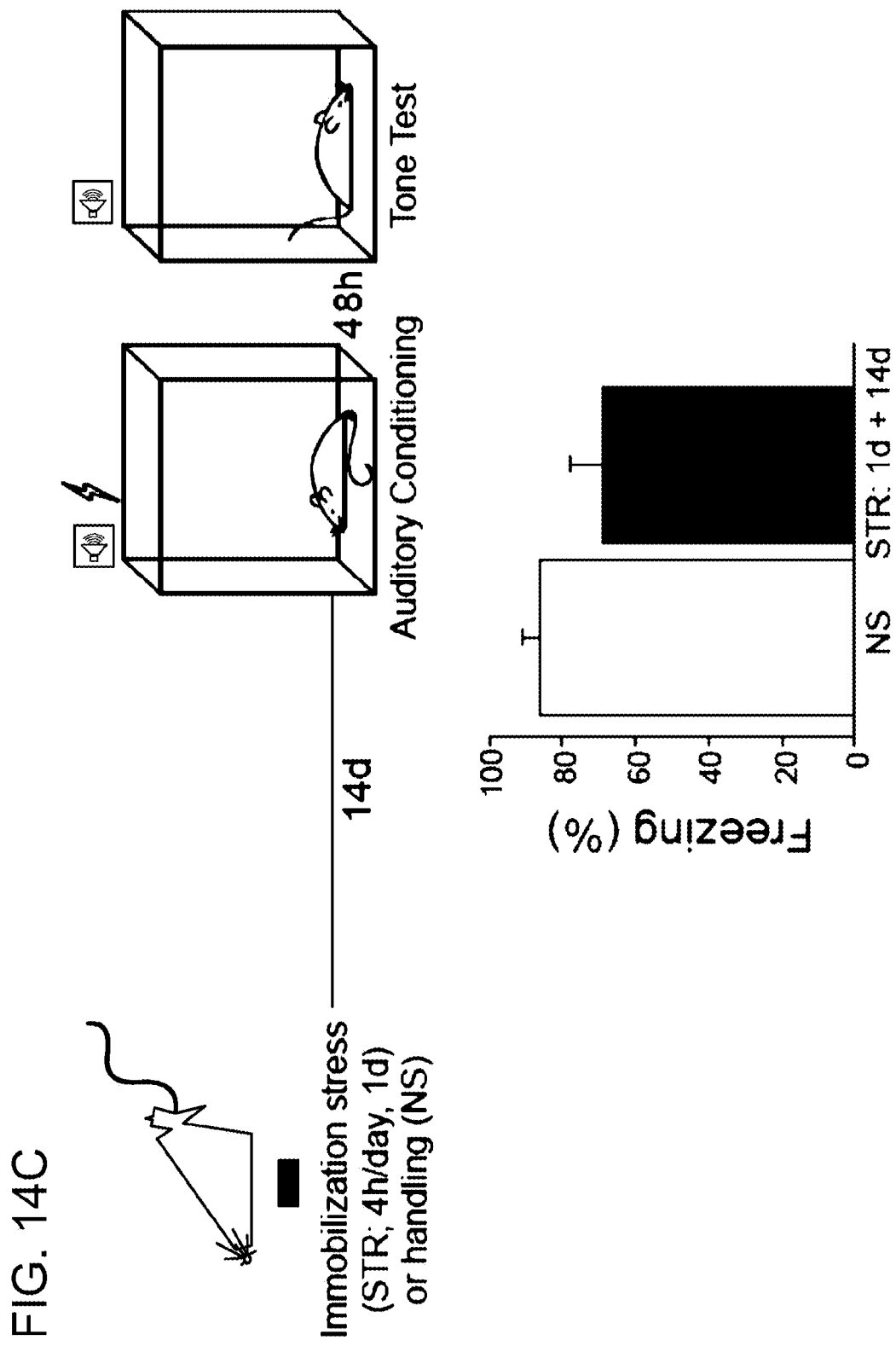

The enhancement in long-term fear memory after stress cannot be explained by stress related changes in extinction nor memory retrieval: no difference in extinction retention was observed in a second extinction test performed 48 h after the initial extinction session (FIG. 12A; stress: $F(1, 12)=2.15$, p=ns), and stress administered after fear conditioning did not alter the expression of previously acquired fear memories (FIG. 12B; stress: $F(1, 17)=0.107$, p=ns). The high levels of conditional freezing seen in rats in the STR or ADX groups also cannot be explained by non-specific decreases in locomotor activity (FIG. 13A; stress: $F(1, 22)=1.52$, p=ns and surgery: $F(1,22)=0.56$, p=ns) or increases in spontaneous freezing (FIG. 13B; stress: $F(1, 22)=0.37$, p=ns and surgery: $F(1,22)=0.23$, p=ns). Stress-related enhancement of fear was also not due to the most recent stress session: a single session of immobilization stress was not sufficient to increase subsequent fear learning (FIG. 14A). Stress-related enhancement of fear also did not stem from delayed effects of the first stress exposure as has been shown in other aspects of stress (9, 53): a single exposure to immobilization stress did not affect fear conditioning administered 14 d later (FIG. 14B, stress: $F(1, 6)=2.90$, p=ns). Rather, stress related increases in fear memory appeared after cumulative stress exposure of a approximately five or more days for this particular stressor (FIGS. 14A & 14B: $F(5, 46)=5.01$, $p<0.01$ and $F(1, 13)=4.62$, $p<0.10$, respectively).

The antidepressant effect of ghrelin requires high levels of ghrelin, as found in food-restricted rodents after 10-15% weight loss (13). It was found that this level of food deprivation leads to increased exploratory motor activity (FIG. 20; $F(1, 13)=7.51$, $p<0.05$). A recent study reports similar motor effects following acute ghrelin manipulations (54). These motor effects can be a significant confound.

The present data shows that as a stress hormone, ghrelin may be similar to glucocorticoids: under "normal" conditions, there is an optimal level of the hormone (55) and too little (56, 57) or too much hormonal signaling (16) can lead to dysfunction in neuronal circuits. According to such a model, repeated activation of these two hormone pathways contributes to stress-induced wear and tear on the body, or allostatic load. In this regard, heightened ghrelin signaling may have both advantageous and undesirable consequences, but these must be carefully considered with respect to the length and level of elevated ghrelin exposure.

EQUIVALENTS

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Those skilled in the art will recognize, or be able to ascertain using no more than routine experimentation, many equivalents to the specific embodiments of the invention described herein. Such equivalents are intended to be encompassed by the following claims. All references, including patent documents, disclosed herein are incorporated by reference in their entirety, particularly for the disclosure referenced herein.

REFERENCES

1. B. S. McEwen, N Engl J Med 338, 171 (Jan. 15, 1998).
2. F. Lederbogen et al., Nature 474, 498 (Jun. 23, 2011).
3. C. Mazure, Does Stress Cause Psychiatric Illness?, Progress in Psychiatry (American Psychiatric Press, Inc., Washington, D.C., 1995), pp. 281.
4. J. K. Belanoff, B. H. Flores, M. Kalezhan, B. Sund, A. F. Schatzberg, J Clin Psychopharmacol 21, 516 (October, 2001).
5. R. P. Juster et al., Dev Psychopathol 23, 725 (August, 2011).
6. M. M. Miller, B. S. McEwen, Ann N Y Acad Sci 1071, 294 (July, 2006).
7. B. S. McEwen, Biol Psychiatry 54, 200 (Aug. 1, 2003).
8. A. C. Schwartz, R. L. Bradley, M. Sexton, A. Sherry, K. J. Ressler, Psychiatr Serv 56, 212 (February, 2005).
9. R. Mitra, R. M. Sapolsky, Proc Natl Acad Sci USA 105, 5573 (Apr. 8, 2008).
10. C. D. Conrad et al., Neurobiol Learn Mem 81, 185 (May, 2004).
11. T. Frodl, V. O'Keane, Neurobiol Dis, (Mar. 9, 2012).
12. C. P. Searcy, L. Bobadilla, W. A. Gordon, S. Jacques, L. Elliott, Mil Med 177, 649 (June, 2012).
13. M. Lutter et al., Nat Neurosci 11, 752 (July, 2008).
14. J. Zheng, A. Dobner, R. Babygirija, K. Ludwig, T. Takahashi, Am J Physiol Regul Integr Comp Physiol 296, R1358 (May, 2009).
15. M. Alvarez-Crespo et al., PLoS One 7, e46321 (2012).
16. V. P. Carlini et al., Biochem Biophys Res Commun 313, 635 (Jan. 16, 2004).
17. C. P. Donahue, K. S. Kosik, T. J. Shors, Proc Natl Acad Sci USA 103, 6031 (Apr. 11, 2006).
18. S. T. Pacold, L. Kirsteins, S. Hojvat, A. M. Lawrence, Science 199, 804 (Feb. 17, 1978).
19. E. M. Glover et al., Depress Anxiety 28, 1058 (Dec. 21, 2011).
20. J. D. Bremner et al., Psychol Med 35, 791 (June, 2005).
21. R. K. Pitman et al., Nat Rev Neurosci 13, 769 (November, 2012).
22. V. Rau, J. P. DeCola, M. S. Fanselow, Neurosci Biobehav Rev 29, 1207 (2005).
23. C. D. Conrad, J. E. LeDoux, A. M. Magarinos, B. S. McEwen, Behav Neurosci 113, 902 (October, 1999).
24. A. Vyas, R. Mitra, B. S. Shankaranarayana Rao, S. Chattarji, J Neurosci 22, 6810 (Aug. 1, 2002).
25. T. Jovanovic et al., Psychoneuroendocrinology 35, 846 (July, 2010).
26. M. Popoli, Z. Yan, B. S. McEwen, G. Sanacora, Nat Rev Neurosci 13, 22 (January, 2012).
27. E. A. Hoge et al., CNS Neurosci Ther 18, 21 (January, 2012).
28. B. Otto, M. Tschop, W. Heldwein, A. F. Pfeiffer, S. Diederich, Eur J Endocrinol 151, 113 (July, 2004).
29. M. Tschop, D. L. Smiley, M. L. Heiman, Nature 407, 908 (Oct. 19, 2000).
30. R. G. Smith et al., Science 260, 1640 (Jun. 11, 1993).

31. X. M. Guan et al., Brain Res Mol Brain Res 48, 23 (August, 1997).
32. A. Cabral, O. Suescun, J. M. Zigman, M. Perello, PLoS One 7, e31462 (2012).
33. K. Isogawa, D. E. Bush, J. E. Ledoux, Biol Psychiatry, (Oct. 1, 2012).
34. B. Roozendaal, G. Schelling, J. L. McGaugh, J Neurosci 28, 6642 (Jun. 25, 2008).
35. M. Papotti et al., J Clin Endocrinol Metab 85, 3803 (October, 2000).
36. M. Kojima et al., Nature 402, 656 (Dec. 9, 1999).
37. G. S. Mahmoud, L. M. Grover, J Neurophysiol 95, 2962 (May, 2006).
38. C. P. Donahue et al., Hippocampus 12, 821 (2002).
39. C. M. Vander Weele, C. Saenz, J. Yao, S. S. Correia, K. A. Goosens, Submitted, (2013).
40. W. A. Carlezon, Jr. et al., Science 282, 2272 (Dec. 18, 1998).
41. S. J. Spencer et al., Biol Psychiatry 72, 457 (Sep. 15, 2012).
42. S. M. Rodrigues, J. E. LeDoux, R. M. Sapolsky, Annu Rev Neurosci 32, 289 (2009).
43. A. L. Mahan, K. J. Ressler, Trends Neurosci 35, 24 (January, 2012).
44. I. Seim, M. El-Salhy, T. Hausken, D. Gundersen, L. Chopin, Curr Pharm Des 18, 768 (2012).
45. G. Paxinos, C. Watson, The Rat Brain in Stereotaxic Coordinates—The New Coronal Set, Fifth Edition. (Elsevier Academic Press, San Diego, 2005).
46. F. Lim, R. Neve, in Current Protocols in Neuroscience. (John Wiley and Sons, 2001), vol. 6, pp. 4.13.1-4.13.17.
47. C. H. Chang et al., Endocrinology 137, 4851 (November, 1996).
48. T. Jacks et al., Endocrinology 137, 5284 (December, 1996).
49. L. Pinilla, M. L. Barreiro, M. Tena-Sempere, E. Aguilar, Neuroendocrinology 77, 83 (February, 2003).
50. K. Sethumadhavan, K. Veeraragavan, C. Y. Bowers, Biochem Biophys Res Commun 178, 31 (Jul. 15, 1991).
51. M. Traebert, T. Riediger, S. Whitebread, E. Scharrer, H. A. Schmid, J Neuroendocrinol 14, 580 (July, 2002).
52. A. Asakawa et al., Gut 52, 947 (July, 2003).
53. R. Mitra, S. Jadhav, B. S. McEwen, A. Vyas, S. Chattarji, Proc Natl Acad Sci USA 102, 9371 (Jun. 28, 2005).
54. C. Hansson et al., PLoS One 7, e50409 (2012).
55. V. P. Carlini et al., Physiol Behav 101, 117 (Aug. 4, 2010).
56. S. Diano et al., Nat Neurosci 9, 381 (March, 2006).
57. J. F. Davis, D. L. Choi, D. J. Clegg, S. C. Benoit, Physiol Behav 103, 39 (Apr. 18, 2011).

---

What is claimed is:

1. A method of protecting against stress-sensitive disorders associated with chronic stress in a subject in need thereof, comprising
administering to the subject a therapeutically effective amount of an agent that reduces the level or activity of ghrelin or ghrelin receptor, compared to before the agent is administered,
wherein the agent is a growth hormone secretagogue receptor 1a (GHSr1a) antagonist, a GHSr1a inverse agonist, an enzyme that deacylates ghrelin, or an agent that inhibits the activity of ghrelin O-acyltransferase (GOAT); and
wherein the stress-sensitive disorder is selected from the group consisting of: post-traumatic stress disorder (PTSD), depressive disorder, major depressive disorders, bipolar disorder, acute stress disorder, generalized anxiety disorder, obsessive-compulsive disorder, social anxiety disorders, panic disorders, phobias, and trichotillomania.

2. The method of claim 1 wherein the agent is administered before, during and/or after exposure of the subject to chronic stress.

3. The method of claim 1 wherein the agent is a GHSr1a antagonist or a GHSr1a inverse agonist.

4. The method of claim 1 wherein the agent is an anti-ghrelin vaccine.

5. The method of claim 1 wherein the agent inhibits the activity of GOAT.

6. The method of claim 5, wherein the agent is an anti-GOAT vaccine.

7. The method of claim 1, wherein the agent is an enzyme that deacylates ghrelin.

8. The method of claim 1, wherein the chronic stress is associated with military service or a natural disaster.

9. The method of claim 7, wherein the enzyme that deacylates ghrelin is an esterase.

10. The method of claim 9, wherein the esterase is acyl protein thioesterase 1 (APT1).

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Modified with Octanoyl
<220> FEATURE:
<221> NAME/KEY: misc_feature
<222> LOCATION: (4)..(4)
<223> OTHER INFORMATION: Modified with OH or NH2

<400> SEQUENCE: 1

Gly Ser Ser Phe
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 2

Leu Ser Pro Glu Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: misc_feature
<222> LOCATION: (6)..(6)
<223> OTHER INFORMATION: Modified with OH or NH2

<400> SEQUENCE: 3

Ala Lys Leu Gln Pro Arg
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Modified with Octanoyl

<400> SEQUENCE: 4

Gly Ser Ser Phe Leu Ser Pro Glu
1               5
```